United States Patent [19]

Nagai et al.

[11] Patent Number: 5,166,204
[45] Date of Patent: Nov. 24, 1992

[54] ISOINDOLE DERIVATIVES AND SALTS THEREOF AND ANTITUMOR AGENT COMPRISING THE SAME

[75] Inventors: Takashi Nagai; Isao Myoukan; Keishi Funaki, Toyama; Kenji Ohta, Takaoka; Nobuhisa Taya, Shinminato; Shinji Miyabara; Masaaki Shibata, both of Toyama; Hidetada Mikami, Takaoka; Takako Hori, Toyama, all of Japan

[73] Assignee: Toyama Chemical Co., Ltd., Tokyo, Japan

[21] Appl. No.: 605,430

[22] Filed: Oct. 30, 1990

[30] Foreign Application Priority Data

Nov. 1, 1989 [JP] Japan .................. 1-285548
Aug. 2, 1990 [JP] Japan .................. 2-205443
Oct. 25, 1990 [JP] Japan .................. 2-288069

[51] Int. Cl.$^5$ .................. A61K 31/40; A61K 31/535; C07D 487/04; C07D 495/04
[52] U.S. Cl. .................. 514/232.8; 514/253; 514/316; 514/321; 514/339; 514/410; 544/142; 544/372; 546/187; 546/198; 546/271; 548/418; 548/423
[58] Field of Search .................. 548/423, 418; 514/410, 514/232.8, 253, 316, 321, 339; 544/142, 372; 546/187, 198, 271

[56] References Cited

FOREIGN PATENT DOCUMENTS 0303697 2/1989 European Pat. Off. .
3833008 4/1990 Fed. Rep. of Germany .

OTHER PUBLICATIONS

*J. Org. Chem.*, (1990), 55, pp. 5368-5374, "Reactions of 2-Vinylindoles with Carbodienophiles: Synthetic and Mechanistic Aspects", Eitel et al.
*Tetrahedron Letters*, (1985), 26, pp. 4015-4018, "Two Synthetic Approaches to Rebeccamycin", Kaneko et al.
*Chemiker-Zeitung*, (1988), 112, pp. 235-238, "1,4-Dihydro- und 2,4-Dihydropyrrolo[3,4-b]indole mit Donator-Gruppen in 3-Stellung[1]", Dyker et al.
*J. Org. Chem.*, (1989), 54, pp. 824-828, "Synthesis of indolo[2,3-a]pyrrolo[3,4-c]carbazoles by Dougle Fischer Indolizations", Bergman et al.
*Yakugaku Zasshi*, (1968), 88, pp. 767-773, "Studies on Indole Derivatives. VII. Diels-Alder Reaction of 2-Oxo-4-methylthiopyrano-[2,3-b]..." Kobayashi et al.
*Yakagaku Zasshi*, (1969), 89, pp. 58-63, "Studies on Indole Derivatives. VIII. Synthesis of Thieno [2,3-B-]indole Derivatives and Their ..." Kobayashi et al.
*Chimia*, (1988), 42, pp. 180-183, "Constitution and Stereochemistry of the Diels-Alder Products from the Reaction of 1-Methylpyrano ..." Pindur et al.
*Chem. Pharm. Bull.*, (1984), 32, pp. 902-908, "Pyridazino[4,5-B]Carbazole: Synthese et Etude des Spectres de Resonance Magnetique Nucleaire" Lancelot et al.
*Arm. Khim. ZH.*, (1968), 21, pp. 793-807.

*Primary Examiner*—Mary C. Lee
*Assistant Examiner*—Mary Susan H. Gabilan
*Attorney, Agent, or Firm*—Oblon, Spivak, McClelland, Maier & Neustadt

[57] ABSTRACT

A novel isoindole derivative represented by general formula [1] or a salt thereof:

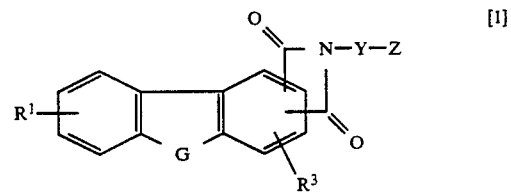

which has an excellent antitumor activity and low toxicity.

21 Claims, No Drawings

ISOINDOLE DERIVATIVES AND SALTS THEREOF AND ANTITUMOR AGENT COMPRISING THE SAME

This invention relates to a novel compound having a strong antitumor activity, and more particularly to a specific isoindole derivative represented by general formula [1] which will be shown hereinafter or a salt thereof.

Various isoindole derivatives are known; however, no isoindole derivatives have been known in which a group represented by the formula:

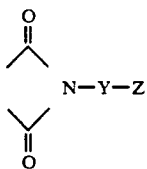

wherein Y represents a linkage or a lower alkylene group and Z represents a halogen atom, an unprotected or protected hydroxyl group, a group of the formula,

(in which $R^4$ and $R^5$, which may be the same or different, represent hydrogen atoms or unsubstituted or substituted lower alkyl, cycloalkyl, aralkyl, acyl or aryl groups, or may form, with the nitrogen atom to which they are bonded, an unsubstituted or substituted nitrogen-containing heterocyclic group) or a trialkylammonio or cyclic ammonio group, is bonded to the 2- and 3- and 4-positions of a carbazole skeleton or to the 1- and 2- or 2- and 3-positions of a dibenzofuran or dibenzothiophen skeleton.

The chemotherapy in an oncological field has been improved over recent several tens of years to such an extent that some cancers such as leukemia and the like have become curable with only a chemotherapeutic agent with a high cure rate. However, the cure rate against the cancer of internal organs such as colon, stomach, lung and the like, which are now considered to be the most important target for the chemotherapy, is very low. This problem is now the most important and urgent matter for a mankind to solve. The resistance acquisitions of tumor cells to chemotherapeutic agents and the toxicities of chemotherapeutic agents against normal cells are also serious problems. Under these circumstances, the development of new antitumor drugs which overcome the deficiencies of currently used antitumor drugs is greatly desired.

The inventors of this invention have made extensive research on compounds having antitumor activity and low toxicity in order to solve the above-mentioned problems, and as a result, have found that isoindole derivatives having general formula [1] which will be shown hereinafter can solve the above problems.

According to this invention, there is provided an isoindole derivative represented by general formula [1] or a salt thereof:

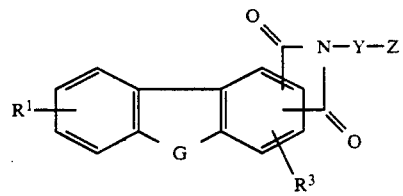

wherein $R^1$ and $R^3$ may be the same or different, and each of them represents at least one group selected from the group consisting of hydrogen and halogen atoms, nitro and methylenedioxy groups, unprotected or protected amino, hydroxyl and carboxyl groups and unsubstituted or substituted lower alkyl, alkenyl, lower alkylthio, cycloalkyl, aryl, aryloxy, carbamoyloxy, acyl, heterocyclic carbonyloxy and hetereocyclic groups, G represents an oxygen atom or a group represented by the formula $>S(=O)_n$ (in which n is 0, 1 or 2), or $>NR^2$ (in which $R^2$ is a hydrogen atom or an unsubstituted or substituted lower alkyl, aryl, aralkyl, carbamoyl or acyl group), Y represents a linkage or a lower alkylene group, Z represents a halogen atom, an unprotected or protected hydroxyl group, a group represented by the formula

(in which $R^4$ and $R^5$, which may be the same or different, represent hydrogen atoms or unsubstituted or substituted lower alkyl, cycloalkyl, aralkyl, acyl or aryl groups, or may form, with the nitrogen atom to which they are bonded, an unsubstituted or substituted nitrogen-containing heterocyclic group) or a trialkylammonio or cyclic ammonio group, and the group represented by the formula:

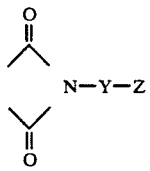

wherein Y and Z have the meanings as defined above is bonded to the 2- and 3- or 3- and 4-positions of a carbazole skeleton or to the 1- and 2- or 2- and 3-positions of a dibenzofuran or dibenzothiophene skeleton, a process for producing the same, and an antitumor agent containing the same.

It is an object of this invention to provide a novel isoindole derivative useful as a medicine for mammals, which has an excellent antitumor activity and low toxicity.

It is another object of this invention to provide a process for producing the above-mentioned isoindole derivatives.

It is a further object of this invention to provide an antitumor agent comprising the above-mentioned isoindole derivatives.

Other objects and advantages of this invention will become apparent from the following description.

In the present specification, the following terms have the following definitions unless otherwise specified.

The term "halogen atom" means a fluorine, chlorine, bromine or iodine atom; the term "lower alkyl group" means a $C_{1-5}$alkyl group such as methyl, ethyl, n-propyl, isopropyl, n-butyl, sec-butyl, tert-butyl, pentyl or the like; the term "alkenyl group" means a $C_{2-22}$alkenyl group such as vinyl, allyl, butenyl, decenyl, hexadecenyl, heptadecenyl, octadecenyl or the like; the term "lower alkylene group" means a $C_{1-5}$alkylene group such as methylene, ethylene, propylene, trimethylene, tetramethylene, pentamethylene, 1-methyltrimethylene or the like; the term "aryl group" means a phenyl, tolyl or naphthyl group; the term "acyl group" means a $C_{1-6}$alkanoyl group such as formyl, acetyl, propionyl, butyryl, isobutyryl, valeryl, isovaleryl, pivaloyl, hexanoyl or the like or an aroyl group such as benzoyl, toluoyl, naphthoyl or the like; the term "acyloxy group" means an acyl—O— group; the term "cycloalkyl group" means a $C_{3-6}$cycloalkyl group such as cyclopropyl, cyclobutyl, cyclopentyl, cyclohexyl or the like; the term "lower alkoxy group" means a lower alkyl—O— group; the term "aryloxy group" means an aryl—O— group; the term "lower alkylthio group" means a lower alkyl—S— group; the term "aralkyl group" means an aryl-lower alkyl group; the term "lower alkylamino group" means a lower alkyl—NH— group; the term "di-lower alkylamino group" means a

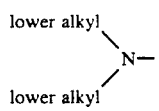

group; the term "lower alkyl-sulfonyloxy group" means a lower alkyl—SO$_3$— group; the term "arylsulfonyloxy group" means an aryl—SO$_3$— group; the term "lower alkoxysulfonyloxy group" means a lower alkyl—O—SO$_3$— group; the term "nitrogen-containing heterocyclic group" means a 5- or 6-membered nitrogen-containing heterocyclic group such as pyrrolidinyl, piperidinyl, piperazinyl, morpholinyl, triazolyl, tetrazolyl or the like; and the term "heterocyclic group" means a 5- or 6-membered heterocyclic group containing at least one hetero atom selected from oxygen, sulfur and nitrogen atoms such as pyrrolidinyl, piperidinyl, piperazinyl, morpholinyl, thienyl, furyl, pyrrolyl, pyrazolyl, pyridyl, pyridazinyl, pyrazinyl or the like; the term "heterocyclic carbonyloxy group" means a heterocyclic ring-COO- group; the term "trialkyl-ammonio group" means a tri-$C_{1-4}$alkylammonio group such as trimethylammonio, triethylammonio, dimethylethylammonio, diethylmethylammonio, tri-n-propylammonio, tributylammonio or the like; and the term "cyclic ammonio group" means a cyclic ammonio group such as pyridinio, pyridazinio, pyrimidinio, pyrazinio or the like.

The substituents of the substituted lower alkyl, alkenyl, lower alkylthio, cycloalkyl, aryl, aryloxy, carbamoyloxy, acyl, heterocyclic carbonyloxy or heterocyclic group in the definitions of $R^1$ and $R^3$; the substituents of the substituted lower alkyl, aryl, aralkyl, carbamoyl or acyl group in the definition of $R^2$; the substituents of the substituted lower alkyl, cycloalkyl, aralkyl, acyl or aryl group in the definitions of $R^4$ and $R^5$ and the substituents of the substituted nitrogen-containing heterocyclic group which $R^4$ and $R^5$ form with the nitrogen atom to which they are bonded include halogen atoms, lower alkyl groups, lower alkoxy groups, di-lower alkylamino groups, cycloalkyl groups, aryl groups, aralkyl groups, unprotected or protected hydroxyl groups and heterocyclic groups.

When each of $R^1$ to $R^5$ has a hydroxyl group, it may be protected with a usually known protective group.

The group represented by the formula:

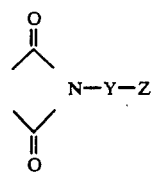

wherein Y and Z have the same meanings as defined above is bonded to the 2- and 3- or 3- and 4-positions of a carbazole skeleton or the 1- and 2- or 2- and 3-positions of a dibenzofuran or dibenzothiophen skeleton, and includes specifically the following groups:

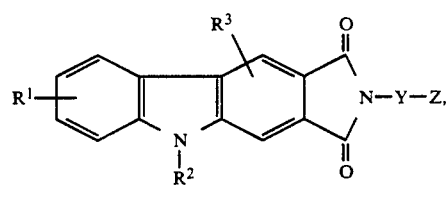

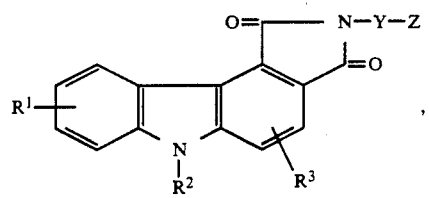

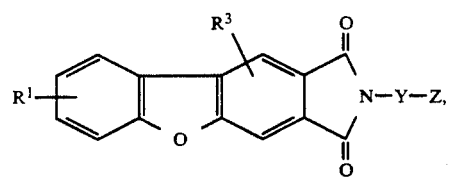

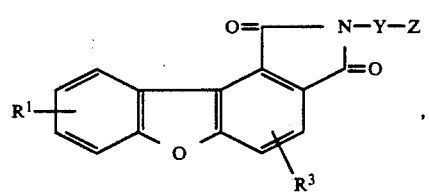

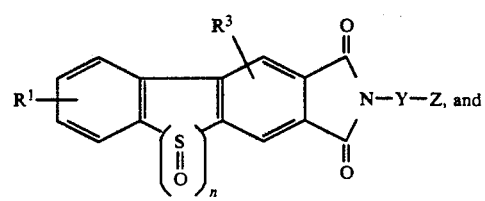

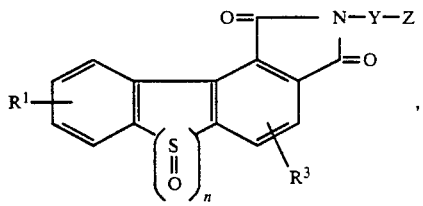

wherein $R^1$, $R^2$, $R^3$, Y, Z and n have the same meanings as defined above.

The protective groups of the protected amino, carboxyl and hydroxyl groups include commonly used protective groups, and specifically those described in Theodora W. Green, Protective Groups in Organic Synthesis, published by John Wiley & Sons, Inc., (1981), Japanese Patent Application Kokoku No. 52,755/85 and the like.

The salts of the isoindole derivatives of general formula [1] may be conventional salts at basic group such as amino group or the like or at acidic group such as hydroxyl or carboxyl group or the like.

The salts at basic group include, for example, salts with mineral acids such as hydrochloric acid, hydrobromic acid, sulfuric acid and the like; salts with organic carboxylic acids such as tartaric acid, formic acid, citric acid, trichloroacetic acid, trifluoroacetic acid and the like; salts with sulfonic acids such as methanesulfonic acid, benzenesulfonic acid, p-toluenesulfonic acid, mesitylenesulfonic acid, naphthalenesulfonic acid and the like; etc., and the salts at acidic groups include salts with alkali metals such as sodium, potassium and the like; salts with alkaline earth metals such as calcium, magnesium and the like; ammonium salts; salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like; etc.

When the isoindole derivative of general formula [1] has a trialkylammonio or cyclic ammonio group in its molecule, this group may form a salt with a halide anion, a lower alkylsulfonyloxy anion, or an unsubstituted or lower alkyl- or halogen-substituted arylsulfonyloxy anion, or the like.

Moreover, the isoindole derivative of general formula [1] and a salt thereof may form an inner salt.

When the isoindole derivative of general formula [1] or its salt has isomers (for example, optical isomer, geometric isomer, tautomeric isomer and the like), this invention includes all of the isomers. Moreover, this invention includes hydrates, solvates and various crystal forms thereof, too.

An explanation is made below of processes for producing the compound of this invention.

The isoindole derivatives of general formula [1] and their salts can be produced by processes known per se or their appropriate combinations, for example, according to the following production routes:

Production Process 1

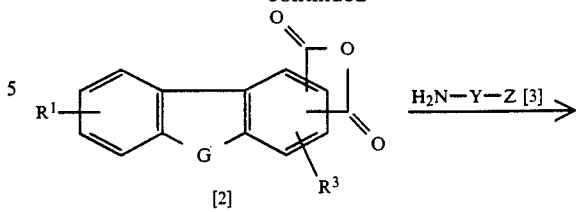

Production Process 2

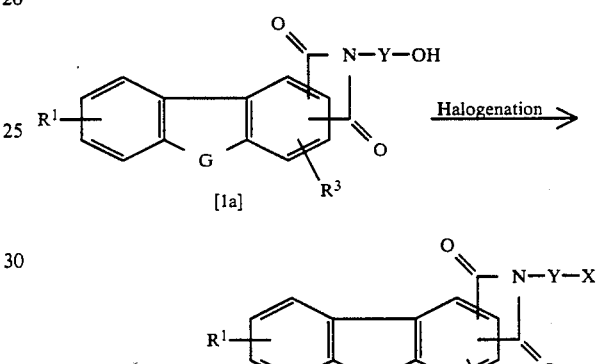

Production Process 3

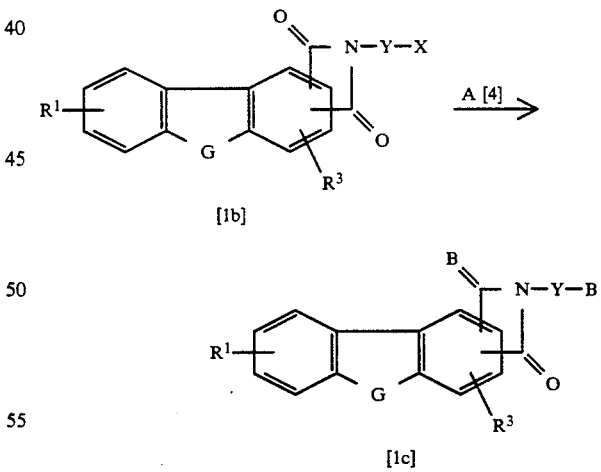

Production Process 4

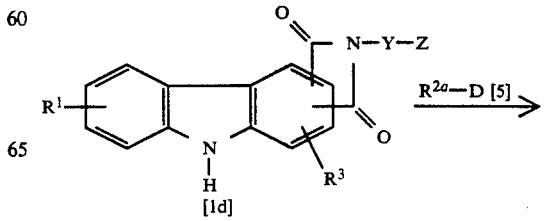

-continued

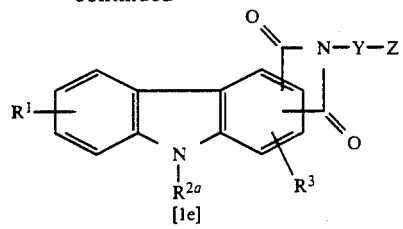
[1e]

Production Process 5

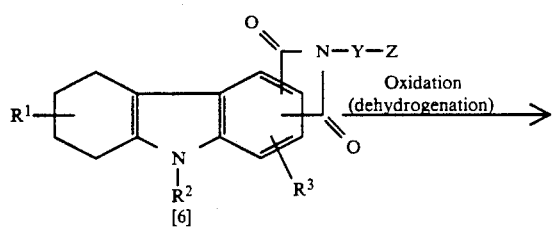

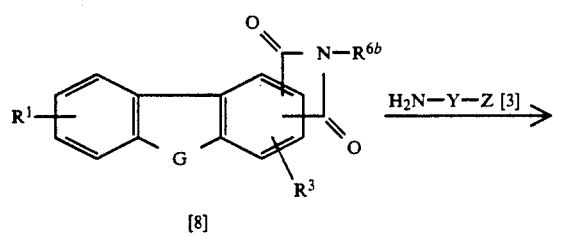
[1f]

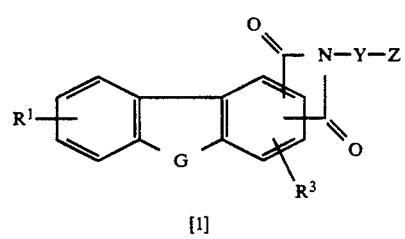
[1g]

Production Process 6

-continued

Production Process 7

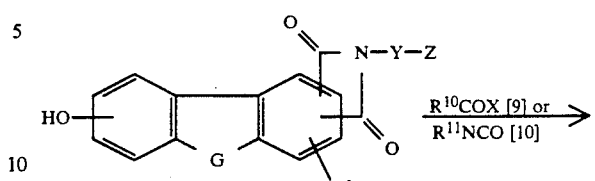
[1h]

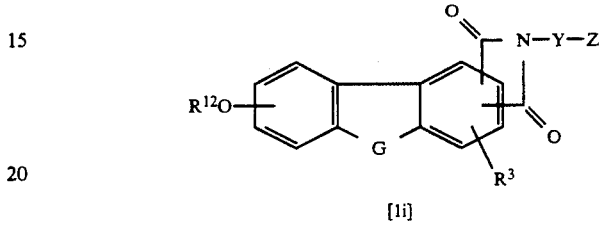
[1i]

where $R^1$, $R^2$, $R^3$, G, Y and Z have the same meanings as defined above, $G^1$ represents an oxygen or sulfur atom or a group of the formula,

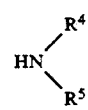

in which $R^2$ has the same meaning as defined above; $R^{2a}$ is the unsubstituted or substituted lower alkyl, aralkyl or acyl group mentioned in the definition of $R^2$; $R^{6b}$ represents the unsubstituted or substituted aryl group mentioned in the definition of $R^6$ stated hereinafter; $R^{10}$ represents an unsubstituted or substituted lower alkyl, alkenyl, cycloalkyl, aryl, aryloxy, aralkyl, lower alkylamino, di-lower alkylamino or heterocyclic group; $R^{11}$ represents an unsubstituted or substituted lower alkyl, alkenyl, cycloalkyl, aralkyl, aryl or chlorosulfonyl group; $R^{12}$ represents a group represented by the formula, $R^{10}$—CO— in which $R^{10}$ has the same meaning as defined above or the formula, $R^{11a}$—NHCO— in which $R^{11a}$ represents a hydrogen atom or the unsubstituted or substituted lower alkyl, alkenyl, cycloalkyl, aralkyl or aryl group mentioned in the definition of $R^{11}$; X represents a halogen atom; the compound represented by A is an amine or cyclic amine represented by the formula,

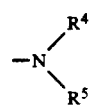

in which $R^4$ and $R^5$ have the same meanings as defined above or trialkylamine; B represents the same group of the formula, $$-N\begin{matrix}R^4\\R^5\end{matrix}$$

as mentioned in the definition of Z, in which formula $R^4$ and $R^5$ have the same meanings as defined above, or a trialkylammonio or cyclic ammonio group, D represents a removable group; and the broken line means that the bond between the two carbon atoms are a single or double bond.

The trialkylamine and the cyclic amine are, respectively, a trialkylamine capable of forming the trialkylammonio group explained as to Z and a cyclic amine capable of forming the cyclic ammonio group explained as to Z.

The removable group in the definition of D includes halogen atoms, acyloxy groups, arylsulfonyloxy groups, lower alkoxysulfonyloxy groups and the like which are usually known as removable groups.

The substituents of $R^{2a}$, $R^{6b}$, $R^{10}$, $R^{11}$ and $R^{11a}$ include those mentioned as to $R^1$ to $R^5$.

A more detailed explanation is made below of a process for producing the compound of general formula [1] according to the above-mentioned production route.

PRODUCTION PROCESS 1

A compound of general formula [1] is reacted with a compound of general formula [3] in the presence or absence of a solvent to obtain a compound of general formula [1]. This reaction is effected by per se known processes or their appropriate combinations, for example, according to the method described on pages 973-975 of Organic Syntheses, Col. Vol. V or a method similar thereto.

The solvent to be used in this reaction may be any solvent as far as it does not adversely affect the reaction, and includes, for example, aromatic hydrocarbons such as benzene, toluene, xylene and the like; halogenated hydrocarbons such as chloroform, methylene chloride, dichloroethane and the like. These solvents may be used alone or in admixture of two or more.

When the compound of general formula [3] is a salt with an inorganic or organic acid, the above reaction may be effected in the presence of a base.

The base which may be optionally used in the above reaction includes, for example, inorganic bases such as alkali hydrogencarbonates, alkali carbonates, alkali hydroxides and the like; organic bases such as triethylamine, tripropylamine, tributylamine and the like; etc.

The amount of the compound of general formula [3] to be used is at least equimolar to the compound of general formula [2], preferably 1.0-6.0 moles per mole of the compound of general formula [2].

When the base is used, the amount thereof is at least equimolar to the compound of general formula [2].

The reaction temperature and time are not critical; however, the reaction may be carried out at 20°-150° C. for 10 minutes to 10 hours.

PRODUCTION PROCESS 2

A compound of general formula [1b] can be obtained by reacting a compound of general formula [1a] with a halogenating agent such as carbon tetrabromidetriphenyl phosphine or the like in the presence or absence of a solvent.

The solvent to be used in this reaction may be any solvent as far as it does not adversely affect the reaction, and includes, for example, halogenated hydrocarbons such as methylene chloride, chloroform and the like; ethers such as tetrahydrofuran, dioxane and the like; nitriles such as acetonitrile, propionitrile and the like; amides such as N,N-dimethylformamide, N,N-dimethylacetamide and the like; phosphates such as triethyl phosphate and the like; pyridine; etc. These solvents may be used alone or in admixture of two or more.

The amount of the halogenating agent to be used is at least equimolar to the compound of the compound of general formula [1a], preferably 1.0-3.0 moles per mole of the compound of general formula [1a].

The reaction temperature and time are not critical; however, the reaction may be carried out at 0°-60° C. for 5 minutes to 10 hours.

PRODUCTION PROCESS 3

A compound of general formula [1c] can be obtained by reacting the compound of general formula [1b] with a compound of general formula [4] in the presence or absence of a solvent.

The solvent to be used in this reaction may be any solvent as far as it does not adversely affect the reaction, and includes, for example, halogenated hydrocarbons such as chloroform, methylene chloride, dichloroethane and the like; ethers such as tetrahydrofuran, dioxane and the like; aromatic hydrocarbons such as toluene, xylene and the like; nitriles such as acetonitrile, propionitrile and the like; amides such as N,N-dimethylformamide, N,N-dimethylacetamide and the like; phosphoramides such as hexamethylphosphoramide, and the like; sulfoxides such as dimethyl sulfoxide and the like; etc. These solvents may be used alone or in admixture of two or more. It may also be used as a solvent for the compound of general formula [4].

The amount of the compound of general formula [4] to be used is at least equimolar to the compound of general formula [1b].

The reaction temperature and time are not critical; however, the reaction may be carried out at 10°-130° C. for 30 minutes to 48 hours.

PRODUCTION PROCESS 4

A compound of general formula [1e] can be obtained by reacting a compound of general formula [1d] with a compound of general formula [5] in the presence or absence of a solvent.

The solvent to be used in this reaction may be any solvent as far as it does not adversely affect the reaction, and includes, for example, the solvents mentioned in Production Process 3.

The reaction can also be effected in the presence of a base. The base which may be used in the reaction includes, for example, the bases mentioned in Production Process 1 above, sodium hydride and the like.

The amount of the compound of general formula [5] to be used is at least equimolar to the compound of general formula [1d], preferably 1.0-3 moles per mole of the compound of general formula [1d].

When a base is used, the amount thereof may be at least equimolar to the compound of general formula [1d].

The reaction temperature and time are not critical; however, the reaction may be effected at 10°-140° C. for 10 minutes to 48 hours.

PRODUCTION PROCESS 5

Process For Producing Compounds of General Formulas [1f] and [1g]

A compound of general formula [1f] or [1g] can be obtained by oxidizing a compound of general formula [6] or [7] (dehydrogenation). These reactions are effected by processes known per se or their appropriate combinations, for example, according to the method described on pages 844-860 or 1088-1092 of Shin Jikken Kagaku Koza (New Experimental Chemistry Course), edited by Chemical Society of Japan published by Maruzen K. K., Vol. 15[I-2] or a method similar thereto.

Specifically, the above oxidation reaction may be effected using a dehydrogenating agent such as palladium-carbon, 2,3-dichloro-5,6-dicyano-p-benzoquinone, 2,3,5,6-tetrachloro-p-benzoquinone or the like.

The reaction temperature and time are not critical, and when palladium-carbon is used, the reaction may be carried out in a solvent such as cymene, decaline, cumene, diphenyl ether or the like at 150°-260° C. for 10 minutes to 48 hours.

When 2,3-dichloro-5,6-dicyano-p-benzoquinone or 2,3,5,6-tetrachloro-p-benzoquinone is used, it is used in an amount of at least 2 moles per mole of the compound of general formula [6] or [7] and the reaction may be carried out in a solvent, for example, an aromatic hydrocarbon such as benzene, toluene, xylene, chlorobenzene, tert-butylbenzene, dichlorobenzene or the like; a halogenated hdyrocarbon such as chloroform, methylene chloride or the like; an organic acid such as acetic acid or the like; an alcohol such as tert-butyl alcohol or the like at 10°-180° C. for 10 minutes to 48 hours.

And, the compound of general formula [lg] can be obtained by reacting the compound of general formula [7] with a halogen, for example, bromine, chlorine or the like.

The solvent to be used in this reaction may be any solvent as far as it does not adversely affect the reaction, and includes, for example, halogenated hydrocarbons such as carbon tetrachloride, chloroform, methylene chloride and the like. These solvents may be used alone or in admixture of two or more.

The amount of halogen to be used is at least 2 moles per mole of the compound of general formula [7].

The reaction temperature and time are not critical; however, the reaction may be carried out at 0°-80° C. for 10 minutes to 48 hours.

PRODUCTION PROCESS 6

The compound of general formula [1] can also be produced by reacting a compound of general formula [8] with the compound of general formula [3] in the presence or absence of a solvent.

The solvent used in this reaction may be any solvent as far as it does not adversely affect the reaction, and includes, for example, aromatic hydrocarbons such as benzene, toluene, xylene and the like; ethers such as tetrahydrofuran, dioxane and the like; amides such as N,N-dimethylformamide, N,N-dimethylacetamide and the like; phosphoramides such as hexamethylphosphoramide and the like; sulfoxides such as dimethylsulfoxide; pyridine; and the like. These solvents may be used alone or in admixture of two or more. The compound of general formula [3] may also be used as a solvent.

The amount of the compound of general formula [3] to be used is at least equimoalr to the compound of general formula [8], preferably 1.0-20 moles per mole of the compound of general formula [8].

The reaction temperature and time are not critical; however, the reaction may be carried out at 50°-150° C. for 10 minutes to 10 hours.

Production Process 7

A compound of general formula [Ii] can be obtained by reacting a compound of general formula [Ih] with a compound of general formula [9] or [10] in the presence or absence of a solvent.

The solvent to be used in this reaction may be any solvent as far as it does not adversely affect the reaction, and includes, for example, the solvents mentioned in Production Process 2 above.

The above reaction may also be effected in the presence of a base, and the base includes, for example, organic bases such as triethylamine, tripropylamine, tributylamine, pyridine and the like.

When the compound of general formula [10] is subjected to the above reaction, the reaction may be effected in the presence of a Lewis acid such as aluminum chloride, dibutyltin diacetate or the like.

The amount of the compound of general formula [9] or [10] used is at least equimolar to the compound of general formula [Ih], preferably 1.0-10 moles, per mole of the compound of general formula [Ih].

The reaction temperature and time are not critical; however, the reaction may be carried out at 20°-150° C. for 10 minutes to 10 hours.

When the above-mentioned compounds can form their salts, the salts may be used, and the above explanation of the salt of compound of general formula [1] can be applied thereto.

Next, an explanation is made below of processes for producing the compounds of general formulas [2], [6], [7] and [8] which are the starting materials for producing the compound of this invention.

These compounds can be produced by processes known per se or their appropriate combinations, for example, according to the following production routes:

Production Process a

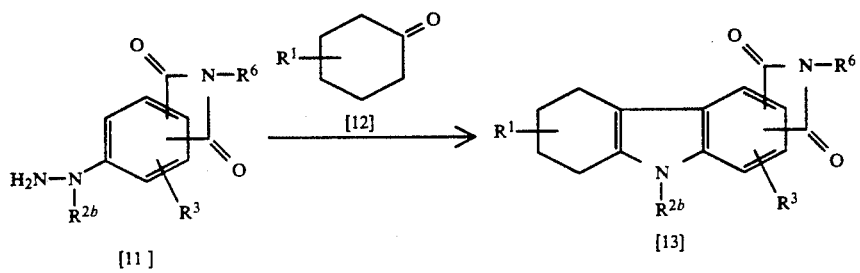

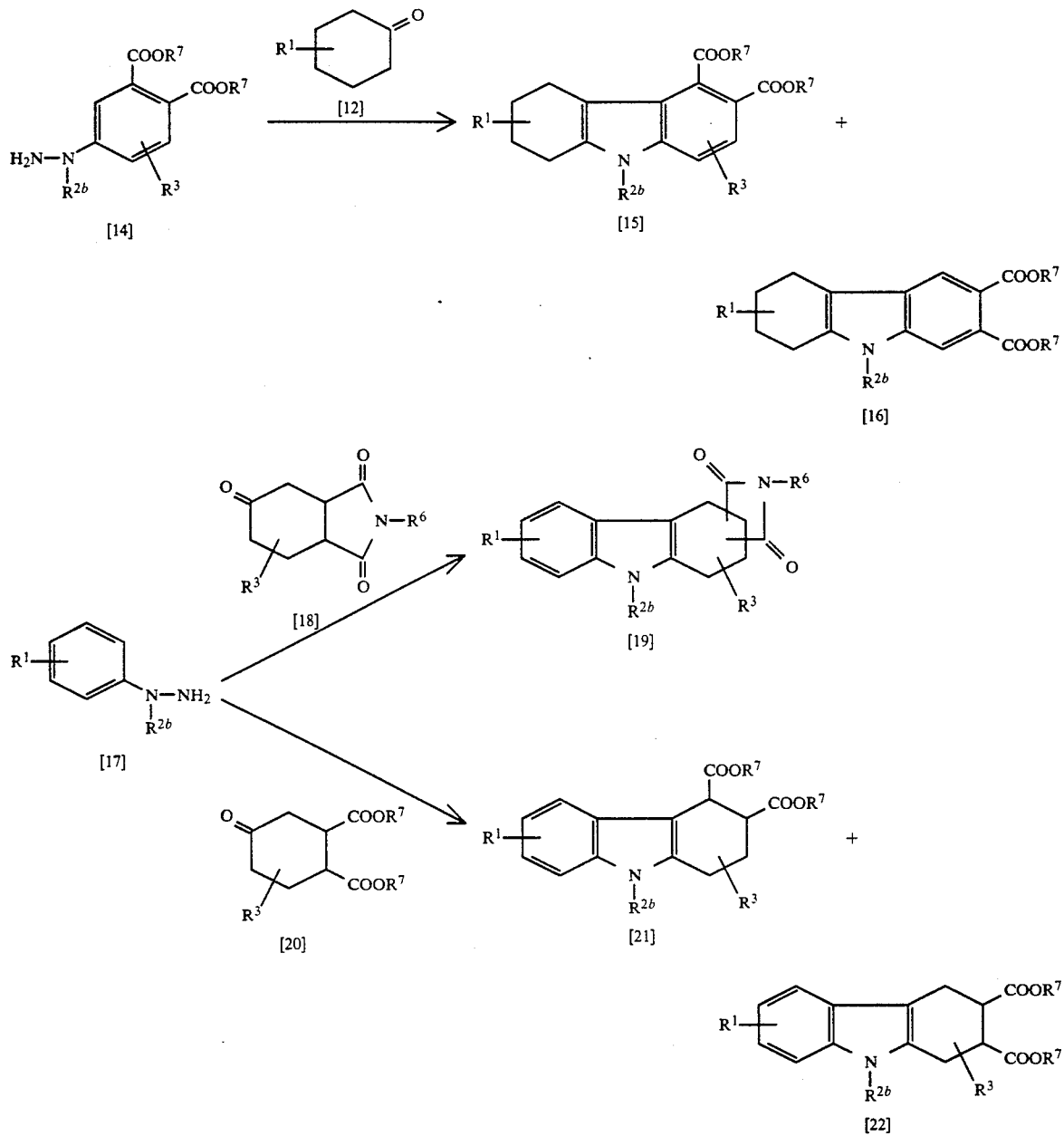
Production Process b
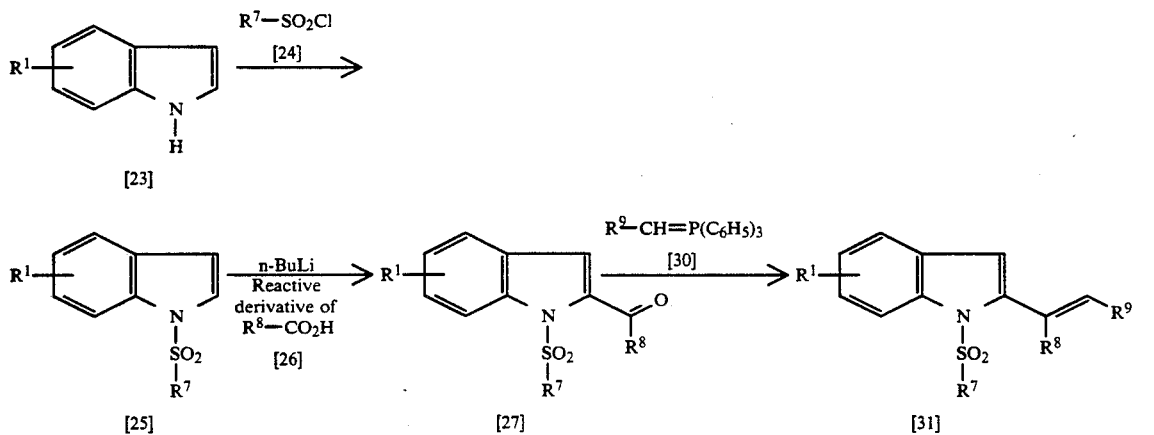

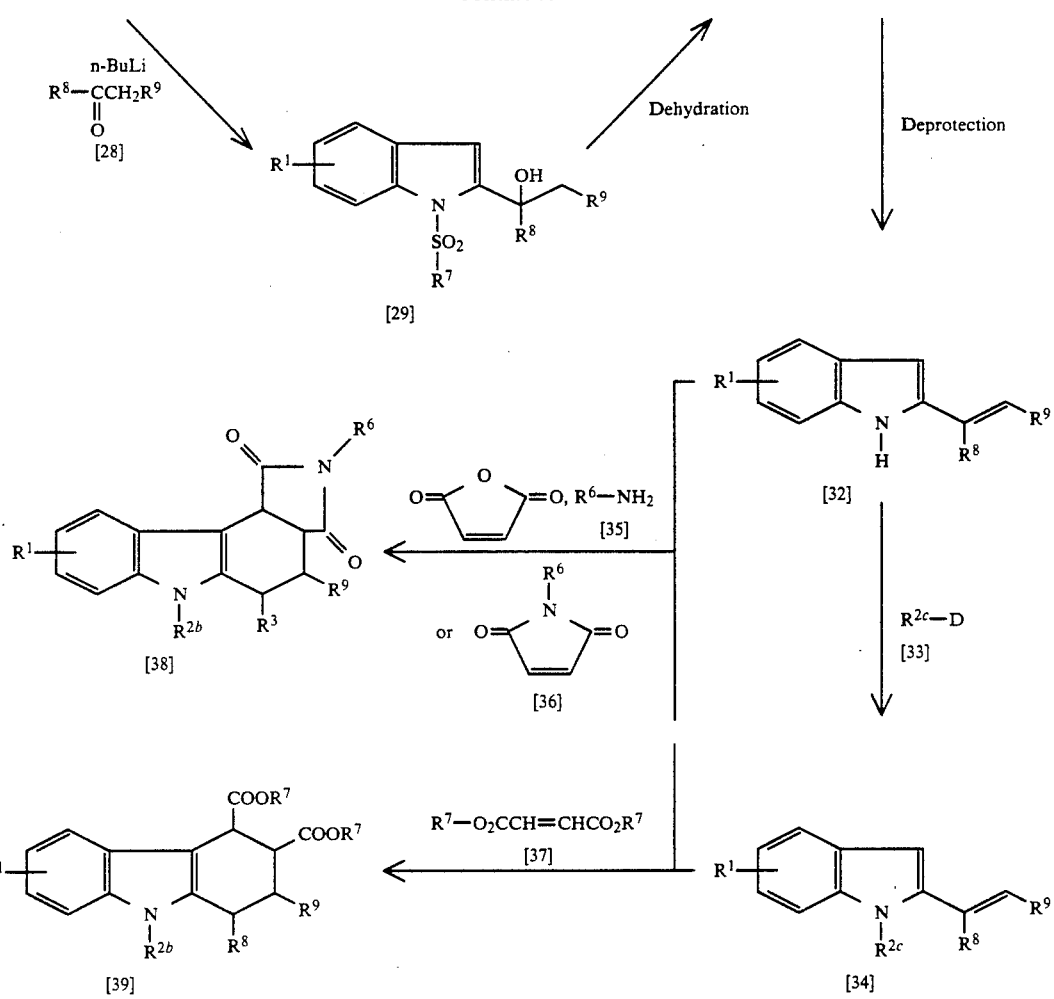
Production Process c
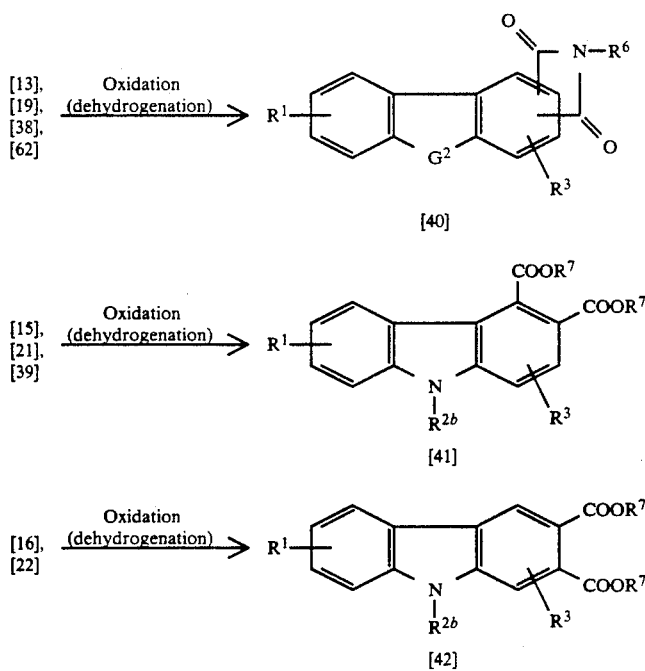

Production Process d
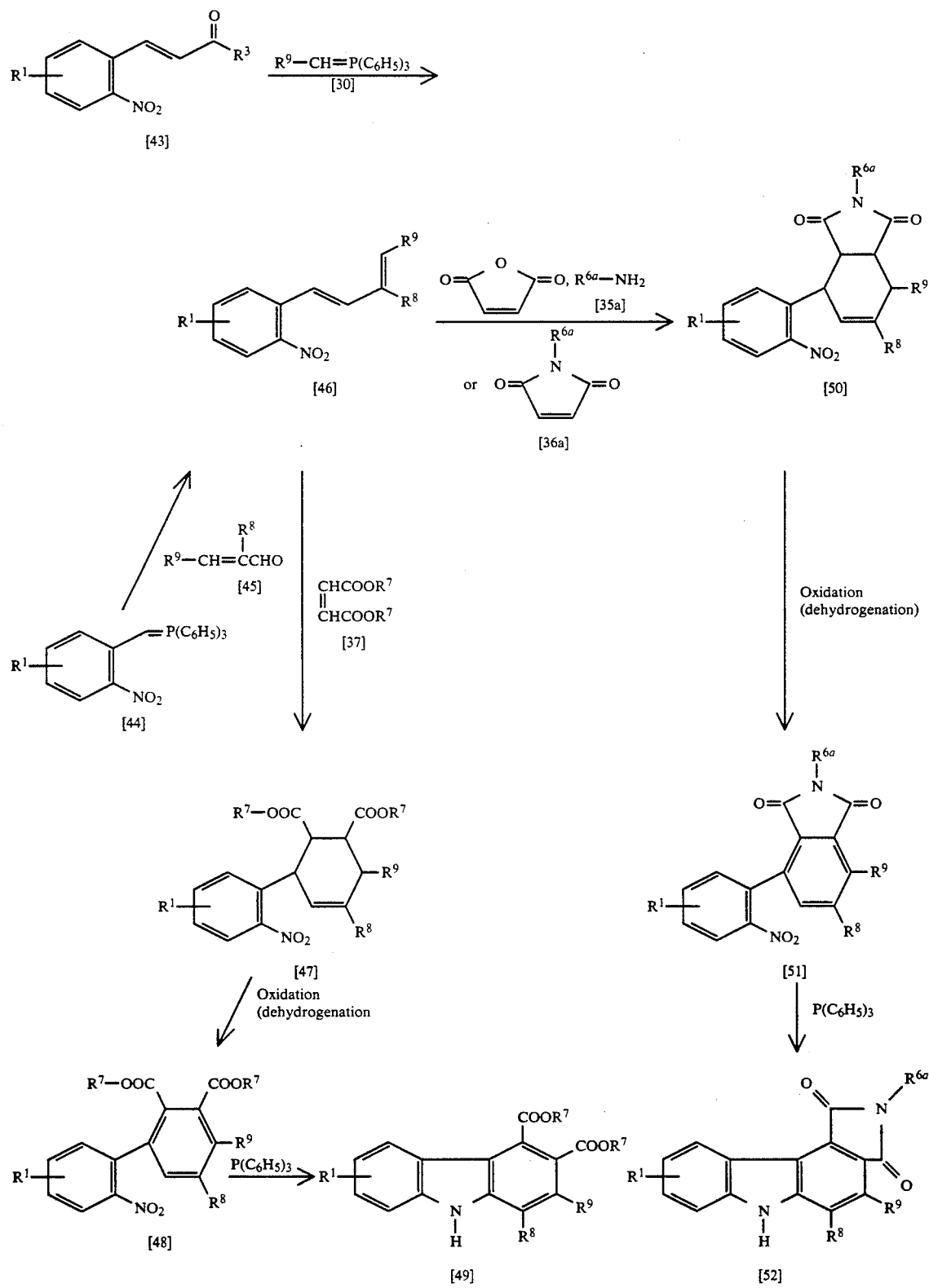
Production Process e

-continued

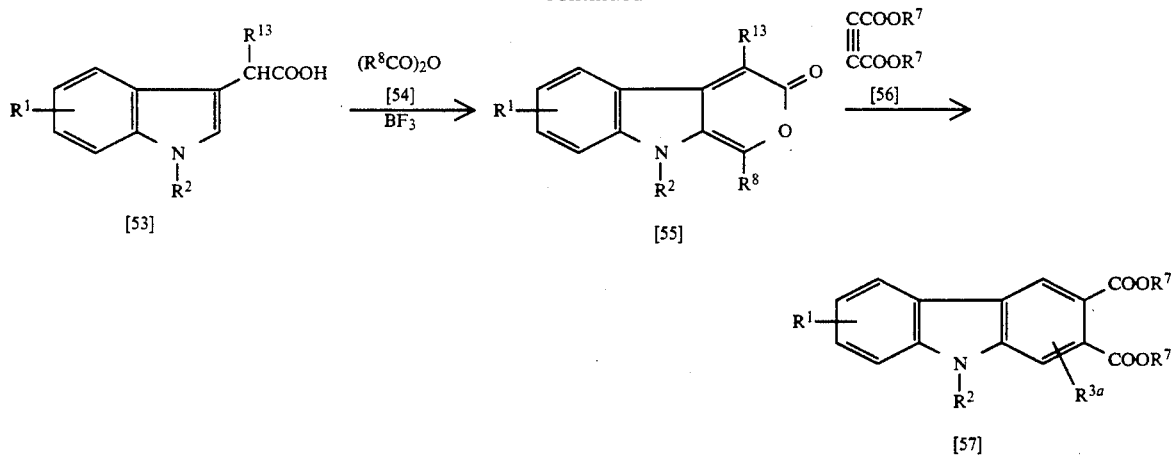

Production Process f

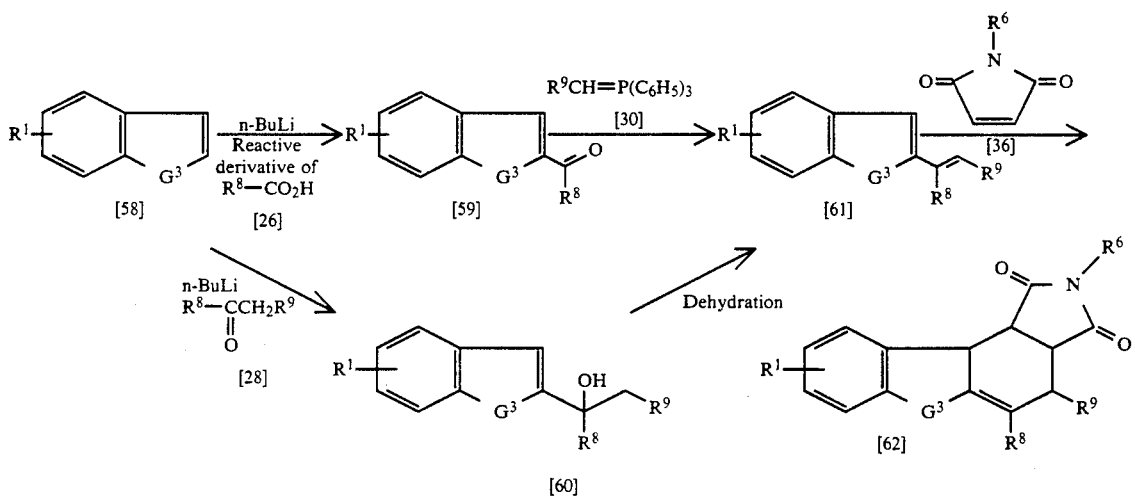

Production Process g

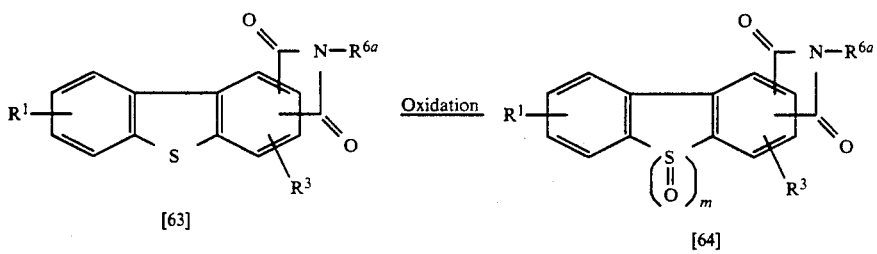

Production Process h

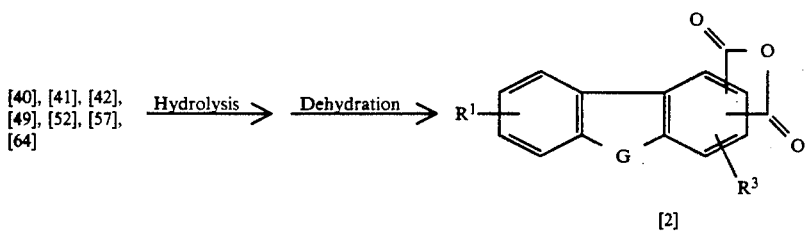

wherein $R^1$, $R^2$, $R^3$, G and D have the same meanings as defined above, $R^{2b}$ represents a hydrogen atom or the unsubstituted or substituted lower alkyl, aryl or aralkyl group mentioned in the definition of $R^2$, $R^{2c}$ represents the unsubstituted or substituted lower alkyl or aralkyl group mentioned in the definition of $R^2$, $R^{3a}$ represents a hydrogen atom or the unsubstituted or substituted lower alkyl, alkenyl or aryl group mentioned in the definition of $R^3$, $R^6$ represents an unsubstituted or substituted lower alkyl, aralkyl or aryl group or a group represented by the formula, —Y—Z in which Y and Z have the same meanings as defined above, $R^{6a}$ represents an unsubstituted or substituted lower alkyl, aralkyl or aryl group, $R^7$ represents an unsubstituted or substituted lower alkyl, aralkyl or aryl group, $R^8$ and $R^{13}$ represent hydrogen atoms, unsubstituted or substituted lower alkyl, alkenyl or aryl groups, $R^9$ represents a hydrogen atom, an unsubstituted or substituted lower alkyl, alkenyl or aryl group or an unprotected or protected hydroxyl or carboxyl group, $G^2$ represents an oxygen or sulfur atom or a group of the formula,

in which $R^{2b}$ has the same meaning as defined above, $G^3$ represents an oxygen or sulfur atom, and m represents 1 or 2.

The substituents of $R^{2b}$, $R^{2c}$, $R^{3a}$, $R^6$, $R^{6a}$, $R^7$, $R^8$, $R^9$, and $R^{13}$ include those mentioned in the definitions of $R^1$ to $R^5$.

The reactive derivatives of the carboxylic acid of general formula [26] include symmetric acid anhydrides, mixed acid anhydrides, acid halides, active amides and the like.

A more detailed explanation is made below of processes for producing the compounds of general formulas [2], [6] (including [13]), [7] (including [19], [38] and [62]) and [8] (including [40], [52], [63] and [64]) according to the above-mentioned production routes.

PRODUCTION PROCESS A

Process For Producing Compounds of General Formulas [13], [15], [16], [19], [21] and [22]

A compound of general formula [11] is reacted with a compound of general formula [12] to obtain a corresponding compound of general formula [13], a compound of general formula [14] is reacted with a compound of general formula [12] to obtain a compound of general formula [15] or [16], a compound of general formula [17] is reacted with a compound of general formula [18] to obtain a compound of general formula [19], and a compound of general formula [17] is reacted with a compound of general formula [20] to obtain a compound of general formula [21] or [22]. This reaction is generally called "Fisher's Indole synthesis" and is effected, for example, according to the process described on pages 1957-1960 of Shin Jikken Kagaku Koza (New Experimental Chemistry Course), edited by Chemical Society of Japan published by Maruzen K. K., Vol. 14[IV] or a process similar thereto.

PRODUCTION PROCESS B

Process For Producing Compounds of General Formulas [38] and [39]

First of all, a compound of general formula [27] is obtained by reacting a compound of general formula [23] with a compound of general formula [24] (sulfonylation) to obtain a compound of general formula [25] followed by reaction with a reactive derivative of a carboxylic acid of general formula [26] and n-butyllithium.

In the above reactions, the reactive derivative of the carboxylic acid of general formula [26] may be replaced by a compound represented by the formula, $R^8$-CN in which $R^8$ has the same meaning as defined above or N,N-dimethylformamide.

Subsequently, a compound of general formula [27] is subjected to reaction with a compound of general formula [30] (the Wittig reaction) to obtain a compound of general formula [31] or a compound of general formula [25] is reacted with a compound of general formula [28] and n-butyllithium to obtain a compound of general formula [29], and then, the compound of general formula [29] is subjected to dehydration to obtain a compound of general formula [31].

Subsequently, the compound of general formula [31] is subjected to removal of protective group (removal of sulfonyl group) to obtain a compound of general formula [32].

Incidentally, in the compounds of general formulas [25], [27], [29] and [31], the group of the formula, $-SO_2R^7$ in which $R^7$ has the same meaning as defined above may be replaced by a protective group usually used as a protective group for the imino group of indole ring, an alkyl group or the like.

The compounds of general formulas [27] and [29] may be subjected to reaction with a compound of general formula [30] and dehydration reaction after the removal of protective group.

Subsequently, the compound of general formula [32] is reacted with a compound of general formula [33] to obtain a compound of general formula [34] in which a $R^{2c}$ (in which $R^{2c}$ has the same meaning as defined above) group has been introduced at the nitrogen atom of indole ring.

Then, the compound of general formula [32] or [34] is reacted with maleic anhydride, and then with an amine of general formula [35] or subjected to reaction with a compound of general formula [36] (the Diels-Alder reaction), to obtain a compound of general formula [38].

Also, a compound of general formula [39] can be obtained by subjecting the compound of general formula [32] or [34] to reaction with a compound of general formula [37] (the Diels-Alder reaction).

When the group of the formula, $-SO_2R^7$ in which $R^7$ has the same meaning as defined above, of the compound of general formula [31] is replace by an alkoxymethyl group such as methoxymethyl or the like or an aralkyl group such as benzyl or the like which are some examples of the protective groups usually employed as a protective group for the imino group of indole ring or when the imino group of indole ring is an alkylimino group, the compound of general formula [31] can as such be subjected to reaction with maleic anhydride and then with an amine of general formula [35], or subjected to reaction with a compound of general formula [36] or [37] to obtain a compound of general formula [38] or [39] without being converted to the compound of general formula [32] or [34].

Each of the above-mentioned reactions can be effected in a manner known per se; however, it can be effected according to the method described in, for example, J. Org. Chem., Vol. 38, pages 3324-3330 (1973), J. Org. Chem., Vol. 49, pages 5006-5008 (1984), J. Org. Chem., Vol. 36, pages 1759-1764 (1965), Organic Reactions, Vol. 14, Chapter 3, Synthesis, pages 461-462 (1981) or the like.

PRODUCTION PROCESS C

Process for producing compounds of general formulas [40], [41] and [42]

A compound of general formula [40], [41] or [42] can be obtained by oxidizing the compound of general formula [13], [15], [16], [19], [21], [22], [38], [39] or [62] (dehydrogenation). These reactions are effected by processes known per se or their appropriate combinations, for exmaple, according to the method described in Shin Jikken Kagaku Koza (New Experimental Chemistry Course), Vol. 15[I-2], pages 844–860 or 1088–1092 or a method similar thereto.

And, the compound of general formula [40], [41] or [42] can be obtained by reacting the compound of general formula [19], [21], [22], [38], [39] or [62] with a halogen, for example, bromine, chlorine or the like.

The solvent to be used in this reaction may be any solvent as far as it does not adversely affect the reaction, and includes, for example, halogenated hydrocarbons such as carbon tetrachloride, chloroform, methylene chloride and the like. These solvents may be used alone or in admixture of two or more.

The amount of halogen to be used is at least 2 moles per mole of the compound of general formula [19], [21], [22], [38], [39] or [62].

The reaction temperature and time are not critical; however, the reaction may be carried out at 0°–80° C. for 10 minutes to 48 hours.

PRODUCTION PROCESS D

Process For Producing Compounds of General Formulas [49] and [52]

A compound of general formula [46] can be obtained by reacting a compound of general formula [43] with a compound of general formula [30] or reacting a compound of general formula [44] with a compound of general formula [45]. This reaction is effected by processes known per se or their appropriate combinations, for example, according to the method described in Organic Reactions, Vol. 14, Chapter 3 or a method similar thereto.

Subsequently, a compound of general formula [46] is subjected to reaction with maleic anhydride followed by reaction with a compound of general formula [35a], or a compound of general formula [46] is subjected to reaction with a compound of general formula [36a] to obtain a compound of general formula [50].

And a compound of general formula [46] is subjected to reaction with a compound of general formula [37] to obtain a compound of general formula [47]. This reaction is effected by processes known per se or their appropriate combinations, for example, according to the method described in Organic Reactions, Vol. 4, Chapters 1 and 2 or a method similar thereto.

Subsequently, the compound of general formula [47] or [50] is subjected to oxidation to obtain a compound of general formula [48] or [51] (dehydrogenation).

These reactions are effected by processes known per se or their appropriate combinations, for example, according to the method described in Shin Jikken Kagaku Koza (New Experimental Chemistry Course), Vol. 15[I-2], pages 844–860 or 1088–1092 or a method similar thereto.

Further, the compound of general formula [48] or [51] is subjected to reaction with triphenylphosphine to obtain a corresponding compound of general formula [49] or [52].

These reactions are effected by processes known per se or their appripriate combinations, for example, according to the method described in J.I.G. Cadogan, "Organophosphorous Reagents in Organic Synthesis", Academic Press, New York (1979), page 272 or a method similar thereto.

PRODUCTION PROCESS E

Process For Producing a Compound of General Formula [57]

A compound of general formula [53] is subjected to reaction with a compound of general formula [54] in the presence of boron trifluoride to obtain a compound of general formula [55]. This reaction is effected by processes known per se or their appropriate combinations, for example, according to the method described in Chem. Ber., Vol. 97, pages 667–681 (1964) or a method similar thereto.

Subsequently, the compound of general formula [55] is subjected to reaction with a compound of general formula [56] to obtain a compound of general formula [57]. This reaction is effected by processes known per se or their appropriate combinations, for example, according to the method described in J. Chem. Soc., Perkin Trans. I, pages 2505–2508 (1985) or a method similar thereto.

PRODUCTION PROCESS F

Process For Producing a Compound of General Formula [62]

A compound of general formula [59] can be obtained by reacting a compound of general formula [58] with a reactive derivative of the carboxylic acid of general formula [26] and n-butyllithium.

Subsequently, the compound of general formula [59] is subjected to reaction with a compound of general formula [30] (the Wittig reaction) to obtain a compound of general formula [61], or the compound of general formula [58] is reacted with the compound of general formula [28] and n-butyllithium to obtain a compound of general formula [60] followed by dehydration thereof to obtain a compound of general formula [61].

Subsequently, the compound of general formula [61] is subjected to reaction with the compound of general formula [36] (the Diels-Alder reaction) to obtain a compound of general formula [62].

Each of the above-mentioned reactions can be effected in a manner known per se or their appropriate combiantions, and can also be effected according to the method described in, for example, An Introduction to the Chemistry of Heterocyclic Compounds, John Wiley & Sons, Inc., pages 216–224, Australian Journal of Chemistry, Vol. 26, pages 1093–1109 (1973) and Vol. 28, pages 1059–1081 (1975), Organic Reactions, Vol. 14, Chapter 3 or the like.

PRODUCTION PROCESS G

A compound of general formula [64] can be obtained by oxidizing a compound of general formula [63].

This reaction is effected by processes known per se or their appropriate combinations, for example, according to the method described in Shin Jikken Kagaku Koza (New Experimental Chemistry Course), Vol. 14[III], pages 1749–1752 and 1760–1761 or a method similar thereto.

PRODUCTION PROCESS H

A compound of general formula [2] can be obtained by hydrolyzing the compound of general formula [40], [41], [42], [49], [52], [57] or [64] and then dehydrating the product with acetic anhydride or the like.

This reaction is effected by processes known per se or their appropriate combinations, for example, according to the method described in Organic Syntheses, Col. Vol. II, pages 457–458 and Col. Vol. I, page 410 or a method similar thereto.

When the starting materials explained above, namely, the compounds of general formulas [2] to [64] can form their salts, the salts may be used instead thereof, and the explanation of the salt of the compound of general formula [1] can be applied thereto.

The compound of this invention (general formula [1]) thus obtained and the starting compounds thus obtained can be converted to other compounds falling within the scope of the same general formulas by being subjected to reactions known per se such as oxidation, reduction, rearrangement, substitution, acylation, halogenation, alkylation, imide-exchange, quaternization, deprotection, dehydration and hydrolysis or appropriate combinations of them.

When the compound of this invention (general formula [1]) and the starting compounds in the above-mentioned production processes have isomers (for example, optical isomer, geometric isomer, tautomeric isomer and the like), all of the isomers can be used and also, solvates, hydrates and all crystal forms of the compounds can be used.

When the compound of this invention (general formula [1]) and the starting compounds in the above-mentioned production processes have amino, hydroxyl or carboxyl groups, these groups may previously protected with a protective group and, after the reaction, if necessary, the protective group may be removed by the method known per se.

After the termination of the reaction, the reaction mixtures may be used as they are without being subjected to isolation.

The compounds of this invention (general formula [1]) thus obtained and the starting compounds thus obtained can be isolated and purified by a conventional method such as extraction, column chromatography, distillation, recrystallization or the like.

When the compound of this invention (general formula [1]) is used as a drug, the compound can be orally or parenterally administered as it is or in admixture of a pharmaceutically acceptable additive, such as excipient, carrier, diluent or the like in the form of a tablet, capsule, diluent or the like in the form of a tablet, capsule, granule, powder, injection, suppository or the like. The dose of the compound is administered in one portion or several portions. However, the dose may be selected depending upon the age, weight and symptom of a patient.

Next, the pharmacological activities of the representative compounds of this invention are explained.

The test compounds used were shown in Table 1a and Table 1b.

In the tables, the numerals in $R^1$ and $R^2$ columns each represent a substitution site of substituent in carbazole skeleton, 1H-benzofuro[3,2-e]isoindole skeleton or 1H-[1] benzothieno[3,2-e] isoindole skeleton.

The following abbreviations used in Table 1a and Table 1b have the following meanings:

Me: methyl group, Et: ethyl group, Pr: n-propyl group, i-Pr: isopropyl group, Bu: n-butyl group, t-Bu: tert-butyl group, Ph: phenyl group, Ac: acetyl group.

$R^1$, $R^2$, $R^3$, G, Y and Z in Tables 1a and 1b refer to the respective substituents in the following formula for the test compounds:

TABLE 1a

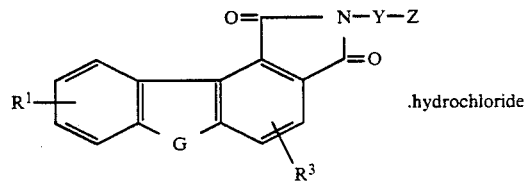
.hydrochloride

| Compound No. | $R^1$ | —G— | $R^3$ | —Y—Z |
|---|---|---|---|---|
| 1 | H | \NH/ | H | —CH₂CH₂NMe₂ |
| 2 | H | \NH/ | 1- Me | —CH₂CH₂NMe₂ |
| 3 | H | \NH/ | 2- Me | —CH₂CH₂NMe₂ |
| 4 | H | \NH/ | 2- Et | —CH₂CH₂NMe₂ |

TABLE 1a-continued
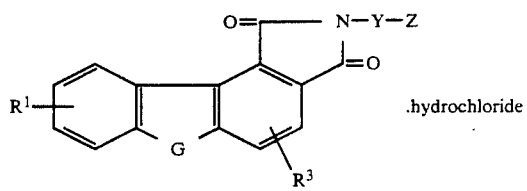
.hydrochloride
| Compound No. | R¹ | —G— | R³ | —Y—Z |
|---|---|---|---|---|
| 5 | H | \NH/ | 1,2- diMe | —CH$_2$CH$_2$NMe$_2$ |
| 6 | H | \NMe/ | 1- Me | —CH$_2$CH$_2$NMe$_2$ |
| 7 | H | \NH/ | 1- Ph | —CH$_2$CH$_2$NMe$_2$ |
| 8 | 7- Cl | \NH/ | H | —CH$_2$CH$_2$NMe$_2$ |
| 9 | 6- Cl | \NH/ | H | —CH$_2$CH$_2$NMe$_2$ |
| 10 | 6- Cl | \NMe/ | H | —CH$_2$CH$_2$NMe$_2$ |
| 11 | 6- F | \NH/ | H | —CH$_2$CH$_2$NMe$_2$ |
| 12 | 6- Me | \NH/ | H | —CH$_2$CH$_2$NMe$_2$ |
| 13 | 8- MeO— | \NH/ | H | —CH$_2$CH$_2$NMe$_2$ |
| 14 | 7- MeO— | \NH/ | H | —CH$_2$CH$_2$NMe$_2$ |
| 15 | 6- MeO— | \NH/ | H | —CH$_2$CH$_2$NMe$_2$ |
| 16 | 6- MeO— | \NH/ | 1- Me | —CH$_2$CH$_2$NMe$_2$ |

TABLE 1a-continued
.hydrochloride
| Compound No. | R¹ | —G— | R³ | —Y—Z |
|---|---|---|---|---|
| 17 | 6-MeO— | >NH/ | 2-Me | —CH$_2$CH$_2$NMe$_2$ |
| 18 | 7-MeO— | >NH/ | 1-Me | —CH$_2$CH$_2$NMe$_2$ |
| 19 | 6-MeO— | >NMe/ | H | —CH$_2$CH$_2$NMe$_2$ |
| 20 | 6-MeO— | >NEt/ | H | —CH$_2$CH$_2$NMe$_2$ |
| 21 | 6-MeO— | >NAc/ | H | —CH$_2$CH$_2$NMe$_2$ |
| 22 | 6,7-OCH$_2$O | >NH/ | H | —CH$_2$CH$_2$NMe$_2$ |
| 23 | 6-HO— | >NH/ | H | —CH$_2$CH$_2$NMe$_2$ |
| 24 | 6-HO— | >NH/ | 1-Me | —CH$_2$CH$_2$NMe$_2$ |
| 25 | 6-HO— | >NH/ | 2-Me | —CH$_2$CH$_2$NMe$_2$ |
| 26 | 6-HO— | >NH/ | 1,2-diMe | —CH$_2$CH$_2$NMe$_2$ |
| 27 | 6-HO— | >NH/ | 1-Ph | —CH$_2$CH$_2$NMe$_2$ |
| 28 | 7-HO— | >NH/ | H | —CH$_2$CH$_2$NMe$_2$ |

TABLE 1a-continued
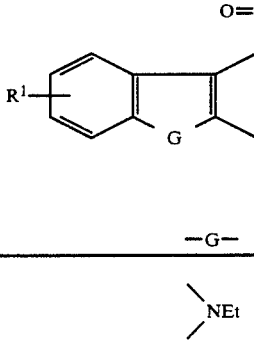
.hydrochloride
| Compound No. | R¹ | —G— | R³ | —Y—Z |
|---|---|---|---|---|
| 29 | 6-HO— | \NEt/ | H | —CH$_2$CH$_2$NMe$_2$ |
| 30 | 6-HO— | \NMe/ | H | —CH$_2$CH$_2$NMe$_2$ |
| 31 | 6,7-diHO— | \NH/ | H | —CH$_2$CH$_2$NMe$_2$ |
| 32 | 6-HO— | \NH/ | 1-Cl | —CH$_2$CH$_2$NMe$_2$ |
| 33 | 6-HO— | \NH/ | H |  |
| 34 | 6-MeO— | \NH/ | H |  |
| 35 | 6-HO— | \NH/ | 2-HO— | —CH$_2$CH$_2$NMe$_2$ |
| 36 | 6-MeO— | \NH/ | 2-MeO— | —CH$_2$CH$_2$NMe$_2$ |
| 37 | 6-PhCH$_2$O— | \NH/ | 1-MeO— | —CH$_2$CH$_2$NMe$_2$ |
| 38 | 6-HO— | \NH/ | 1-MeO— | —CH$_2$CH$_2$NMe$_2$ |
| 39 | 6-HO— | \NH/ | 1-Et | —CH$_2$CH$_2$NMe$_2$ |
| 40 | 6-MeO— | \NH/ | 1-MeO— | —CH$_2$CH$_2$NMe$_2$ |

TABLE 1a-continued
.hydrochloride
| Compound No. | R¹ | —G— | R³ | —Y—Z |
|---|---|---|---|---|
| 41 | 6- HO— | >NH | 1- HO— | —CH$_2$CH$_2$NMe$_2$ |
| 42 | 6- HO— | >NH | 1- Me | —CH$_2$CH$_2$NEt$_2$ |
| 43 | H | —O— | 5- Me | —CH$_2$CH$_2$NMe$_2$ |
| 44 | 6- N—COO— | >NH | 1- Me | —CH$_2$CH$_2$NMe$_2$ |
| 45 | 6- AcO— | >NH | 1- Me | —CH$_2$CH$_2$NMe$_2$ |
| 46 | 6- HO—, 8- Me | >NH | H | —CH$_2$CH$_2$NMe$_2$ |
| 47 | H | —S— | 5- Me | —CH$_2$CH$_2$NMe$_2$ |
| 48 | H | >SO$_2$ | 5- Me | —CH$_2$CH$_2$NMe$_2$ |
| 49 | 6- HO— | >NH | 1- 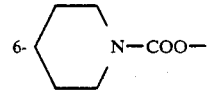 | —CH$_2$CH$_2$NMe$_2$ |
| 50 | 6- ON—COO— | >NH | 1- Me | —CH$_2$CH$_2$NMe$_2$ |
| 51 | 6- HO— | >NH | 1- Pr | —CH$_2$CH$_2$NMe$_2$ |
| 52 | 6- HO— | >NH | 1- i-Pr | —CH$_2$CH$_2$NMe$_2$ |
| 53 | 6- HO— | >NH | 1- Me | —CH$_2$CH$_2$N(i-Pr)$_2$ |

TABLE 1a-continued

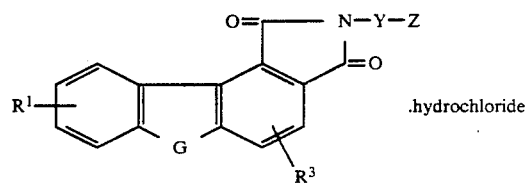

.hydrochloride

| Compound No. | R¹ | —G— | R³ | —Y—Z |
|---|---|---|---|---|
| 54 | 6- HO— | >NH / | 1- t-Bu | —CH$_2$CH$_2$NMe$_2$ |
| 55 | 6- [piperidine-N-piperidine-N—COO—] | >NH / | 1- Me | —CH$_2$CH$_2$NMe$_2$ |
| 56 | 9- MeO— | —S— | 5- Me | —CH$_2$CH$_2$NMe$_2$ |
| 57 | 6- HO | >NH / | 1- MeOCH$_2$— | —CH$_2$CH$_2$NMe$_2$ |
| 58 | 6- MeO— | >NH / | 1- cyclobutyl | —CH$_2$CH$_2$NMe$_2$ |
| 59 | 6- HO— | >NH / | 1- cyclobutyl | —CH$_2$CH$_2$NMe$_2$ |
| 60 | 6- HO— | >NH / | 1- Bu | —CH$_2$CH$_2$NMe$_2$ |
| 61 | 9- HO— | —S— | 5- Me | —CH$_2$CH$_2$NMe$_2$ |
| 62 | 9- HO— | —S— | 5- Me | —CH$_2$CH$_2$NEt$_2$ |
| 63 | 6- HO— | >NH / | 1- cyclohexyl | —CH$_2$CH$_2$NMe$_2$ |
| 64 | 6- MeO— | >NH / | 1- Me | —CH$_2$CH$_2$NHMe |
| 65 | 6- MeO— | >NH / | 1- Me | —CH$_2$CH$_2$NH$_2$ |
| 66 | H | —S— | H | —CH$_2$CH$_2$NMe$_2$ |
| 67 | 6- HO— | >NH / | 1- F$_3$C— | —CH$_2$CH$_2$NMe$_2$ |
| 68 | 6- HO— | >NH / | 1- Me | —CH$_2$CH$_2$NH$_2$ |

TABLE 1a-continued

.hydrochloride

| Compound No. | R¹ | —G— | R³ | —Y—Z |
|---|---|---|---|---|
| 69 | 6- HO— | >NH | 1- Me | —CH$_2$CH$_2$NHMe |
| 70 | 6- HO— | >NH | 1- MeO— | —CH$_2$CH$_2$NEt$_2$ |
| 71 | 6- HO— | >NH | 1- Me | —CH$_2$CH$_2$NHEt |
| 72 | 6- HO— | >NH | 1- cyclopentyl | —CH$_2$CH$_2$NMe$_2$ |
| 73 | 6- HO— | >NH | 1- (2-Me-cyclopropyl) | —CH$_2$CH$_2$NMe$_2$ |
| 74 | 6- HO— | >NH | 1- (Me-cyclopropyl) | —CH$_2$CH$_2$NMe$_2$ |
| 75 | 6- piperidin-1-yl-piperidine-N—COO— | >NH | 1,2- diMe | —CH$_2$CH$_2$NMe$_2$ |
| 76 | 6- HO— | >NH | 1- Me | —CH$_2$CH$_2$NHi-Pr |
| 77 | 6- HO— | >NH | 1- MeS— | —CH$_2$CH$_2$NMe$_2$ |
| 78 | 6- HO— | >NH | 1- PhO— | —CH$_2$CH$_2$NMe$_2$ |
| 79 | 6- MeO— | >NH | 1- F, 2,4-difluorophenyl | —CH$_2$CH$_2$NMe$_2$ |
| 80 | 6- HO— | >NH | 1- EtO— | —CH$_2$CH$_2$NMe$_2$ |

TABLE 1a-continued

[Structure: biaryl with two carbonyl groups forming N-Y-Z imide, R¹ on left ring, R³ on right ring, G bridging. .hydrochloride]

| Compound No. | R¹ | —G— | R³ | —Y—Z |
|---|---|---|---|---|
| 81 | 6- HO— | >NH | 1- Me | —CH$_2$CH$_2$NMeEt |
| 82 | 6- MeO— | >NH | 1- Me | —CH$_2$CH$_2$NHCH$_2$CH$_2$OH$_2$ |
| 83 | 6- N pyridine-COO— | >NH | 1- Me | —CH$_2$CH$_2$NMe$_2$ |
| 84 | 6- HO— | >NH | 2- N pyridyl | —CH$_2$CH$_2$NMe$_2$ |
| 85 | 6- HO— | >NH | 1- MeO—C$_6$H$_4$—O— | —CH$_2$CH$_2$NMe$_2$ |
| 86 | 6- HO— | >NH | 1- HO—C$_6$H$_4$—O— | —CH$_2$CH$_2$NMe$_2$ |
| 87 | 6- MeO— | >NH | 1- Me | —CH$_2$CH$_2$N(morpholino) |
| 88 | 6- HO— | >NH | 1- Me | —CH$_2$CH$_2$N(morpholino) |
| 89 | 6- HO— | >NH | 1- C$_6$H$_5$—O— | —CH$_2$CH$_2$NEt$_2$ |
| 90 | 6- HO— | >NH | 1- Me | —CH$_2$CH$_2$N(N'-Me-piperazino) |
| 91 | 6- HO— | >NH | 1- Me | —CH$_2$CH$_2$N(CH$_2$CH$_2$OH)$_2$ |
| 92 | 6- MeO— | >NH | 1- CH$_2$=CH— | —CH$_2$CH$_2$NMe$_2$ |

TABLE 1a-continued

[Structure: biphenyl-like with R¹ on left ring, G bridge, R³ on right ring, and N-Y-Z imide group with two C=O. .hydrochloride]

| Compound No. | R¹ | —G— | R³ | —Y—Z |
|---|---|---|---|---|
| 93 | 6- MeO—<br>7- Br | \NH/ | 1- Me₂NCH₂— | —CH₂CH₂NMe₂ |
| 94 | 6- HO— | \NH/ | 1- Me | —CH₂CH₂N⊕Me₃<br>I⊖ |
| 95 | 6- HO— | \N—C(=O)—NHMe/ | 1- Me | —CH₂CH₂NMe₂ |

TABLE 1b

[Structure: carbazole-like fused system with R¹ on left ring, R² on N, R³ on right ring and imide N-Y-Z, .hydrochloride]

| Compound No. | R¹ | R² | R³ | —Y—Z |
|---|---|---|---|---|
| 96 | 5- F | H | H | —CH₂CH₂NMe₂ |
| 97 | H | " | 1- Me | " |
| 98 | " | " | 1,4- diMe | " |
| 99 | 6- MeO— | " | " | " |
| 100 | 6- HO— | " | " | " |

A. Antitumor Effect (a) HeLa S-3 Cell Growth Inhibition Test

A test compound was appropriately diluted with a liquid medium (a minimum essential medium containing a 10% fecal calf serum). The resulting liquid was poured into each well of a 96-well micro titer plate, in an amount of 0.1 ml/well. Then, HeLa S-3 cells were diluted with the same liquid medium so that the cell concentration became $2 \times 10^4$ cells/ml, and the resulting liquid was poured into each well of the above plate in an amount of 0.1 ml/well. The resulting plate was allowed to stand in a CO₂ gas incubator of 37° C. for 4 days, to effect incubation. After the incubation, the supernatant liquid in each well was removed and fixation by ethanol was effected for 10 minutes. The fixed cells were tinted with a Giemsa's staining solution to determine the minimum growth inhibition concentration (MIC) of test compound for HeLa S-3 cells.

The results are shown in Table 2.

TABLE 2

| HeLa S-3 cell growth inhibition test | |
|---|---|
| Test compound No. | MIC (μg/ml) |
| 1 | 3.13 |
| 2 | 0.16 |
| 3 | 0.1 |
| 4 | 0.2 |
| 5 | 0.125 |
| 6 | 0.8 |
| 7 | 0.8 |
| 8 | 3.13 |
| 9 | 3.13 |
| 10 | 0.8 |
| 11 | 3.13 |
| 12 | 3.13 |
| 13 | 3.13 |
| 14 | 1.56 |
| 15 | 3.13 |
| 16 | 0.2 |
| 17 | 0.16 |
| 18 | 0.8 |
| 19 | 0.4 |
| 20 | 1.56 |
| 21 | 3.13 |
| 22 | 0.16 |
| 23 | 0.8 |
| 24 | 0.125 |
| 25 | 0.04 |
| 26 | 0.016 |
| 27 | 0.31 |
| 28 | 0.8 |
| 29 | 3.13 |
| 30 | 0.1 |
| 32 | 0.31 |
| 33 | 3.13 |
| 34 | 3.13 |
| 35 | 2.0 |
| 36 | 0.8 |
| 37 | 0.2 |
| 38 | 0.06 |
| 39 | 0.04 |
| 40 | 0.2 |
| 41 | 0.8 |
| 42 | 0.063 |
| 43 | 2.5 |
| 44 | 0.8 |
| 45 | 0.16 |
| 46 | 3.13 |
| 47 | 0.2 |
| 48 | 2.5 |
| 49 | 0.2 |
| 50 | 3.13 |
| 51 | 0.2 |
| 52 | 0.4 |
| 53 | 0.8 |

TABLE 2-continued

| HeLa S-3 cell growth inhibition test | |
|---|---|
| Test compound No. | MIC (μg/ml) |
| 54 | 0.31 |
| 55 | 2.5 |
| 56 | 0.4 |
| 57 | 1.0 |
| 58 | 1.25 |
| 59 | 0.16 |
| 60 | 0.1 |
| 61 | 0.08 |
| 62 | 0.2 |
| 63 | 1.25 |
| 64 | 0.63 |
| 65 | 0.63 |
| 66 | 2.5 |
| 67 | 2.0 |
| 68 | 0.4 |
| 69 | 0.25 |
| 70 | 0.16 |
| 71 | 0.16 |
| 72 | 0.16 |
| 73 | 0.8 |
| 74 | 0.16 |
| 75 | 0.08 |
| 76 | 0.16 |
| 77 | 0.63 |
| 78 | 0.04 |
| 79 | 1.6 |
| 80 | 0.08 |
| 81 | 0.16 |
| 82 | 0.4 |
| 83 | 0.16 |
| 84 | 2.5 |
| 85 | 0.08 |
| 86 | 0.16 |
| 87 | 5.0 |
| 88 | 2.5 |
| 89 | 0.16 |
| 90 | 1.56 |
| 91 | 1.25 |
| 92 | 0.32 |
| 93 | 3.2 |
| 94 | 6.25 |
| 95 | 1.56 |
| 96 | 6.25 |
| 97 | 3.13 |
| 98 | 0.8 |
| 99 | 0.8 |
| 100 | 2.5 |

(b) Effect on L-1210 Ascites Tumor $1 \times 10^5$ L-1210 cells were intraperitoneally transplanted to $CDF_1$ strain mice in groups of 6 members (male, 5-week old, weight = about 25 g) on day 0. A test compound dissolved in an aqueous 5% glucose solution was intraperitoneally administered to the test group of the above mice twice on day 1 and day 5. Only the aqueous 5% glucose solution was administered to the control group. Incidentally, the 25 mg/kg administration of the test compound No. 30 was effected only once on day 1. There were examined (a) the average survival days of the test group and (b) the average survival days of the control group. The examination period for survival days was 30 days. From the (a) and (b) was calculated a prolongation of survival time [T/C (%)], using the following equation:

$$T/C\ (\%) = (a/b) \times 100$$

The results are shown in Table 3.

TABLE 3

| Test compound No. | Dose (mg/kg) | T/C (%) |
|---|---|---|
| 1 | 25 | 137 |
| 2 | 5 | 180 |
| 3 | 25 | 167 |
| 9 | 25 | 131 |
| 15 | 25 | 160 |
| 17 | 5 | 126 |
|  | 25 | 129 |
| 22 | 5 | 143 |
|  | 25 | 160 |
| 23 | 1 | 128 |
|  | 5 | >272 |
| 24 | 1 | >377 |
| 28 | 5 | 176 |
|  | 25 | 379 |
| 30 | 5 | 156 |
|  | 25 | 172 |
| 31 | 5 | 176 |

(c) Effect on Ehrlich Solid Cancer $5 \times 10^6$ Ehrlich cells were transplanted to ddY strain mice in groups of 7 members (male, 5-week old, weight = about 25 g) subcutaneously at the left groin on day 0. A test compound dissolved in an aqueous 5% glucose solution was administered to the test group of the above mice intravenously at the tail twice on day 1 and day 5. Only the aqueous 5% glucose solution was administered to the control group. Incidentally, the test compound No. 1 was administered daily for six consecutive days from day 1 to day 6, and the test compound Nos. 31, 32 and 61 were administered only once on day 1. On day 10, the mice were sacrificed, and there were examined (a) the average tumor weight of the test group and (b) the average tumor weight of the control group. From the (a) and (b) was calculated T/C (%), using the following equation:

$$T/C\ (\%) = (a/b) \times 100$$

The results are shown in Table 4.

TABLE 4

| Test compound No. | Dose (mg/kg) | T/C (%) |
|---|---|---|
| 1 | 50 | 18 |
| 23 | 15 | 10 |
| 24 | 5 | 12 |
| 27 | 30 | 15 |
| 31 | 50 | 31 |
| 32 | 25 | 9 |
| 38 | 7 | 12 |
| 39 | 10 | 20 |
| 42 | 7 | 18 |
| 49 | 14 | 19 |
| 59 | 14 | 12 |
| 61 | 10 | 27 |
| 69 | 10 | 19 |
| 70 | 10 | 18 |
| 71 | 10 | 16 |
| 74 | 10 | 19 |

B. Mouse Acute Toxicity Test

Compound No. 23 (70 mg/kg) or Compound No. 28 (100 mg/kg) each dissolved in an aqueous 5% glucose solution was administered once to ddY strain mice in groups of 6 members (male, 4-week old) intravenously at the tail. However, no dead case was observed.

As is clear from the above results, the compound of the general formula [1] according to this invention has excellent antitumor activity and low toxicity.

This invention is described in more detail below by way of Reference Examples, Examples and Preparation Examples. However, this invention is not restricted to these Examples.

In column chromatography, Kieselgel 60, Art. 7734 manufactured by Merck was used as a column filler, and the mixing ratio of eluant is expressed by volume in all cases.

In the tables, the numerals in $R^1$ and $R^3$ columns each refer to a substitution site of substituent in benzene ring, indole skeleton or carbazole skeleton; the numerals in each general formula refer to a substitution site of substituent in benzene ring; in each example and table, each solvent name in parenthesis in melting point column refers to a recrystallization solvent.

The following abbreviations have the following meanings.

Me: methyl group, Et: ethyl group, Pr: n-propyl group, i-Pr: isopropyl group, Bu: n-butyl group, t-Bu: tert-butyl group, Ac: acetyl group, Ph: phenyl group, IPA: isopropyl alcohol, nPA: n-propyl alcohol, AcOEt: ethyl acetate, Et$_2$O: diethyl ether

REFERENCE EXAMPLE 1

(1)

N-Benzyl-1,2,3,4-Tetrahydrocarbazole-3,4-Dicarboximide and
N-Benzyl-1,2,3,4-tetrahydrocarbazole-2,3-dicarboximide To 7 ml of anhydrous ethanol were added 510 mg of N-benzyl-4-oxocyclohexane-1,2-dicarboximide, 490 mg of concentrated sulfuric acid and 220 mg of phenylhydrazine. The mixture was refluxed for 2 hours and then cooled to room temperature. Thereto were added 30 ml of ethyl acetate and 20 ml of water. The resulting mixture was adjusted to pH 7.5 with an aqueous saturated sodium hydrogencarbonate solution. The organic layer was separated, washed with an aqueous saturated sodium chloride solution, and dried over anhydrous magnesium sulfate. The solvent was removed by distillation under reduced pressure. The residue was purified by column chromatography (eluant: benzene/ethyl acetate =50/1 to 20/1) to obtain two fractions. The first obtained fraction was concentrated to dryness under reduced pressure, and the residue was recrystallized from isopropyl alcohol to obtain 190 mg (yield: 29%) of N-benzyl-1,2,3,4-tetrahydrocarbazole-3,4-dicarboximide as colorless needles. The later obtained fraction was concentrated to dryness under reduced pressure to remove the solvent, and the residue was recrystallized from isopropyl alcohol to obtain 120 mg (yield: 18%) of N-benzyl-1,2,3,4-tetrahydrocarbazole-2,3-dicarboximide as colorless needles.

N-benzyl-1,2,3,4-tetrahydrocarbazole-3,4-dicarboximide

IR (KBr) cm$^{-1}$: 3370, 1765, 1695.

N-benzyl-1,2,3,4-tetrahydrocarbazole-2,3-dicarboximide

IR (KBr) cm$^{-1}$: 3370, 1765, 1690.

The compounds shown in Table 5 were obtained in the same manner.

In Table 5, $R^1$ and $R^2$ refer to the respective substituents in the compound represented by the following formula.

TABLE 5

| $R^1$ | $R^2$ | IR (KBr) cm$^{-1}$: |
|---|---|---|
| 5- Cl | H | 3350, 1770, 1690 |
| 7- Cl | " | 3350, 1770, 1695 |
| 6- F | " | 3350, 1770, 1700 |
| 6- Cl | " | 3350, 1765, 1690 |
| 6- MeO— | " | 3360, 1765, 1690 |
| 6- Me | " | 3360, 1770, 1690 |
| 7- MeO— | " | 3350, 1760, 1695 |
| 8- F | " | 3350, 1760, 1690 |
| 8- MeO— | " | 3370, 1760, 1685 |
| 6,7- diMeO— | " | 3450, 1770, 1700 |
| 6,7-$\langle{}^O_O\rangle$ | " | 3360, 1765, 1690 |
| H | Ph | 1775, 1710 |

(2)

N-Benzyl-5,7-Dichloro-1,2,3,4-Tetrahydrocarbazole-3,4-Dicarboximide and
N-Benzyl-5,7-Dichloro-1,2,3,4-Tetrahydrocarbazole-2,3-Dicarboximide To 30 ml of acetic acid were added 1.54 g of N-benzyl-4-oxocyclohexane-1,2-dicarboximide, 3.0 g of zinc chloride and 1.54 g of 3,5-dichlorophenylhydrazine hydrochloride. The mixture was refluxed for 2 hours. Acetic acid was removed by distillation under reduced pressure. To the residue were added 150 ml of ethyl acetate and 50 ml of water. The organic layer was separated, washed with diluted hydrochloric acid, an aqueous saturated sodium chloride solution, an aqueous saturated sodium hydrogencarbonate solution and an aqueous saturated sodium chloride solution in this order, and dried over anhydrous magnesium sulfate. The solvent was removed by distillation under reduced pressure. The residue was purified by column chromatography (eluant: toluene/ethyl acetate=30/1 to 20/1) to obtain 670 mg (yield: 28%) of N-benzyl-5,7-dichloro-1,2,3,4-tetrahydrocarbazole-3,4-dicarboximide [IR (KBr) cm$^{-1}$: 3320, 1770, 1695] and 400 mg (yield: 17%) of N-benzyl-5,7-dichloro-1,2,3,4-tetrahydrocarbazole-2,3-dicarboximide [IR (KBr) cm$^{-1}$: 3310, 1765, 1690], both as colorless crystals.

The following compounds were obtained in the same manner.

N-benzyl-6-nitro-1,2,3,4-tetrahydrocarbazole-3,4-dicarboximide

IR (KBr) cm$^{-1}$: 3350, 1760, 1680.

N-benzyl-6-ethoxycarbonyl-1,2,3,4-tetrahydrocarbazole-3,4-dicarboximide

IR (KRr) cm$^{-1}$: 3320, 1765, 1690, 1680.

N-benzyl-6-ethoxycarbonyl-1,2,3,4-tetrahydrocarbazole-2,3-dicarboximide

IR (KBr) cm$^{-1}$: 3300, 1765, 1700, 1685.

(3) N-Benzyl-Carbazole-3,4-Dicarboximide 150 mg of N-benzyl-1,2,3,4-tetrahydrocarbazole-3,4-dicarboximide was dissolved in 5 ml of methylene chloride. To this solution was added 220 mg of 2,3-dichloro-5,6-dicyano-p-benzoquinone (abbreviated to hereinafter as DDQ). The mixture was stirred at room temperature for 10 minutes. Then, thereto were added 20 ml of methylene chloride and 10 ml of an aqueous 10% potassium carbonate solution. The organic layer was separated, washed with an aqueous saturated sodium chloride solution, and dried over anhydrous magnesium sulfate. The solvent was removed by distillation under reduced pressure. The residue was recrystallized from n-propanol to obtain 120 mg (yield: 81%) of N-benzyl-carbazole-3,4-dicarboximide as orange needles.

IR (KBr) cm$^{-1}$: 3300, 1755, 1690.

The compounds shown in Table 6 and Table 7 were obtained in the same manner.

$R^1$ and $R^2$ in Table 6 and $R^1$ in Table 7 refer to the respective substituents in the compounds represented by the following formulas.

TABLE 6

| $R^1$ | $R^2$ | IR (KBr) cm$^{-1}$: |
|---|---|---|
| 5,7- diCl | H | 3280, 1750, 1690 |
| 6- EtO$_2$C— | " | 3290, 1760, 1700 |
| 5- Cl | " | 3250, 1760, 1680 |
| 7- Cl | " | 3320, 1755, 1700 |
| 6- F | " | 3290, 1755, 1680 |
| 6- Cl | " | 3220, 1750, 1680 |
| 6- MeO— | " | 3290, 1750, 1700 |
| 6- Me | " | 3250, 1750, 1685 |
| 6- O$_2$N— | " | 3330, 1760, 1700 |
| 7- MeO— | " | 3300, 1750, 1680 |
| 8- F | " | 3290, 1760, 1700 |
| 8- MeO— | " | 3350, 1745, 1685 |
| 6,7- diMeO— | " | 3340, 1755, 1700 |
| 6,7-⟨O-O⟩ | " | 3280, 1755, 1690 |
| H | Ph | 1760, 1700 |

TABLE 7

| $R^1$ | IR (KBr) cm$^{-1}$: |
|---|---|
| 5,7- diCl | 3230, 1755, 1695 |
| 6- EtO$_2$C— | 3350, 1760, 1700 |

(4) 9-Acetylcarbazole-3,4-Dicarboxylic Anhydride

To 330 mg of N-benzyl carbazole-3,4-dicarboximide were added 5 ml of dioxane and 1.0 ml of a 5 N aqueous sodium hydroxide solution. The mixture was refluxed for 30 minutes. Thereto was added 3.0 ml of concentrated hydrochloric acid. The resulting mixture was refluxed for 2 hours and then cooled to room temperature. Thereto were added 30 ml of ethyl acetate and 20 ml of water. The organic layer was separated, washed with an aqueous saturated sodium chloride solution, and dried over anhydrous magnesium sulfate. The solvent was removed by distillation under reduced pressure. To the residue was added 3.0 ml of acetic anhydride, and the mixture was refluxed for 30 minutes and then cooled to room temperature. The precipitated crystals were collected by filtration and washed with diethyl ether to obtain 220 mg (yield: 78%) of 9-acetylcarbazole-3,4-dicarboxylic anhydride as light yellow crystals.

IR (KBr) cm$^{-1}$: 1830, 1760, 1710.

The compounds shown in Table 8 were obtained in the same manner.

In Table 8, $R^1$ and $R^2$ refer to the respective substituents in the compound represented by the following formula.

TABLE 8

| $R^1$ | $R^2$ | IR (KBr) cm$^{-1}$: |
|---|---|---|
| 5,7- diCl | Ac | 1830, 1760, 1700 |
| 6- F | " | 1830, 1760, 1695 |
| 6- MeO— | " | 1835, 1760, 1700 |
| 6- O$_2$N— | " | 1840, 1765, 1705 |

(5)

The following compound was obtained in the same manner as in (4) above.

9-Acetyl-5,7-dichlorocarbazole-2,3-dicarboxylic anhydride

IR (KBr) cm$^{-1}$: 1840, 1760, 1710.

(6) Bis(9-Acetylcarbazole-3,4,6-Tricarboxylic Anhydride) Anhydride 2 ml of dioxane and 1.5 ml of a 5 N aqueous sodium hydroxide solution were added to 300 mg of N-benzyl-6-ethoxycarbonylcarbazole-3,4-dicarboximide. The mixture was refluxed for 30 minutes. Thereto was added 3.0 ml of concentrated hydrochloric acid, and the resulting mixture was refluxed for 1 hour. 20 ml of water was added, followed by stirring for 10 minutes with ice cooling. The resulting yellow precipitate was collected by filtration, washed with 10 ml of water and dried in a desiccator to obtain 220 mg of a yellow powder. 5.0 ml of acetic anhydride was added to 100 mg of the yellow powder, and the mixture was refluxed for 40 minutes and then concentrated to dryness under reduced pressure. To the residue was added 5 ml of diisopropyl ether, and the mixture was stirred at room temperature for 10 minutes. The resulting crystals were collected by filtration and dried to obtain 110 mg of bis(9-acetylcarbazole-3,4,6-tricarboxylic anhydride) anhydride.

IR (KBr) cm$^{-1}$: 1835, 1805, 1760, 1715.

The following compound was obtained in the same manner.

Bis(9-acetylcarbazole-2,3,6-tricarboxylic anhydride) anhydride

IR (KBr) cm$^{-1}$: 1840, 1810, 1770, 1720.

REFERENCE EXAMPLE 2

(1) Diethyl 1,2,3,4-Tetrahydrocarbazole-2,3-Dicarboxylate

To 20 ml of ethanol were added 2.66 g of diethyl 4-oxocyclohexane-1,2-dicarboxylate, 2.45 g of concentrated sulfuric acid and 1.08 g of phenylhydrazine. The mixture was refluxed for 2 hours and then cooled to room temperature. Thereto were added 50 ml of ethyl acetate and 50 ml of water. The mixture was adjusted to pH 7.5 with an aqueous saturated sodium hydrogencarbonate solution. The organic layer was separated, washed with an aqueous saturated sodium chloride solution, and dried over anhydrous magnesium sulfate. The solvent was removed by distillation under reduced pressure. The residue was recrystallized from ethanol to obtain 1.87 g (yield: 59%) of diethyl 1,2,3,4-tetrahydrocarbazole-2,3-dicarboxylate as colorless needles.

IR (KBr) cm$^{-1}$:3390, 1720.

The compounds shown in Table 9 were obtained in the same manner.

In Table 9, R$^1$ refers to the corresponding substituent in the compound represented by the following formula.

TABLE 9

| R$^1$ | IR (KBr) cm$^{-1}$: |
| --- | --- |
| 5- F | } Mixture: 3360, 1710 |
| 7- F | |
| 5- Cl | } Mixture: 3360, 1710 |
| 7- Cl | |
| 6- F | 3380, 1710 |
| 6- Cl | 3360, 1710 |
| 6- MeO— | 3390, 1715 |
| 7- MeO— | 3380, 1720 |
| 8- F | 3360, 1720 |

(2) Diethyl 6-Nitro-1,2,3,4-Tetrahydrocarbazole-2,3-Dicarboxylate

To 50 ml of acetic acid were added 2.4 g of diethyl 4-oxocyclohexane-1,2-dicarboxylate, 3.0 g of zinc chloride and 1.9 g of 4-nitrophenylhydrazine hydrochloride. The mixture was refluxed for 4 hours. Then, acetic acid was removed by distillation under reduced pressure. To the residue were added 100 ml of ethyl acetate and 50 ml of water. The organic layer was separated, washed with diluted hydrochloric acid, an aqueous saturated sodium chloride solution, an aqueous saturated sodium hydrogencarbonate solution and an aqueous saturated sodium chloride solution in this order, and dried over anhydrous magnesium sulfate. The solvent was removed by distillation under reduced pressure. The residue was recrystallized from iso-propyl alcohol to obtain 750 mg (yield: 21%) of diethyl-6-nitro-1,2,3,4-tetrahydrocarbazole-2,3-dicarboxylate as colorless crystals.

IR (KBr) cm$^{-1}$: 3330, 1705.

3) Diethyl Carbazole-2,3-Dicarboxylate

To 6 g of diphenyl ether were added 630 mg of diethyl 1,2,3,4-tetrahydrocarbazole-2,3-dicarboxylate and 320 mg of 5% palladium-carbon. The mixture was refluxed in a nitrogen stream for 10 minutes and then cooled to room temperature. Thereto was added 20 ml of chloroform. The insoluble material was removed by filtration. The filtrate was subjected to distillation under reduced pressure to remove chloroform. The resulting oily material was mixed with 20 ml of n-hexane, and the mixture was stirred at room temperature for 10 minutes. The resulting precipitate was collected by filtration, washed with 5 ml of n-hexane, and dried to obtain 470 mg of colorless crystals. The colorless crystals were recrystallized from ethanol to obtain 60 mg (yield: 58%) of diethyl carbazole-2,3-dicarboxylate as colorless needles.

IR (KBr) cm$^{-1}$:13280, 1720, 1690.

The following compounds were obtained in the same manner:

Diethyl 6-fluorocarbazole-2 3-dicarboxylate

IR (KBr) cm$^{-1}$:13260, 1710, 1685.

Diethyl 6-methoxycarbazole-2,3-dicarboxylate

IR (KBr) cm$^{-1}$:13250, 1720, 1685.

(4) Diethyl 6-Chlorocarbazole-2,3-Dicarboxylate

Diethyl 6-chloro-1,2,3,4-tetrahydrocarbazole-2,3-dicarboxylate was subjected instead of the N-benzyl-1,2,3,4-tetrahydrocarbazole-3,4-dicarboximide to the same reaction as in Reference Example 1 (3), to obtain diethyl 6-chlorocarbazole-2,3-dicarboxylate as colorless crystals.

IR (KBr) cm$^{-1}$:1705, 1690.

The compounds shown in Table 10 were obtained in the same manner.

In Table 10, R$^1$ refers to the corresponding substituent in the compound represented by the following formula.

TABLE 10

| R$^1$ | IR (KBr) cm$^{-1}$: |
| --- | --- |
| 5- F* | 3280, 1730, 1690 |
| 7- F* | 3300, 1700 |
| 5- Cl* | 3250, 1715, 1700 |
| 7- Cl* | 3280, 1700 |
| 6- O$_2$N— | 3280, 1700 |
| 7- MeO— | 3260, 1690 |
| 8- F | 3270, 1720, 1700, 1680 |

Note:
*A mixture of the 5-position fluorine compound and the 7-position fluorine compound, or of the 5-position chlorine compound and the 7-position chlorine compound, obtained in an oxidation reaction was subjected to column chloromatography (eluant = toluene/ethyl acetate = 50/1 to 10/1) to separate into individual compounds.

REFERENCE EXAMPLE 3

(1) Dimethyl 1-Chloro-5,6,7,8-Tetrahydrocarbazole-3,4-Dicarboxylate

To 10 ml of acetic acid were added 320 mg of cyclohexanone, 500 mg of zinc chloride and 800 mg of 2-chloro-4,5-bis(methoxycarbonyl)phenylhydrazine hydrochloride. The mixture was refluxed for 6 hours. Then, acetic acid was removed by distillation under reduced pressure. The residue was dissolved in 100 ml of ethyl acetate. The solution was washed with 1 N hydrochloric acid, an aqueous saturated sodium chloride solution and an aqueous saturated sodium hydrogen-carbonate solution in this order, and dried over anhydrous magnesium sulfate. The solvent was removed by distillation under reduced pressure. The residue was purified by column chromatography (eluant: toluene/ethyl acetate=1/0 to 40/1) to obtain 270 mg (yield: 31%) of dimethyl 1-chloro-5,6,7,8-tetrahydrocarbazole-3,4-dicarboxylate as colorless crystals.

IR (KBr) cm$^{-1}$:13350, 1740, 1690.

The compounds shown in Table 11 were obtained in the same manner.

In Table 11, $R^1$ and $R^3$ refer to the respective substituents in the compound represented by the following formula.

TABLE 11

[Structure: tetrahydrocarbazole with $R^1$, CO$_2$Me at two positions, NH, $R^3$]

| $R^1$ | $R^3$ | IR (KBr) cm$^{-1}$: |
|---|---|---|
| H | MeO— | 3400, 1705 |
| MeO— | Cl | 3400, 1710 |
| PhCH$_2$O— | MeO— | 3350, 1735, 1690 |

(2) Dimethyl 1-Chlorocarbazole-3,4-Dicarboxylate

To 5 ml of o-dichlorobenzene were added 50 mg of dimethyl 1-chloro-5,6,7,8-tetrahydrocarbazole-3,4-dicarboxylate and 80 mg of DDQ. The mixture was refluxed for 1 hour. The solvent was removed by distillation under reduced pressure. The residue was purified by column chromatography (eluant: toluene/ethyl acetate=1/0 to 20/1) to obtain 40 mg (yield: 81%) of dimethyl 1-chlorocarbazole-3,4-dicarboxylate as colorless crystals.

IR (KBr) cm$^{-1}$:3360, 1725, 1685.

The compounds shown in Table 12 were obtained in the same manner.

In Table 12, $R^1$ and $R^3$ refer to the respective substituents in the compound represented by the following formula.

TABLE 12

[Structure: carbazole with $R^1$, CO$_2$Me at two positions, NH, $R^3$]

| $R^1$ | $R^3$ | IR (KBr) cm$^{-1}$: |
|---|---|---|
| H | MeO— | 3320, 1740, 1700 |
| MeO— | Cl | 3300, 1715 |
| PhCH$_2$O— | MeO— | 3320, 1735, 1695 |

REFERENCE EXAMPLE 4

9-Acetylcarbazole-2,3-Dicarboxylic Anhydride 20 ml of ethanol and 4.2 ml of a 2 N aqueous sodium hydroxide solution were added to 650 mg of diethyl carbazole-2,3-dicarboxylate. The mixture was refluxed for 1 hour and then cooled to room temperature. Thereto was added 4 ml of 3 N hydrochloric acid. The mixture was concentrated to dryness under reduced pressure. The residue was mixed with 30 ml of water, and the resulting mixture was stirred at room temperature for 10 minutes. The resulting precipitates were collected by filtration and dried in a desiccator to obtain 530 mg of light yellow amorphous product. The product was mixed with 5.0 ml of acetic anhydride, and the mixture was refluxed for 30 minutes and then cooled to room temeprature. The resulting crystals were collected by filtration and washed with diethyl ether to obtain 480 mg (yield: 82%) of 9-acetylcarbazole-2,3-dicarboxylic anhydride as light yellow crystals.

IR (KBr) cm$^{-1}$:11830, 1760, 1685.

The compounds shown in Table 13 and Table 14 were obtained in the same manner.

$R^1$ in Table 13 and $R^1$ and $R^3$ in Table 14 refer to the respective substituents in the compounds represented by the following formulas.

TABLE 13

[Structure: carbazole-dicarboxylic anhydride with $R^1$, N-Ac]

| $R^1$ | IR (KBr) cm$^{-1}$: |
|---|---|
| 5- F | 1840, 1770, 1710 |
| 7- F | 1840, 1765, 1690 |
| 5- Cl | 1840, 1760, 1720 |
| 7- Cl | 1845, 1785, 1705 |
| 6- F | 1840, 1760, 1690 |
| 6- Cl | 1840, 1770, 1700 |
| 6- O$_2$N— | 1840, 1770, 1710 |
| 6- MeO— | 1825, 1760, 1690 |
| 7- MeO— | 1840, 1760, 1690 |
| 8- F | 1840, 1770, 1700 |

TABLE 14

[Structure: carbazole-dicarboxylic anhydride with $R^1$, NH, $R^3$]

| $R^1$ | $R^3$ | IR (KBr) cm$^{-1}$: |
|---|---|---|
| H | Cl | 3350, 1800, 1730 |
| " | MeO— | 3280, 1820, 1740 |
| MeO— | Cl | 3350, 1800, 1740 |
| PhCH$_2$O— | MeO— | 3300, 1820, 1750 |

REFERENCE EXAMPLE 5

(1) 2-(1-Hydroxy-1-methylethyl)-1-methylindole 5.0 g of 1-methylindole was dissolved in 30 ml of anhydrous tetrahydrofuran. Thereto was dropwise added 30 ml of 1.5 M n-butyllithium hexane solution, at −30° C. in 5 minutes with stirring. The mixture was stirred at 0° C. for 30 minutes. Thereto was dropwise added 4.2 ml of acetone in 10 minutes at the same temperature, and the resulting mixture was stirred at room temperature for 10 minutes. The solvent was removed by distillation under reduced pressure. The residue was mixed with 100 ml of ethyl acetate and 50 ml of water to dissolve the residue. The organic layer was separated, washed with an aqueous saturated sodium chloride solution, and dried over anhydrous magnesium sulfate. The solvent was removed by distillation under reduced pressure. The residue was purified by column chromatography (eluant: toluene/ethyl acetate=50/1 to 20/1), followed by recrystallization from n-hexane, to obtain 3.25 g (yield: 45%) of 2-(1-hydroxy-1-methylethyl)-1-methylindole as colorless crystals.

IR (KBr) cm$^{-1}$:3300, 1460, 1370, 1350.

The following compounds were obtained in the same manner:

2-(1-Hydroxy-1-phenylethyl)-1-tosylindole
  IR (KBr) cm$^{-1}$:13500, 1590, 1440, 1345.
2-[1-Hydroxy-1-(2,4-dichlorophenyl)ethyl]-1-phenylsulfonylindole
  IR (KBr) cm$^{-1}$:13500, 1580, 1550, 1460, 1440.

(2) 2-Isopropenyl-1-Methylindole 4.0 g of 2-(1-hydroxy-1-methylethyl)-1-methylindole was dissolved in 80 ml of toluene. Thereto was added 200 mg of p-toluenesulfonic acid monohydrate. The mixture was azeotropically refluxed for 2 hours. The reaction mixture was cooled to room temperature, washed with an aqueous saturated sodium hydrogencarbonate solution and an aqueous saturated sodium chloride solution in this order, and dried over anhydrous magnesium sulfate. The solvent was removed by distillation under reduced pressure. The residue was purified by column chromatography (eluant: n-hexane/toluene=1/0 to 20/1) to obtain 850 mg (yield: 24%) of 2-isopropenyl-1-methylindole as a light yellow oily material.

IR (neat) cm$^{-1}$:1625, 1605 1460.

(3)

The compounds shown in Table 15 were obtained in the same manner as in (2), or (1) and (2) above.

In Table 15, $R^1$, $R^2$, $R^8$ and $R^9$ refer to the respective substituents in the compound represented by the following formula.

TABLE 15

(indole with $R^1$ on benzo ring, $R^2$ on N, 2-position bearing C($R^8$)=CH–$R^9$)

| $R^1$ | $R^2$ | $R^8$ | $R^9$ | IR (KBr) cm$^{-1}$: |
|---|---|---|---|---|
| H | Me | phenyl | H | 1600, 1590, 1460, 1430, 1305 |
| " | " | Me | Me | 1455, 1380, 1360, 1300 |
| " | –SO$_2$–C$_6$H$_4$–Me | phenyl | H | 1610, 1580, 1480, 1435, 1360 |
| " | –SO$_2$–phenyl | 2,4-dichlorophenyl | " | 1605, 1580, 1540, 1465, 1440 |
| " | " | 3,4-dimethoxyphenyl (MeO, OMe) | " | 1600, 1440, 1360 |
| " | " | phenyl | Me | 1440, 1360 |
| 5-MeO– | " | Me | " | 1610, 1580, 1470, 1445 |
| " | " | phenyl | H | 1600, 1570, 1460, 1430 |

TABLE 15-continued

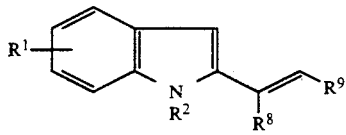

| $R^1$ | $R^2$ | $R^8$ | $R^9$ | IR (KBr) cm$^{-1}$: |
|---|---|---|---|---|
| 4-MeO— | " | Me | " | 1600, 1580, 1485, 1440, 1430 |

REFERENCE EXAMPLE 6

1-Benzyl-2-(1-Phenylvinyl)Indole 2.0 ml of a 5 N aqueous sodium hydroxide solution and 20 ml of dioxane were added to 1.0 g of 2-(1-phenylvinyl)-1-tosylindole. The mixture was refluxed for 10 hours, then cooled to room temperature. Thereto was added 50 ml of ethyl acetate, and the resulting mixture was washed with an aqueous saturated sodium chloride solution, and dried with anhydrous magnesium sulfate. The solvent was removed by distillation under reduced pressure. The residue was mixed with 5 ml of methanol. A small amount of the resulting insoluble material was removed by filtration. The filtrate was concentrated under reduced pressure to obtain 450 mg of a light yellow oily material. The oily material was dissolved in 20 ml of acetone. Thereto were added 350 mg of potassium hydroxide (purity: 90%) and 0.37 ml of benzyl bromide. The mixture was stirred at room temperature for 30 minutes. 70 ml of toluene was added to the mixture. The insoluble material was removed by filtration. The filtrate was washed with an aqueous saturated sodium chloride solution, and dried over anhydrous magnesium sulfate. The solvent was removed by distillation under reduced pressure. The residue was purified by column chromatography (eluant: n-hexane/-toluene=10/1) to obtain 590 mg (yield: 71%) of 1-benzyl-2-(1-phenylvinyl)-indole as a light yellow oily material.

IR (neat) cm$^{-1}$:1600, 1570, 1490, 1450.

REFERENCE EXAMPLE 7

2-[1-(2,4-Dichlorophenyl)Vinyl]Indole

In 30 ml of ethanol was dissolved 2.5 g of 2-[1-(2,4-dichlorophenyl)vinyl]-1-phenylsulfonylindole. Thereto was added 20 ml of a 5 N aqueous sodium hydroxide solution. The mixture was refluxed for 20 hours. The solvent was removed by distillation under reduced pressure. The residue was mixed with 20 ml of water. The mixture was adjusted to pH 7.0 with diluted hydrochloric acid, and extracted with 100 ml of ethyl acetate. The extract was washed with an aqueous saturated sodium chloride solution and dried over anhydrous magnesium sulfate. The solvent was removed by distillation under reduced pressure to obtain 1.5 g of 2-[1-(2,4-dichlorophenyl)vinyl]indole as a light yellow oily material.

IR (neat) cm$^{-1}$:3450, 1610, 1580.

The compounds shown in Table 16 were obtained in the same manner.

In Table 16, $R^1$, $R^8$ and $R^9$ refer to the respective substituents in the compound represented by the following formula.

TABLE 16

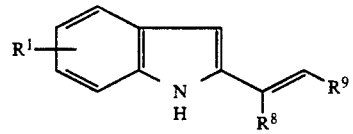

| $R^1$ | $R^8$ | $R^9$ | IR (KBr) cm$^{-1}$: |
|---|---|---|---|
| H | OMe-phenyl (with MeO) | H | 3360, 1600, 1570 |
| " | phenyl | Me | 3370, 1610, 1580 |
| 5-MeO— | phenyl | Me | 3370, 1615, 1580, 1480, 1440 |
| " | phenyl | H | 3420, 1605, 1570, 1470, 1440 |
| 4-MeO— | phenyl | Me | 3420, 1610, 1580, 1505, 1460, 1440 |

REFERENCE EXAMPLE 8

(1)

N-benzyl-1-Methyl-9-Methyl-1,2,3,4-Tetrahydro-Carbazole-3,4-Dicarboximide 850 mg of 2-isopropenyl-1-methylindole and 980 mg of N-benzylmaleimide were stirred at 110° C. for 30 minutes. The resulting solid was recrystallized from 10 ml of ethanol to obtain 1.22 g (yield: 69%) of N-benzyl-1-methyl-9-methyl-1,2,3,4-tetrahydrocarbazole-3,4-dicarboximide as colorless needles.

IR (KBr) cm$^{-1}$:11770, 1700.

The compounds shown in Table 17 were obtained in the same manner.

In Table 17, $R_2$, $R^8$ and $R^9$ refer to the respective substituents in the compound represented by the following formula.

TABLE 17

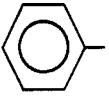

| R² | R⁸ | R⁹ | IR (KBr) cm⁻¹: |
|---|---|---|---|
| Me | [phenyl] | H | 1770, 1705 |
| " | Me | Me | 1765, 1700 |
| PhCH₂— | [phenyl] | H | 1765, 1690 |

(2) N-Phenyl-1-(2,4-Dichlorophenyl)-1,2,3,4-Tetrahydro-Carbazole-3,4-Dicarboximide 7 ml of xylene was added to a mixture of 1.5 g of 2-[1-(2,4-dichlorophenyl)vinyl]indole and 1.0 g of N-phenylmaleimide. The resulting mixture was refluxed for 1 hour. The solvent was removed by distillation under reduced pressure. The residue was recrystallized from isopropyl alcohol to obtain 1.2 g (yield: 50%) of N-phenyl-1-(2,4-dichlorophenyl)-1,2,3,4-tetrahydro-carbazole-3,4-dicarboximide as colorless crystal.

IR (KBr) cm⁻¹:3350, 1770, 1700.

The compounds shown in Table 18 were obtained in the same manner.

In Table 18, $R^1$, $R^8$ and $R^9$ refer to the respective substituents in the compound represented by the following formula.

TABLE 18

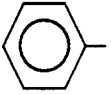

| R¹ | R⁸ | R⁹ | IR (KBr) cm⁻¹: |
|---|---|---|---|
| H | [2-OMe, 4-MeO-phenyl] | H | 3450, 1770, 1700 |
| " | [phenyl] | Me | 3390, 1770, 1700 |

TABLE 18-continued

| R¹ | R⁸ | R⁹ | IR (KBr) cm⁻¹: |
|---|---|---|---|
| 5-MeO— | Me | H | 3380, 1770, 1695 |
| 6-MeO— | " | Me | 3300, 1770, 1705 |
| " | [phenyl] | H | 3370, 1770, 1710 |

(3) N-phenyl-2,6-dimethoxy-1,2,3,4-tetrahydrocarbazole-3,4-dicarboximide 4.11 g of methoxynmethyltriphenylphosphonium chloride was suspended in 20 ml of anhydrous tetrahydrofuran. To the suspension was dropwise added 7.6 ml of 1.5 M n-butyllithium hexane solution, in 1 minute with stirring under ice cooling. The mixture was stirred at room temperature for 10 minutes. Thereto was dropwise added a solution of 1.0 g of 5-methoxyindole-2-carboxaldehyde dissolved in 10 ml of anhydrous tetrahydrofuran, in 1 minute at the same temperature. The mixture was stirred at room temperature for 2 hours. Thereto were added 100 ml of ethyl acetate and 10 ml of water. The resulting mixture was adjusted to pH 7.0 with 1 N hydrochloric acid. The organic layer was separated, washed with an aqueous saturated sodium chloride solution, and dried over anhydrous magnesium sulfate. The solvent was removed by distillation under reduced pressure. The residue was mixed with 990 mg of N-phenylmaleimide and 10 ml of xylene, and the mixture was refluxed for 1 hour. The solvent was removed by distillation under reduced pressure. The residue was purified by column chromatography (eluant: toluene/ethyl acetate=10/1), followed by recrystallization from toluene to obtain 610 mg (yield: 28%) of N-phenyl-2,6-dimethoxy-1,2,3,4-tetrahydrocarbazole-3,4-dicarboximide as colorless crystals.

IR (KBr) cm⁻¹: 3400, 1775, 1710.

The following compound was obtained in the same manner:

N-phenyl-2-methoxy-1,2,3,4-tetrahydrocarbazole-3,4-dicarboximide

IR (KBr) cm⁻¹:3380, 1770, 1705.

(4)

The compounds shown in Table 19 were obtained in the same manner as in Reference Example 1 (3).

In Table 19, $R^1$, $R^2$, $R^{6a}$, $R^8$ and $R^9$ refer to the respective substituents in the compound represented by the following formula.

TABLE 19

Structure: carbazole core with R¹ on benzene ring, R² on N, R⁸ and R⁹ on the other ring, fused dicarboximide with N–R⁶ᵃ.

| R¹ | R² | R⁸ | R⁹ | R⁶ᵃ | IR (KBr) cm⁻¹ |
|---|---|---|---|---|---|
| H | Me | Me | H | —CH₂—C₆H₅ (benzyl) | 1750, 1690 |
| " | " | " | " | —C₆H₅ (phenyl) | 1755, 1700 |
| " | " | Me | Me | " | 1740, 1680 |
| " | C₆H₅CH₂— | C₆H₅ | H | " | 1755, 1700 |
| " | H | 2,4-dichlorophenyl | " | C₆H₅ | 1760, 1700 |
| " | " | 2,4-dimethoxyphenyl (OMe, MeO) | " | " | 1760, 1705 |
| " | " | C₆H₅ | Me | " | 1750, 1685 |
| 5-MeO— | H | Me | H | C₆H₅ | 3320, 1770, 1700 |
| 6-MeO— | " | " | Me | " | 3300, 1755, 1690 |
| " | " | C₆H₅ | H | " | 3310, 1755, 1690 |
| H | " | H | MeO— | " | 3300, 1760, 1705 |
| 6-MeO— | " | " | " | " | 3300, 1745, 1685 |

(5) N-benzyl-1-Phenylcarbazole-3,4-Dicarboximide 220 mg of N-benzyl-9-benzyl-1-phenylcarbazole-3,4-dicarboximide was dissolved in 30 ml of benzene. Thereto was added 240 mg of anhydrous aluminum chloride. The mixture was stirred at room temperature for 3 hours, washed with water and an aqueous saturated sodium chloride solution in this order, and dried over anhydrous magnesium sulfate. The solvent was removed by distillation under reduced pressure. The residue was recrystallized from n-propanol to obtain 140 mg (yield: 78%) of N-benzyl-1-phenylcarbazole-3,4-dicarboximide as yellow crystals.

IR (KBr) cm⁻¹:3440, 1760, 1690.

(6)

The compounds shown in Table 20 were obtained in the same manner as in Reference Example 1 (4).

In Table 20, R¹, R², R⁸ and R⁹ refer to the respective substituents in the compound represented by the following formula.

TABLE 20

[Structure: carbazole-type with R¹, R², R⁸, R⁹ substituents and two C=O groups forming anhydride]

| R¹ | R² | R⁸ | R⁹ | IR (KBr) cm⁻¹ |
|---|---|---|---|---|
| H | H | 2,6-dimethoxyphenyl (OMe, MeO on phenyl) | H | 1820, 1760 |
| " | " | phenyl | Me | 1820, 1750 |
| 5-MeO— | " | Me | H | 1830, 1760 |
| 6-MeO— | " | phenyl | " | 1830, 1765 |
| H | Ac | H | MeO— | 1825, 1760, 1700 |
| 6-MeO— | " | " | " | 1835, 1765, 1705 |

REFERENCE EXAMPLE 9

(1) 1-Nitro-2-(1,3-Pentadienyl)Benzene 10 g of o-nitrocinnamaldehyde was dissolved in 150 ml of benzene. Thereto were added 25 g of ethyltriphenylphosphonium bromide and 150 ml of a 5 N aqueous sodium hydroxide solution. The mixture was stirred at room temperature for 2 hours. The organic layer was separated, washed with an aqueous saturated sodium chloride solution, and dried over anhydrous magnesium sulfate. The solvent was removed by distil-lation under reduced pressure. The residue was purified by column chromatography (eluant: toluene) to obtain 10.4 g (yield: 98%) of 1-nitro-2-(1,3-pentadienyl)-benzene as a light yellow oily material.

IR (neat) cm⁻¹:11600, 1510, 1340.

The compounds shown in Table 21 were obtained in the same manner.

In Table 21, R⁹ refers to the corresponding substituent in the compound represented by the following formula.

TABLE 21

[Structure: 2-nitrophenyl-CH=CH-CH=CH-R⁹]

| R⁹ | IR cm⁻¹ |
|---|---|
| Et | 1600, 1510, 1340 (neat) |

TABLE 21-continued

[Structure same as above]

| R⁹ | IR cm⁻¹ |
|---|---|
| phenyl | 1580, 1500, 1335 (KBr) |
| 3,4-dichlorophenyl | 1570, 1495, 1450, 1330 (KBr) |

(2) 1-(3-Methyl-1,3-Pentadienyl)-2-Nitrobenzene 20.3 g of ethyltriphenylphosphonium iodide was suspended in 160 ml of diethyl ether. Thereto was dropwise added 29.4 ml of 1.5 M n-butyllithium hexane solution, in 2 minutes with stirring at 0° C. Then, the mixture was stirred at 20° C. for 1 hour. To the resulting mixture being maintained at 10°–15° C. was dropwise added a solution of 8.4 g of 4-(2-nitrophenyl)-3-buten-2-one dissolved in 40 ml of diethyl ether, in 30 minutes. The resulting mixture was stirred at 20° C. for 3 hours. Thereto was added 100 ml of water. The organic layer was separated. The aqueous layer was extracted with 100 ml of diethyl ether, and the extract was combined with the previously separated organic layer. The combined solution was washed with an aqueous saturated sodium chloride solution and dried over anhydrous magnesium sulfate. The solvent was removed by distillation under reduced pressure. The residue was purified by column chromatography (eluant: n-hexane/ethyl acetate=5/1) to obtain 3.8 g (yield: 42%) of 1-(3-methyl-1,3-pentadienyl)-2-nitrobenzene as a light yellow oily material.

IR (neat) cm⁻¹:1620, 1600, 1510, 1340.

(3) 1-(3-Methyl-1,3-Butadienyl)-2-Nitrobenzene 5.0 ml of methacrolein was dissolved in 100 ml of benzene. Thereto were added 31.5 g of 2-nitro-benzyltriphenylphosphonium bromide and 100 ml of a 5 N aqueous sodium hydroxide solution. The mixture was stirred at room temperature for 5 hours. The organic layer was separated and washed with an aqueous saturated sodium chloride solution and dried over anhydrous magnesium sulfate. The solvent was removed by distillation under reduced pressure. The residue was purified by column chromatography (eluant: toluene) to obtain 2.7 g of 1-(3-methyl-1,3-butadienyl)-2-nitrobenzene (containing about 2.2 g of o-nitrotoluene) as a light yellow oily material.

IR (neat) cm⁻¹: 1600 1520, 1340.

The compounds shown in Table 22 were obtained in the same manner.

In Table 22, R¹, R⁸ and R⁹ refer to the respective substituents in the compound represented by the following formula.

TABLE 22

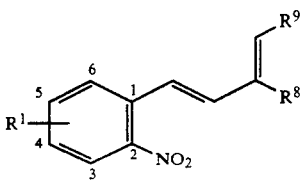

| $R^1$ | $R^8$ | $R^9$ | IR (neat) cm$^{-1}$: |
|---|---|---|---|
| 4- MeO— | Me | H | 1620, 1520, 1345 |
| 5- MeO— | " | " | 1600, 1570, 1500, 1340 |
| " | H | Me | 1600, 1570, 1495, 1330 |

(4) N-benzyl-3-Methyl-6-(2-Nitrophenyl)-1,2,3,6-Tetrahydrophthalimide

A mixture of 5.0 g of 1-nitro-2-(1,3-pentadienyl)benzene and 2.9 g of maleic anhydride was stirred at 150° C. for 5 hours. Thereto were added 150 ml of toluene and 3.2 ml of benzylamine. The resulting mixture was azeotropically refluxed for 2 hours, and then cooled to room temperature. Thereto were added 150 ml of ethyl acetate and 100 ml of water. The organic layer was separated and dried over anhydrous magnesium sulfate. The solvent was removed by distillation under reduced pressure. The residue was purified by column chromatography (eluant: toluene/ethyl acetate=1/0 to 20/1) to obtain 3.0 g (yield: 30%) of N-benzyl-3-methyl-6-(2-nitrophenyl)-1,2,3,6-tetrahydrophthalimide as colorless crystals.

IR (KBr) cm$^{-1}$: 1770, 1700.

In Table 23, $R^1$, $R^8$ and $R^9$ refer to the respective substituents in the compound represented by the following formula.

TABLE 23

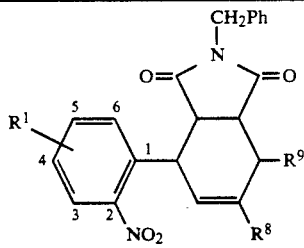

| $R^1$ | $R^8$ | $R^9$ | IR cm$^{-1}$: |
|---|---|---|---|
| H | H | Et | 1760, 1690 (KBr) |
| " | " | Ph | 1760, 1690 (KBr) |
| " | " | 2,4-Cl₂C₆H₃ | 1770, 1700 (KBr) |
| " | Me | Me | 1765, 1700 (KBr) |
| " | " | H | 1770, 1700 (neat) |
| 4- MeO— | " | " | 1770, 1730, 1700 (neat) |
| 5- MeO— | " | " | 1770, 1700 (KBr) |

TABLE 23-continued

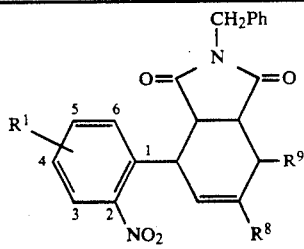

| $R^1$ | $R^8$ | $R^9$ | IR cm$^{-1}$: |
|---|---|---|---|
| " | H | Me | 1765, 1695 (neat) |

(5) N-benzyl-3-Methyl-6-(2-Nitrophenyl)Phthalimide 30 ml of chlorobenzene was added to a mixture of 5.0 g of N-benzyl-3-methyl-6-(2-nitrophenyl)-1,2,3,6-tetrahydrophthalimide and 7.0 g of DDQ. The mixture was refluxed for 8 hours, then cooled to room temperature. Thereto was added 100 ml of ethyl acetate. The resulting mixture was washed with aqueous 10% potassium carbonate solution and an aqueous saturated sodium chloride solution in this order and dried over anhydrous magnesium sulfate. The solvent was removed by distillation under reduced pressure. The residue was purified by column chromatography (eluant: toluene/ethyl acetate=100/1 to 80/1), followed by recrystallization from ethanol to obtain 2.0 g (yield: 40%) of N-benzyl-3-methyl-6-(2-nitrophenyl)phthalimide as light yellow crystals.

IR (KBr) cm$^{-1}$ 1760, 1700.

In Table 24, $R^1$, $R^8$ and $R^9$ refer to the respective substituents in the compound represented by the following formula.

TABLE 24

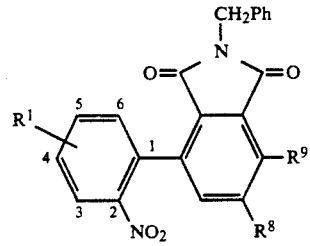

| $R^1$ | $R^8$ | $R^9$ | IR (KBr) cm$^{-1}$: |
|---|---|---|---|
| H | H | Et | 1760, 1700 |
| " | " | Ph | 1770, 1705 |
| " | " | 2,4-Cl₂C₆H₃ | 1765, 1705 |
| " | Me | Me | 1760, 1700 |
| " | " | H | 1755, 1690 |
| 4- MeO— | " | " | 1760, 1700 |
| 5- MeO— | " | " | 1765, 1700 |
| " | H | Me | 1750, 1690 |

(6) N-benzyl-2-Methylcarbazole-3,4-Dicarboximide 30 ml of o-dichlorobenzene was added to a mixture of 2.0 g of N-benzyl-3-methyl-6-(2-nitrophenyl)-phthalimide and 4.2 g of triphenylphosphine. The mixture was refluxed for 8 hours. The solvent was removed by distillation under reduced pressure. The residue was purified by column chromatography (eluant: toluene/ethyl acetate=50/1), followed by recrystallization from n-propanol to obtain 850 mg (yield: 47%) of N-benzyl-2-methylcarbazole-3,4-dicarboximide as yellow crystals.

IR (KBr) cm$^{-1}$:13300, 1740, 1680.

The compounds shown in Table 25 were obtained in the same manner.

In Table 25, $R^1$, $R^8$ and $R^9$ refer to the respective substituents in the compound represented by the following formula.

TABLE 25

| $R^1$ | $R^8$ | $R^9$ | IR (KBr) cm$^{-1}$: |
|---|---|---|---|
| H | H | Et | 3410, 1750, 1690 |
| " | " | Ph | 3350, 1750, 1675 |
| " | " | 3,4-Cl$_2$C$_6$H$_3$ | 3460, 1750, 1695 |
| " | Me | Me | 3440, 1740, 1685 |
| " | " | H | 3280, 1750, 1680 |
| 7-MeO— | " | " | 3310, 1745, 1685 |
| 6-MeO— | " | " | 3300, 1750, 1685 |
| " | H | Me | 3310, 1745, 1670 |

(7)

The following compounds were obtained in the same manner as in Reference Example 1 (4):

9-Acetyl-2-methylcarbazole-3,4-dicarboxylic anhydride
IR (KBr) cm$^{-1}$:1820, 1750, 1690.

9-Acetyl-2-phenylcarbazole-3,4-dicarboxylic anhydride
IR (KBr) cm$^{-1}$:1820, 1750, 1670.

REFERENCE EXAMPLE 10

(1) 5-Methoxy-1-Methoxymethyl-2-Propionylindole 3.00 g of 5-methoxy-1-methoxymethylindole was dissolved in 15 ml of anhydrous tetrahydrofuran. Thereto was dropwise added 11.0 ml of 1.5 M n-butyllithium hexane solution, in 5 minutes with stirring at −30° C. The resulting mixture was stirred at 0° C. for 30 minutes. This solution was dropwise added to a solution of 1.59 g of propionyl chloride dissolved in 15 ml of anhydrous tetrahydrofuran, in 30 minutes with stirring at −60° C. The reaction mixture was stirred at room temperature for 10 minutes, and then was added to 50 ml of an aqueous saturated sodium hydrogencarbonate solution in one portion. Thereto was added 150 ml of ethyl acetate. The organic layer was separated, washed with an aqueous saturated sodium chloride solution, and dried over anhydrous magnesium sulfate. The solvent was removed by distillation under reduced pressure. The residue was purified by column chromatography (eluant: toluene/ethyl acetate=50/1) to obtain 1.34 g (yield: 35%) of 5-methoxy-1-methoxymethyl-2-propionylindole as a light yellow oily material.

IR (neat) cm$^{-1}$:1660.

5 (2)

2-(1-Buten-2-yl)-5-Methoxy-1-Methoxymethylindole 2.13 g of methyltriphenylphosphonium bromide was suspended in 20 ml of anhydrous tetrahydrofuran. Thereto was dropwise added 4.0 ml of 1.5 M n-butyllithium hexane solution, in 1 minute with stirring at 0° C. The resulting mixture was stirred at 20° C. for 30 minutes. To this reaction mixture being maintained at 25°-30° C. was dropwise added a solution of 1.34 g of 5-methoxy-1-methoxymethyl-2-propionylindole dissolved in 15 ml of anhydrous tetrahydrofuran, in 5 minutes. The resulting mixture was stirred at 20° C. for 1 hour. Then, thereto were added 75 ml of ethyl acetate and 50 ml of water. The organic layer was separated, washed with an aqueous saturated sodium chloride solution, and dried over anhydrous magnesium sulfate. The solvent was removed by distillation under reduced pressure. The residue was purified by column chromatography (eluant: n-hexane/ethyl acetate=10/1) to obtain 1.13 g (yield: 85%) of 2-(1-buten-2-yl)-5-methoxy-1-methoxymethylindole as a colorless oily material.

IR (neat) cm$^{-1}$:1610, 1470, 1440, 1380.

(3)

The compounds shown in Table 26 were obtained in the same manner as in (1) and (2) above.

In Table 26, $R^3$ refers to the corresponding substituent in the compound represented by the following formula.

TABLE 26

| $R^3$ | IR (neat) cm$^{-1}$: |
|---|---|
| Me | 1605, 1465, 1440, 1370, 1340 |
| Pr | 16,15, 1470, 1445, 1385 |
| i-Pr | 1615, 1470, 1440, 1380 |
| Bu | 1610, 1465, 1440, 1380 |
| cyclopropyl | 1615, 1470, 1440, 1385 |
| cyclobutyl | 1615, 1470, 1445, 1385 |
| cyclopentyl | 1610, 1460, 1440, 1380 |

TABLE 26-continued

[Structure: 5-methoxy-2-(R³-vinyl)-1-(methoxymethyl)indole]

| R³ | IR (neat) cm⁻¹: |
|---|---|
| cyclohexyl | 1610, 1470, 1440, 1380 |
| 1-methylcyclopropyl | 1615, 1470, 1445, 1385 |
| 2-methylcyclopropyl | 1610, 1465, 1440, 1380 |
| t-Bu | 1620, 1470, 1440, 1380 |
| MeOCH₂— | 1615, 1465, 1440, 1385 |
| F₃C— | 1675, 1615, 1515, 1470, 1440 |

(4)

N-(4-methylphenyl)-1-ethyl-6-methoxy-9-methoxymethyl-1,2,3,4-tetrahydrocarbazole-3,4-dicarboximide 5 ml of xylene was added to a mixture of 580 mg of 2-(1-buten-2-yl)-5-methoxy-1-methoxymethylindole and 880 mg of N-(4-methylphenyl)maleimide. The mixture was refluxed for 1.5 hours. The solvent was removed by distillation under reduced pressure. The residue was purified by column chromatography (eluant: n-hexane/ethyl acetate=5/1 to 2/1) to obtain 510 mg (yield: 50%) of N-(4-methylphenyl)-1-ethyl-6-methoxy-9-methoxymethyl-1,2,3,4-tetrahydrocarbazole-3,4-dicarboximide as colorless crystals.

IR (KBr) cm⁻¹:1775, 1705.

The compounds shown in Table 27 were obtained in the same manner.

In Table 27, R³ refers to the corresponding substituent in the compound represented by the following formula.

TABLE 27

[Structure: tetrahydrocarbazole-dicarboximide with 6-MeO, N-CH₂OMe, N-(4-methylphenyl), R³ at 1-position]

| R³ | IR (KBr) cm⁻¹: |
|---|---|
| Me | 1765, 1705 |
| Pr | 1770, 1705 |
| i-Pr | 1770, 1705 |
| Bu | 1770, 1705 |

TABLE 27-continued

| R³ | IR (KBr) cm⁻¹: |
|---|---|
| cyclopropyl | 1775, 1710 |
| cyclobutyl | 1770, 1705 |
| cyclopentyl | 1770, 1705 |
| cyclohexyl | 1775, 1705 |
| 1-methylcyclopropyl | 1780, 1705 |
| 2-methylcyclopropyl | 1770, 1705 |
| t-Bu | 1710 |
| MeOCH₂— | 1770, 1705 |
| F₃C— | 1780, 1710 |

(5)

The compounds shown in Table 28 were obtained in the same manner as in Reference Example 1 (3).

In Table 28, R³ refers to the corresponding substituent in the compound represented by the following formula.

TABLE 28

[Structure: carbazole-dicarboximide with 6-MeO, N-CH₂OMe, N-(4-methylphenyl), R³ at 4-position]

| R³ | IR (KBr) cm⁻¹: |
|---|---|
| Me | 1745, 1700 |
| Et | 1755, 1710 |
| Pr | 1750, 1700 |
| i-Pr | 1760, 1700 |
| Bu | 1750, 1700 |

TABLE 28-continued

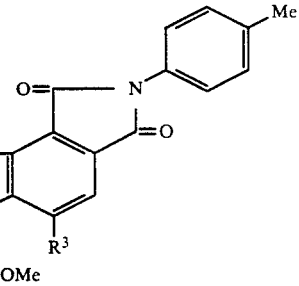

| R³ | IR (KBr) cm⁻¹: |
|---|---|
|  | 1760, 1710 |
|  | 1760, 1705 |
|  | 1755, 1705 |
|  | 1760, 1705 |
|  | 1755, 1700 |
|  | 1750, 1705 |
| t-Bu | 1760, 1705 |
| MeOCH₂— | 1750, 1700 |
| F₃C— | 1760, 1705 |

REFERENCE EXAMPLE 11

(1)

The following compounds were obtained in the same manner as in Reference Example 3 (1):

Dimethyl 1,6-dimethoxy-5,6,7,8-tetrahydrocarbazole-3,4-dicarboxylate

IR (KBr) cm⁻¹: 3200, 1735, 1705.

Dimethyl 6-benzyloxy-1-methylthio-5,6,7,8-tetrahydrocarbazole-3,4-dicarboxylate

IR (KBr) cm⁻¹: 3350, 1740, 1690.

Dimethyl 6-methoxy-1-phenoxy-5,6,7,8-tetrahydrocarbazole-3,4-dicarboxylate

IR (KBr) cm⁻¹: 3330, 1715.

6-Benzyloxy-1-ethoxy-5,6,7,8-tetrahydrocarbazole-3,4-dicarboximide*

IR (KBr) cm⁻¹: 3250, 1740, 1700.

(* 4-Ethoxy-5-hydrazinophthalimide was used as a starting material.)

(2)

The following compounds were obtained in the same manner as in Reference Example 3 (2):

Dimethyl 1,6-dimethoxycarbazole-3,4-dicarboxylate

IR (KBr) cm⁻¹: 3320, 1735, 1695.

Dimethyl 6-benzyloxy-1-methylthiocarbazole-3,4-dicarboxylate

IR (KBr) cm⁻¹: 3310, 1720, 1700.

Dimethyl 6-methoxy-1-phenoxycarbazole-3,4-dicarboxylate

IR (KBr) cm⁻¹: 3330, 1715.

6-Benzyloxy-1-ethoxycarbazole-3,4-dicarboximide

IR (KBr) cm⁻¹: 3380, 3260, 1750, 1725, 1700.

REFERENCE EXAMPLE 12

Dimethyl 1-methylcarbazole-2,3-dicarboxylate

Indoleacetic acid was reacted with acetic anhydride in the presence of boron trifluoride to obtain 1-methyl-pyrano[3,4-b]indol-3-one. The product was reacted with dimethyl acetylenedicarboxylate to obtain dimethyl 1-methylcarbazole-2,3-dicarboxylate.

IR (KBr) cm⁻¹:13310, 1730, 1690.

The following compounds were obtained in the same manner:

Dimethyl 1,4-dimethylcarbazole-2,3-dicarboxylate

IR (KBr) cm⁻¹:3360, 1705.

Dimethyl 6-methoxy-1,4-dimethylcarbazole-2,3-dicarboxylate

IR (KBr) cm⁻¹:3410, 1720.

REFERENCE EXAMPLE 13

(1)

The following compounds were obtained in the same manner as in Reference Example 4:

1,6-Dimethoxycarbazole-3,4-dicarboxylic anhydride

1-Methylcarbazole-2,3-dicarboxylic anhydride

IR (KBr) cm⁻¹:13380, 1800, 1735.

1,4-Dimethylcarbazole-2,3-dicarboxylic anhydride

IR (KBr) cm⁻¹:3360, 1810, 1735.

6-Methoxy-1,4-dimethylcarbazole-2,3-dicarboxylic anhydride

IR (KBr) cm⁻¹:13360, 1810, 1735.

6-Benzyloxy-1-methylthiocarbazole-3,4-dicarboxylic anhydride

IR (KBr) cm⁻¹:13270, 1820, 1750.

6-Methoxy-1-phenoxycarbazole-3,4-dicarboxylic anhydride

IR (KBr) cm⁻¹:3270, 1825, 1760, 1740.

(2)

The following compound was obtained using 6-benzyloxy-1-ethoxycarbazole-3,4-dicarboximide instead of the N-benzylcarbazole-3,4-dicarboximide in the same manner as in Reference Example 1 (4):

6-Benzyloxy-1-ethoxycarbazole-3,4-dicarboxylic anhydride

IR (KBr) cm⁻¹:3370, 1820, 1750.

REFERENCE EXAMPLE 14

(1)

N-phenyl-6-methoxy-8-methyl-1,2,3,4-tetrahydro-carbazole-3,4-dicarboximide

Using N-phenyl-4-oxocyclohexane-1,2-dicarboximide instead of the N-benzyl-4-oxocyclohexane-1,2-dicarboximide and using 4-methoxy-2-methylphenylhydrazine hydrochloride instead of the phenylhydrazine, the same procedure as in Reference Example 1 (1) was repeated, to obtain N-phenyl-6-methoxy-8-methyl-1,2,3,4-tetrahydrocarbazole-3,4-dicarboximide.

IR (KBr) cm⁻¹:3350, 1760, 1700.

(2)

The following compound was obtained in the same manner as in Reference Example 1 (3):
N-phenyl-6-methoxy-8-methylcarbazole-3,4-dicarboximide
IR (KBr) cm$^{-1}$:3360 1750, 1705.

REFERENCE EXAMPLE 15

(1)

The following compound was obtained in the same manner as in Reference Example 5 (1) and (2):
2-[1-(2,4-Difluorophenyl)vinyl]-5-methoxy-1-phenylsulfonylindole
IR (KBr) cm$^{-1}$:1600, 1495, 1465, 1440, 1425.

(2)

The following compound was obtained in the same manner as in Reference Example 7:
2-[1-(2,4-Difluorophenyl)vinyl]-5-methoxyindole
IR (KBr) cm$^{-1}$:13430, 1615, 1580, 1490.

(3)

The following compound was obtained in the same manner as in Reference Example 8 (2):
N-phenyl-1-(2,4-difluorophenyl) -1,2,3,4-tetrahydro-6-methoxycarbazole-3,4-dicarboximide
IR (KBr) cm$^{-1}$:13350, 1770, 1700.

(4)

The following compound was obtained in the same manner as in Reference Example 1 (3):
N-phenyl-1-(2,4-difluorophenyl)-6-methoxycarbazole-3,4-dicarboximide
IR (KBr) cm$^{-1}$: 3320 1755, 1700.

REFERENCE EXAMPLE 16

(1) 2-(1-Hydroxy-1-Methylethyl)Benzofuran 1.00 g of benzofuran was dissolved in 20 ml of anhydrous tetrahdyrofuran. Thereto was dropwise added 6.2 ml of 1.5 M n-butyllithium hexane solution, in 5 minutes with stirring at −50° C. The mixture was stirred at 0° C. for 30 minutes and then cooled to −50° C. Thereto was added 0.94 ml of acetone. The resulting mixture was stirred at room temperature for 30 minutes. The solvent was removed by distillation under reduced pressure. The residue was mixed with 30 ml of chloroform and 10 ml of water to dissolve the residue. The organic layer was separated, washed with an aqueous saturated sodium chloride solution, and dried over anhydrous magnesium sulfate. The solvent was removed by distillation under reduced pressure to obtain 1.50 g of 2-(1-hydroxy-1-methylethyl)benzofuran as a colorless oily material.

(2) 2-IsopropenylBenzofuran 3.10 g of 2-(1-hydroxy-1-methylethyl)benzofuran was dissolved in 100 ml of methylene chloride. Thereto were added 2.22 g of methanesulfonyl chloride and 3.92 g of triethylamine at 0° C. The mixture was stirred at room temperature for 4 hours, then washed with water, 1 N hydrochloric acid, an aqueous saturated sodium hydrogencarbonate solution and an aqueous saturated sodium chloride solution in this order, and dried over anhydrous magnesium sulfate. The solvent was removed by distillation under reduced pressure. The residue was purified by column chromatography (eluant: toluene) to obtain 2.44 g (yield: 88%) of 2-isopropenylbenzofuran as a colorless oily material.
IR (neat) cm$^{-1}$:1450, 1260.

(3)

The following compounds were obtained in the same manner as in (1) and (2) above.
2-isopropenyl-1-benzothiophene
IR (KBr) cm$^{-1}$:1615, 1450, 1430.
2-Isopropenyl-5-methoxy-1-benzothiophene
IR (KBr) cm$^{-1}$:1605, 1585, 1460, 1440.

REFERENCE EXAMPLE 17

(1) 2-Benzofurancarbaldehyde 2.18 g of benzofuran was dissolved in 40 ml of anhydrous tetrahydrofuran. Thereto was dropwise added 12.3 ml of 1.5 M n-butyllithium hexane solution, in 5 minutes with stirring at −50° C. The mixture was stirred at 0° C. for 30 minutes and then cooled to −60° C. Thereto was added 1.61 g of N,N-dimethylformamide, and the resulting mixture was stirred at room temperature for 1 hour. The solvent was removed by distillation under reduced pressure. The residue was mixed with 50 ml of ethyl acetate and 20 ml of water to dissolve the residue. The organic layer was separated, washed with an aqueous saturated sodium chloride solution, and dried over anhydrous magnesium sulfate. The solvent was removed by distillation under reduced pressure. The residue was purified by column chromatography (eluant: n-hexane/ethyl acetate =20/1 to 10/1) to obtain 1.70 g (yield: 63%) of 2-benzofurancarbaldehyde as a colorless oily material.
IR (neat) cm$^{-1}$: 1680.

The following compound was obtained in the same manner:
2-(1-Benzothiophene)carbaldehyde
IR (neat) cm$^{-1}$: 1660.

(2) 2-Vinylbenzofuran

To 20 ml of N,N-dimethylformamide were added 1.60 g of 2-benzofurancarbaldehyde and 4.90 g of methyltriphenylphosphonium iodide. Thereto was added 0.50 g of 60% sodium hydride with stirring under ice cooling. The mixture was stirred at room temperature for 1 hour. To the reaction mixture was added 100 ml of n-hexane. The resulting mixture was washed with water and an aqueous saturated sodium chloride solution in this order, and dried over anhydrous magnesium sulfate. The solvent was removed by distillation under reduced pressure. The residue was purified by column chromatography (eluant: n-hexane) to obtain 0.40 g (yield: 25%) of 2-vinylbenzofuran as a colorless oily material.
IR (neat) cm$^{-1}$:1540, 1440.

The following compound was obtained in the same manner:
2-Vinyl-1-benzothiophene

REFERENCE EXAMPLE 18

(1)

2-(4-Methylphenyl)-3a,4,10b,10c-tetrahydro-1H-benzofuro[3,2-e]isoindole-1,3(2H)-dione 10 ml of toluene was added to a mixture of 0.40 g of 2-vinylbenzofuran and 0.52 g of N-(4-methylphenyl)-maleimide. The mixture was refluxed for 3 hours. The solvent was removed by distillation under reduced pressure. The residue was purified by column chromatography (eluant: toluene/ethyl acetate=50/1 to 20/1) to obtain 0.45 g (yield: 49%) of 2-(4-methylphenyl)-3a,4,10b,10c-tetrahydro-1H-benzofuro-[3,2-e]isoindole-1,3(2H)-dione as colorless crystals.

IR (KBr) cm$^{-1}$:1770, 1705.

The compounds shown in Table 29 were obtained in the same manner.

In Table 29, $R^{1a}$, $R^{3a}$, R and G refer to the respective substituents in the compound represented by the following formula.

TABLE 29

| $R^{1a}$ | $R^{3a}$ | R | G | IR (KBr) cm$^{-1}$: |
|---|---|---|---|---|
| H | Me | H | —O— | 1770, 1705 |
| " | H | Me | —S— | 1765, 1700 |
| " | " | Me | " | — |
| MeO— | " | " | " | 1765, 1695 |

(2-(4-Methylphenyl)-1H-benzofuro[3,2-e]isoindole-1,3(2H)-dione 15 ml of o-dichlorobenzene was added to a mixture of 0.50 g of 2-(4-methylphenyl)-3a,4,10b,10c-tetrahydro-1H-benzofuro[3,2-e]isoindole-1,3(2H)-dione and 0.75 g of DDQ. The mixture was refluxed for 4 hours. The reaction mixture was mixed with 50 ml of chloroform. The resulting mixture was washed with an aqueous 10% potassium carbonate solution and an aqueous saturated sodium chloride solution in this order, and dried over anhydrous magnesium sulfate. The solvent was removed by distillation under reduced pressure. The residue was recrystallized from methanol to obtain 0.18 g (yield: 36%) of 2-(4-methylphenyl)-1H-benzofuro-[3,2-d]isoindole-1,3(2H)-dione as light yellow crystals.

IR (KBr) cm$^{-1}$:1760, 1710.

The compounds shown in Table 30 were obtained in the same manner.

In Table 30, $R^{1a}$, $R^{3a}$, R and G refer to the respective substituents in the compound represented by the following formula.

TABLE 30

| $R^{1a}$ | $R^{3a}$ | R | G | IR (KBr) cm$^{-1}$: |
|---|---|---|---|---|
| H | Me | H | —O— | 1760, 1700 |
| " | H | Me | —S— | 1755, 1705 |
| " | " | Me | " | 1760, 1710 |

TABLE 30-continued

| $R^{1a}$ | $R^{3a}$ | R | G | IR (KBr) cm$^{-1}$: |
|---|---|---|---|---|
| MeO— | " | " | " | 1760, 1705 |

REFERENCE EXAMPLE 19

5-Methyl-2-(4-methylphenyl)-6,6-dioxo-1H-[1]benzothieno[3,2-e]isoindole-1,3(2H)-dione In 100 ml of chloroform was dissolved 0.27 g of 5-methyl-2-(4-methylphenyl)-1H-[1]benzothieno[3,2-e]isoindole-1,3(2H)-dione. Thereto was added 0.32 g of 80% m-chloroperbenzoic acid. The mixture was stirred at room temperature for 2 hours. The reaction mixture was washed with an aqueous saturated sodium hydrogen-carbonate solution and an aqueous saturated sodium chloride solution in this order, and dried over anhydrous magnesium sulfate. The solvent was removed by distillation under reduced pressure. The residue was washed with methanol and dried to obtain 0.27 g (yield: 92%) of light brown 5-methyl-2-(4-methylphenyl)-6,6-dioxo-1H-[1]benzothieno-[3,2-e]isoindole-1,3(2H)-dione IR (KBr) cm$^{-1}$:11770, 1705.

REFERENCE EXAMPLE 20

4-Methyldibenzofuran-1,2-dicarboxylic anhydride 5 ml of ethanol and 1.2 ml of a 5 N aqueous sodium hydroxide solution were added to 200 mg of 5-methyl-2-(4-methylphenyl)-1H-benzofuro[3,2-e]isoindole-1,3(2H)-dione. The mixture was refluxed for 30 minutes. Thereto was added 1.2 ml of concentrated hydrochloric acid. The resulting mixture was refluxed for 1 hour and then cooled to room temperature. Then, thereto were added 20 ml of ethyl acetate and 10 ml of water. The organic layer was separated, washed with an aqueous saturated sodium chloride solution and dried over anhydrous magnesium sulfate. The solvent was removed by distillation under reduced pressure. The residue was mixed with 2.0 ml of acetic anhydride. The mixture was refluxed for 30 minutes, and then concentrated to dryness under reduced pressure. The residue was washed with diethyl ether and dried to obtain 140 mg (yield: 91%) of 4-methyldibenzofuran-1,2-dicarboxylic anhydride as light yellow crystals.

IR (KBr) cm$^{-1}$: 1820, 1770, 1720.

The compounds shown in Table 31 were obtained in the same manner.

In Table 31, $R^{1a}$, $R^{3a}$ and G refer to the respective substituents in the compound represented by the following formula.

TABLE 31

R¹ᵃ—[structure with G linker and R³ᵃ, anhydride group O=C-O-C=O]

| R¹ᵃ | R³ᵃ | G | IR (KBr) cm⁻¹: |
|---|---|---|---|
| H | H | —O— | 1815, 1760 |
| " | " | —S— | 1800, 1760, 1730 |
| " | Me | " | — |
| MeO— | " | " | 1825, 1760 |
| H | " | —SO$_2$— | 1810, 1770, 1730 |

REFERENCE EXAMPLE 21

(1)

The following compounds were obtained in the same manner as in Reference Example 10(1) and (2):
2-(2-Dodeca-1,11-dienyl)-5-methoxy-1-methoxymethylindole
IR (neat) cm⁻¹ 1635, 1620, 1470, 1445.
2-[1-(2-furyl)vinyl]-5-methoxy-1-methoxymethylindole
IR (neat) cm⁻¹: 1610 1470, 1440.

(2)

The following compounds were obtained in the same manner as in Reference Example 10(4):
N-phenyl-1-(9-decenyl)-6-methoxy-9-methoxymethyl-1,2,3,4-tetrahydrocarbazole-3,4-dicarboximide
IR (neat) cm⁻¹: 1775, 1705.
N-(4-methylphenyl)-1-(2-furyl)-6-methoxy-9-methoxymethyl-1,2,3,4-tetrahydrocarbazole-3,4-dicarboximide
IR (KBr) cm⁻¹: 1775, 1705.
N-(4-methylphenyl)-6-methoxy-2-(4-pyridyl)-1,2,3,4-tetrahydrocarbazole-3,4-dicarboximide
IR (KBr) cm⁻¹: 1770, 1700

(3)

The following compounds were obtained in the same manner as in Reference Example 1(3):
N-phenyl-1-(9-decenyl)-6-methoxy-9-methoxymethylcarbazole-3,4-dicarboximide
IR (KBr) cm⁻¹: 1745, 1700.
N-(4-methylphenyl)-1-(2-furyl)-6-methoxy-9-methoxymethylcarbazole-3,4-dicarboximide
IR (KBr) cm⁻¹: 1760, 1705.
N-(4-methylphenyl)-6-methoxy-2-(4-pyridyl)carbazole3,4-dicarboximide
IR (KBr) cm⁻¹: 1750, 1695.

Reference Example 22

(1)

The following compound was obtained in the same manner as in Reference Example 3(1):
Dimethyl 6-benzyloxy-1-(4-methoxyphenyloxy)-5,6,7,8-tetrahydrocarbazole-3,4-dicarboxylate (2)

The following compound was obtained in the same manner as in Reference Example 3(2):
Dimethyl 6-benzyloxy-1-(4-methoxyphenyloxy)carbazole-3,4-dicarboxylate
IR (KBr) cm⁻¹: 3370 1730, 1690.

(3)

The following compound was obtained in the same manner as in Reference Example 4:
6-Benzyloxy-1-(4-methoxyphenyloxy)carbazole-3,4-dicarboxylic anhydride
IR (KBr) cm⁻¹: 13400, 1825, 1750.

REFERENCE EXAMPLE 23

(1)

2-(3,3-Dimethoxypropylen-2-Yl)-5-Methoxy-1-Methoxymethylindole

Using 5-methoxy-1-methoxymethylindole and pyruvic aldehyde dimethylacetal, the same procedure as in Reference Example 5(1) and (2) was repeated, to obtain 2-(3,3-dimethoxypropylen-2-yl)-5-methoxy-1-methoxymethylindole.
IR (neat) cm⁻¹: 1620, 1580, 1470, 1445.

(2)

The following compound was obtained in the same manner as in Reference Example 10(4) and (5):
N-phenyl-1-dimethoxymethyl-6-methoxy-9-methoxymethylcarbazole-3,4-dicarboximide
IR (KBr) cm⁻¹: 1760, 1700.

REFERENCE EXAMPLE 24

N-phenyl-1-formyl-6-methoxy-9-methoxymethylcarbazole-3,4-dicarboximide 100 mg of N-phenyl-1-dimethoxymethyl-6-methoxy-9-methoxymethylcarbazole-3,4-dicarboxyimide was dissolved in 5 ml of tetrahydrofuran. Thereto was added 1 ml of 2N hydrochloric acid with ice cooling. The mixture was stirred at 10° C. for 10 minutes. To the resulting mixture were added 50 ml of chloroform and 50 ml of water. The organic layer was separated, washed with an aqueous saturated sodium chloride solution and dried over anhydrous magnesium sulfate. The solvent was removed by distillation under reduced pressure. The residue was recrystallized from n-propanol to obtain 70 mg (yield: 77%) of N-phenyl-1-formyl-6-methoxy-9-methoxymethylcarbazole-3,4-dicarboximide as yellow crystals.
IR (KBr) cm⁻¹: 1760, 1700, 1670.

REFERENCE EXAMPLE 25

N-phenyl-6-methoxy-9-methoxymethyl-1-vinylcarbazole-3,4-dicarboximide 150 mg of N-phenyl-1-formyl-6-methoxy-9-methoxymethylcarbazole-3,4-dicarboximide and 220 mg of methyltriphenylphosphonium iodide were dissolved in N,N-dimethylformamide. Thereto was added 20 mg of 60% sodium hydride with stirring under ice cooling. The resulting mixture was stirred at the same temperature for 30 minutes. To the reaction mixture were added 100 ml of ethyl acetate and 50 ml of water. The organic layer was separated, washed with 50 ml of water and an aqueous saturated sodium chloride solution in this order and dried over anhydrous magnesium sulfate. The solvent was removed by distillation under reduced pressure. The residue was purified by column chromatography (eluant: benzene/ethyl acetate=50/1 to 20/1) to obtain 130 mg (yield: 87%) of N-phenyl-6-methoxy-9-methoxymethyl-1-vinylcarbazole-3,4-dicarboximide.
IR (KBr) cm⁻¹: 1760, 1705.

REFERENCE EXAMPLE 26

(1) 1-Benzyl-2-isoproipenyl-5-methoxyindole 8.95 g of magnesium was suspended in 160 ml of anhydrous diethyl ether. To the suspension was dropwise added 52.3 g of methyl iodide in 1 hour with stirring under refluxing. The resulting mixture was refluxed for 1 hour. Thereto was dropwise added a solution of 38 g of 1-benzyl-2-ethoxycarbonyl-5-methoxyindole dissolved in 110 ml of anhydrous tetrahydrofuran in 40 minutes at room temperature. The resulting mixture was refluxed for 1 hour and then cooled with ice cooling. Thereto was added 400 ml of ethyl acetate and to the resulting mixture was dropwise added 300 ml of water in 1 minute with stirring at 0° C. The resulting mixture was adjusted to pH 7.0 with diluted hydrochloric acid. The organic layer was separated, washed with an aqueous saturated sodium chloride solution and dried over anhydrous magnesium sulfate. The solvent was removed by distillation under reduced pressure. The residue was dissolved in 190 ml of methylene chloride. To the solution was added 29.8 g of triethylamine, and to the resulting mixture was dropwise added 16.9 g of methanesulfonyl chloride in 20 minutes with stirring at 0° C. The resulting mixture was stirred for 20 minutes at room temeprature. The reaction mixture was washed with 1N hydrochloric acid, an aqueous saturated sodium hydrogencarbonate solution and an aqueous saturated sodium chloride solution in this order and dried over anhydrous magnesium sulfate. The solvent was removed by distillation under reduced pressure. The residue was recrystallized from acetonitrile to obtain 26.8 g (yield: 79%) of 1-benzyl-2-isopropenyl-5-methoxyindole as light yellow crystals.

IR (KBr) cm$^{-1}$: 1610, 1460, 1440, 1400.

(2)

The following compound was obtained in the same manner as in Reference Example 10(4):
N-phenyl-9-benzyl-6-methoxy-1-methyl-1,2,3,4-tetrahydrocarbazole-3,4-dicarboximide IR (KBr) cm$^{-1}$: 1770, 1700.

(3) N-phenyl-9-benzyl-7-bromo-1-bromomethyl-6-methoxycarbazole-3,4-dicarboximide 1.35 g of N-phenyl-9-benzyl-6-methoxy-1-methyl-1,2,3,4-tetrahydrocarbazole-3,4-dicarboximide was dissolved in 40 ml of methylene chloride. Thereto was dropwise added 1.92 g of bromine in 30 minutes with stirring at 0° C. The resulting mixture was stirred at room temperature in 30 minutes. The reaction mixture was washed with water, an aqueous saturated sodium hydrogen-carbonate solution and an aqueous saturated sodium chloride solution in this order, and dried over anhydrous magnesium sulfate. The solvent was removed by distillation under reduced pressure. The residue was purified by column chromatography (eluant: toluene) and recrystallized from n-propanol to obtain 0.50 g (yield: 28%) of N-phenyl-9-benzyl-7-bromo-1-bromomethyl-6-methoxycarbazole-3,4-dicarboximide as yellow crystals.

IR (KBr) cm$^{-1}$: 1760, 1705.

(4) N-phenyl-9-benzyl-7-bromo-1-dimethylaminomethyl-6-methoxycarbazole-3,4-dicarboximide 450 mg of N-phenyl-9-benzyl-7-bromo-1-bromomethyl-6-methoxycarbazole-3,4-dicarboximide was dissolved in 5 ml of methylene chloride. Thereto was added 0.5 ml of 20% dimethylamine-benzene solution. The resulting mixture was stirred for 1 hour at room temperature. To the reaction mixture was added 10 ml of methylene chloride. The resulting mixture was washed with an aqueous saturated sodium hydrogencarbonate solution and an aqueous saturated sodium chloride solution in this order, and dried over anhydrous magnesium sulfate. The solvent was removed by distillation under reduced pressure. The residue was recrystallized from n-propanol to obtain 370 mg (yield: 87%) of N-phenyl-9-benzyl-7-bromo-1-dimethylaminomethyl-6-methoxycarbazole-3,4-dicarboximide as yellow crystals.

IR (KBr) cm$^{-1}$: 1760, 1705.

(5) N-phenyl-7-bromo-1-dimethylaminomethyl-6-methoxycarbazole-3,4-dicarboximide 350 mg of N-phenyl-9-benzyl-7-bromo-1-dimethylaminomethyl-6-methoxycarbazole-3,4-dicarboximide was suspended in 5 ml of anisole. To the suspension was added 410 mg of anhydrous aluminum chloride. The resulting mixture was stirred for 120 hours at room temperature. The solvent was removed by distillation under reduced pressure. To the residue was added 20 ml of an aqueous saturated sodium hydrogencarbonate solution. The resulting mixture was stirred for 10 minutes at room temperature. The insoluble material was collected by filtration and was subjected to extraction with four 50-ml portions of chloroform. The extract was washed with an aqueous saturated sodium chloride solution and dried over anhydrous magnesium sulfate. The solvent was removed by distillation under reduced pressure. The residue was purified by column chromatography (eluant: chloroform) to obtain 250 mg (yield: 85%) of N-phenyl-7-bromo-1-dimethylaminomethyl-6-methoxycarbazole-3,4-dicarboximide as yellow amorphous product.

IR (KBr) cm$^{-1}$: 1760, 1705.

EXAMPLE 1

(1) N-(2-dimethylaminoethyl)-carbazole-3,4-dicarboximide

To 100 ml of toluene were added 1.12 g of 9-acetylcarbazole-3,4-dicarboxylic anhydride and 1.06 g of N,N-dimethylethylenediamine. The mixture was azeotropically refluxed for 2 hours. The solvent was removed by distillation under reduced pressure. The residue was recrystallized from n-propanol to obtain 960 mg (yield: 78%) of N-(2-dimethylaminoethyl)-carbazole-3,4-dicarboximide as light yellow needles.

Melting point: 198.4°-199.5° C.

IR (KBr) cm$^{-1}$: 1750, 1695.

(2) N-(2-dimethylaminoethyl)-carbazole-3,4-dicarboximide hydrochloride

In 10 ml of chloroform was dissolved 500 mg of N-(2-dimethylaminoethyl)-carbazole-3,4-dicarboximide. Into the solution was introduced hydrogen chloride gas with ice cooling, until the solution was saturated with the gas. The resulting solution was stirred for 10 minutes with ice cooling. The resulting crystals were collected by filtration and dried to obtain 450 mg of N-(2-dimethylaminoethyl)-carbazole-3,4-dicarboximide hydrochloride as yellow crystals.

IR (KBr) cm$^{-1}$: 3400, 3130, 1750, 1695.

(3)

The compounds shown in Table 32 and Table 33 were obtained in the same manner as in (1), or (1) and (2) above.

$R^1$, $R^3$, Y and Z in Table 32 and $R^1$ in Table 33 refer to the respective substituents in the compounds represented by the following formulas.

TABLE 32

| $R^1$ | $R^2$ | $R^3$ | —Y—Z | Melting point (°C.)* | IR (KBr) cm$^{-1}$:* |
|---|---|---|---|---|---|
| H | H | H | —CH$_2$CH$_2$CH$_2$NMe$_2$ | 193.2–194.2 (nPA) | 1750, 1690 |
|  |  |  |  | — | 3140, 1760, 1700 |
| 5,7- diCl | " | " | —CH$_2$CH$_2$NMe$_2$ | — | — |
|  |  |  |  | — | 1760, 1700 |
| 6- F | " | " | " | — | 1750, 1695 |
|  |  |  |  | — | 3130, 1755, 1700 |
| " | " | " | —CH$_2$CH$_2$CH$_2$NMe$_2$ | 229.0–231.0 (nPA) | 1755, 1690 |
|  |  |  |  | — | 3130, 1750, 1695 |
| 6- MeO— | H | H | —CH$_2$CH$_2$NMe$_2$ | 243.0–244.2 (nPA) | 1750, 1700 |
|  |  |  |  | — | 3150, 1750, 1700 |
| " | " | 1-C$_6$H$_4$— | " | 212.5–213.5 (nPA) | 1750, 1700 |
|  |  |  |  | — | 1750, 1700 |
| " | " | H | —CH$_2$CH$_2$N(piperidinyl) | 192.2–193.4 (nPA) | 1750, 1690 |
|  |  |  |  | — | 3170, 1760, 1700 |
| " | " | " | —CH$_2$CH$_2$N(N-Me-piperazinyl) | 224.0–224.9 (nPA) | 1755, 1695 |
|  |  |  |  | — | 3200, 1755, 1690 |
| " | " | " | —NMe$_2$ | — | 3380, 1750, 1705 |
|  |  |  |  | — | 1760, 1710 |
| " | " | " | —CH$_2$CH$_2$N(CH$_2$CH$_2$OH)$_2$ | — | 3300, 1750, 1680 |
|  |  |  |  | — | 1750, 1690 |
| " | " | " | —CH$_2$CH$_2$OH | 241.9–243.0 (nPA) | 3400, 3210, 1745, 1680 |
| 6- O$_2$N— | H | H | —CH$_2$CH$_2$NMe$_2$ | >260 (AcOEt) | 1760, 1700 |
| H | " | 1- Cl | " | 224.0–224.9 (nPA) | 1760, 1705 |
|  |  |  |  | — | 3150, 1760, 1705 |
| 6- MeO— | " | " | " | 243.9–245.2 (nPA) | 1760, 1705 |
|  |  |  |  | — | 3120, 1760, 1705 |
| H | " | 1- MeO— | " | >260 (nPA) | 1760, 1700 |
|  |  |  |  | — | 3220, 1760, 1710 |
| 5- MeO— | " | 1- Me | " | — | 1760, 1700 |
| 6- MeO— | " | H | —CH$_2$CH$_2$NEt$_2$ | 195.7–196.5 (nPA) | 3280, 1750, 1680 |
|  |  |  |  | — | 3160, 1760, 1705 |
| H | " | 2- MeO— | —CH$_2$CH$_2$NMe$_2$ | 240.5–241.3 (nPA) | 1750, 1695 |
|  |  |  |  | — | 1755, 1700 |
| 6- MeO— | H | 2- MeO— | —CH$_2$CH$_2$NMe$_2$ | 235.5–237.1 (nPA) | 1740, 1685, 1635 |
| 6-C$_6$H$_5$CH$_2$O— | " | 1- MeO— | " | 227.2–228.9 (nPA) | 1745, 1690 |
|  |  |  |  | — | 1755, 1700 |

TABLE 32-continued

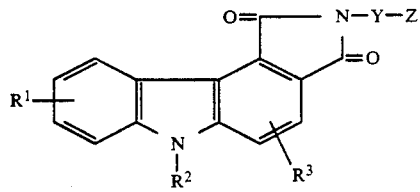

| R¹ | R² | R³ | —Y—Z | Melting point (°C.)* | IR (KBr) cm⁻¹:* |
|---|---|---|---|---|---|
| H | " | 1-MeO-C₆H₃(OMe)- | " | 213.2–214.3 (nPA) — | 3400, 1750, 1685 1750, 1690 |
| " | " | 1-C₆H₅- | " | 211.4–213.6 (nPA) | 1755, 1690 |
| " | " | 2-Me | " | — | 1755, 1700 |
| " | " | 2-Me | " | 243.0–244.6 (nPA) — | 1750, 1690 3160, 1750, 1690 |
| " | " | 2-C₆H₅- | " | 233.0–234.3 (IPA) — | 3400, 1750, 1690 3180, 1750, 1700 |

Note:
*The upper section shows physical properties of a free form.
The lower section shows physical properties of a hydrochloride.

TABLE 33

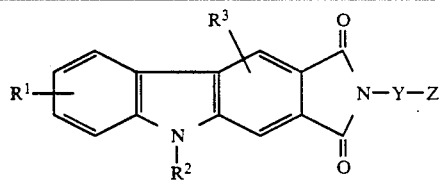

| R¹ | R² | R³ | —Y—Z | Melting point (°C.)* | IR (KBr) cm⁻¹:* |
|---|---|---|---|---|---|
| H | H | H | —CH₂CH₂NMe₂ | 218.5–219.3 (nPA) — | 1760, 1700 3200, 1755, 1690 |
| 5-F | " | " | " | >260 (nPA) — | 1750, 1690 3120, 1760, 1700 |
| 7-F | " | " | " | 257.7–259.6 (nPA) — | 1745, 1685 3350, 1750, 1690 |
| 5-Cl | " | " | " | >260 (nPA) — | 1755, 1690 3130, 1760, 1700 |
| 7-Cl | H | H | —CH₂CH₂NMe₂ | >260 (nPA) — | 1760, 1690 3200, 1760, 1690 |
| 6-F | " | " | " | 238.5–240.0 (EtOH) — | 1760, 1690 3200, 1755, 1685 |
| 6-Cl | " | " | " | — — | 1760, 1690 3180, 1755, 1685 |
| 6-O₂N— | " | " | " | — — | — 3100, 1755, 1700 |
| 6-MeO— | " | " | " | 211.0–211.8 (nPA) — | 1755, 1700 3170, 1750, 1685 |
| 7-MeO— | " | " | " | 255.5–257.2 (nPA) — | 3260, 1750, 1690 3400, 1755, 1690 |
| 8-F | H | H | —CH₂CH₂NMe₂ | >260 (nPA) — | 3250, 1750, 1680 1760, 1700 |
| 5,7-diCl | " | " | " | >260 (nPA) | 3280, 1760, 1690 3240, 1755, 1690 |

Note:
*The upper section shows physical properties of a free form.
The lower section shows physical properties of a hydrochloride.

EXAMPLE 2

The compounds shown in Table 34 were obtained in the same manner as in Reference Example 1 (4), 4, 8 (6) or 9 (7) and Example 1 (1) or Reference Example 1 (4), 4, 8 (6) or 9 (7) and Example 1 (1) and (2).

In Table 34, $R^1$, $R^2$, $R^3$, Y and Z refer to the respective substituents in the compound represented by the following formula.

TABLE 34

| $R^1$ | $R^2$ | $R^3$ | —Y—Z | Melting point (°C.)* | IR (KBr) cm$^{-1}$:* |
|---|---|---|---|---|---|
| 5- Cl | H | H | —CH$_2$CH$_2$NMe$_2$ | — | 1755, 1700 |
|  |  |  |  |  | 3120, 1760, 1700 |
| 7- Cl | " | " | " | >260 (nPA) | 1750, 1700 |
|  |  |  |  | — | 3150, 1760, 1705 |
| 6- Cl | " | " | " | >260 (toluene) | 1745, 1695 |
|  |  |  |  | — | 3100, 1760, 1700 |
| 6- MeO— | " | 1- Me | " | 240.5 –241.4 (nPA) | 1755, 1695 |
|  |  |  |  | — | 3150, 1750, 1700 |
| 6- MeO— | H | 2- Me | —CH$_2$CH$_2$NMe$_2$ | 238.6–239.7 (nPA) | 1740, 1680 |
|  |  |  |  | — | 3200, 1745, 1685 |
| " | " | 1,2- diMe | " | 241.4–242.2 (nPA) | 1745, 1690 |
|  |  |  |  | — | 1745, 1690 |
| 6- Me | " | H | " | 235.2–237.2 (nPA) | 1750, 1700 |
|  |  |  |  | — | 3120, 1755, 1700 |
| 7- MeO— | " | " | " | 236.0–237.9 (nPA) | 1750, 1700 |
|  |  |  |  | — | 3180, 1755, 1700 |
| 8- F | " | " | " | 236.0–237.5 (toluene) | 1760, 1700 |
|  |  |  |  | — | 3100, 1755, 1700 |
| 8- MeO— | " | " | " | 221.8–222.6 (nPA) | 1750, 1700 |
|  |  |  |  | — | 3150, 1750, 1700 |
| 6,7- diMeO— | " | " | " | 215.1–216.0 (nPA) | 1750, 1700 |
|  |  |  |  | — | 3200, 1740, 1685 |
| 6,7- 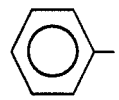 | H | H | —CH$_2$CH$_2$NMe$_2$ | >260 (nPA) | 1750, 1690 |
|  |  |  |  | — | 3180, 1755, 1700 |
| H | 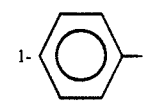 | " | " | 169.3–169.9 (nPA) | 1750, 1690 |
|  |  |  |  | — | 1760, 1705 |
| " | Me | 1- Me | " | 156.5–157.2 (nPA) | 1750, 1685 |
|  |  |  |  | — | 1750, 1695 |
| " | " | 1- 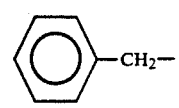 | " | 157.8–158.5 (nPA) | 1755, 1690 |
|  |  |  |  | — | 1745, 1690 |
| " | " | 1,2- diMe | " | 198.7–199.3 (nPA) | 1750, 1690 |
|  |  |  |  | — | 1740, 1680 |
| " | 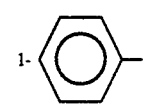—CH$_2$— | 1- 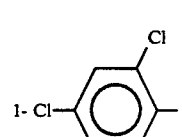 | " | — | 1750, 1700 |
|  |  |  |  | — | 1754, 1690 |
| " | H | " | " | 235.0–236.1 (nPA) | 1755, 1690 |
|  |  |  |  | — | 3300, 1755, 1700 |
| H | H | 1- Cl—⟨⟩—Cl | —CH$_2$CH$_2$NMe$_2$ | 238.7–241.4 (nPA) | 1760, 1700 |
|  |  |  |  | — | 3200, 1755, 1700 |
| " | " | 2- Et | " | 239.5–240.5 (nPA) | 1740, 1680 |
|  |  |  |  | — | 3200, 1750, 1690 |

TABLE 34-continued

[Structure: carbazole with O=C-N-Y-Z and C=O substituents, R¹, R², R³ groups]

| R¹ | R² | R³ | —Y—Z | Melting point (°C.)* | IR (KBr) cm⁻¹:* |
|---|---|---|---|---|---|
| " | " | 2-Cl—[phenyl]—Cl | " | 229.0–230.4 (IPA) — | 3270, 1755, 1690 3180, 1750, 1695 |
| " | " | 1,2 - diMe | " | — — | 3200, 1740, 1680 |
| " | " | 1- Me | " | 222.0–222.6 (nPA) — | 1750, 1695 3170, 1735, 1670 |
| 7- MeO— | H | 1- Me | —CH$_2$CH$_2$NMe$_2$ | 242.8–244.0 (EtOH) — | 1760, 1700 3200, 1750, 1690 |

Note:
*The upper section shows physical properties of a free form.
The lower section shows physical properties of a hydrochloride.

EXAMPLE 3

(1)

N-(2-dimethylaminoethyl)-6-methoxy-9-methylcarbazole-3,4-dicarboximide

In 10 ml of N,N-dimethylformamide was dissolved 380 mg of N-(2-dimethylaminoethyl)-6-methoxycarbazole-3,4-dicarboximide. Thereto was added 45 mg of 60% sodium hydride. The mixture was stirred at 40° C. for 20 minutes and then cooled to 20° C. Thereto was added 140 mg of dimethyl sulfate, and the resulting mixture was stirred at the same temperature for 2 hours. The solvent was removed by distillation under reduced pressure. The residue was mixed with 50 ml of ethyl acetate and 25 ml of water to dissolve the residue. The organic layer was separated, washed with an aqueous saturated sodium chloride solution, and dried over anhydrous magnesium sulfate. The solvent was removed by distillation under reduced pressure. The residue was recrystallized from n-propanol to obtain 200 mg (yield: 50%) of N-(2-dimethylaminoethyl)-6-methoxy-9-methylcarbazole-3,4-dicarboximide as yellow crystals.

Melting point: 137.0°–138.0° C.
IR (KBr) cm⁻¹: 1755, 1695.

(2)

The following compound was obtained in the same manner as in Example 1 (2):
N-(2-dimethylaminoethyl)-6-methoxy-9-methylcarbazole-3,4-dicarboximide hydrochloride
IR (KBr) cm⁻¹: 1750, 1695.

(3)

The compounds shown in Table 35 were obtained in the same manner as in (1), or (1) and (2) above.

In Table 35, R² refers to the corresponding substituent in the compound represented by the following formula.

TABLE 35

[Structure: MeO-substituted carbazole with O=C-NCH$_2$CH$_2$NMe$_2$ and C=O groups, R² on N]

| R² | IR (KBr) cm⁻¹:* |
|---|---|
| Et | 1775, 1690 1755, 1700 |
| Me\\CH— /Me | 1750, 1700 1760, 1700 |
| Ac | 1760, 1700 1760, 1705 |

Note:
*The upper section shows physical properties of a free form.
The lower section shows physical properties of a hydrochloride.

EXAMPLE 4

(1)

N-(2-dimethylaminoethyl)-6-hydroxycarbazole-3,4-dicarboximide 1.52 g of anhydrous aluminum chloride was suspended in 30 ml of chloroform. Thereto was added 1.69 ml of ethanethiol, and the mixture was stirred at room temperature for 10 minutes. Thereto was dropwise added, in 1 minute, a solution of 770 mg of N-(2-dimethylaminoethyl)-6-methoxycarbazole-3,4-dicarboximide dissolved in 100 ml of chloroform. The mixture was stirred at room temperature overnight. The solvent was removed by distillation under reduced pressure. The residue was mixed with 200 ml of ethyl acetate and 50 ml of an aqueous saturated sodium hydrogencarbonate solution. The mixture was stirred at room temperature for 30 minutes. The resulting insoluble material was removed by filtration. The separated insoluble material was washed with 50 ml of ethyl acetate. The washings were combined with the previously separated filtrate. The organic layer was separated, washed with an aqueous saturated sodium chloride solution, and dried over anhydrous magnesium sulfate. The solvent was removed by distillation under reduced pressure. The residue was recrystallized from n-propanol to obtain 0.49 g (yield: 66%) of N-(2-dimethylaminoethyl)-6-hydroxycarbazole-3,4-dicarboximide as orange crystals.

Melting point: >260° C.
IR (KBr) cm$^{-1}$: 3450, 1750, 1690.

(2)

The following compound was obtained in the same manner as in Example 1 (2):
N-(2-dimethylaminoethyl)-6-hydroxycarbazole-3,4-dicarboximide hydrochloride
IR (KBr) cm$^{-1}$: 3120, 1750, 1705.

(3)

The compounds shown in Table 36 and Table 37 were obtained in the same manner as in (1), or (1) and (2) above.

$R^1$, $R^2$, $R^3$, Y and Z in Table 36 and $R^1$ in Table 37 refer to the respective substituents in the compounds represented by the following formulas.

TABLE 36

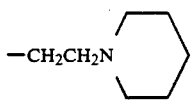

| $R^1$ | $R^2$ | $R^3$ | —Y—Z | Melting point (°C.)* | IR (KBr) cm$^{-1}$:* |
|---|---|---|---|---|---|
| 6-HO— | H | H | —CH$_2$CH$_2$NEt$_2$ | 199.3–200.0 (nPA) | 3500, 3290, 1750, 1700 |
|  |  |  |  | — | 3320, 3150, 1760, 1705 |
| 7-HO— | " | " | —CH$_2$CH$_2$NMe$_2$ | >260 (nPA) | 3250, 1745, 1680 |
|  |  |  |  | — | 3170, 1750, 1695 |
| 8-HO— | " | " | " | >260 (nPA) | 3320, 1750, 1695 |
|  |  |  |  | — | 3220, 1750, 1690 |
| 6-HO— | Ac | " | " | — | 1760, 1705, 1690 |
|  |  |  |  | — | 1760, 1705 |
| 6-HO— | Me | H | —CH$_2$CH$_2$NMe$_2$ | 221.1–222.4 (nPA) | 1745, 1685 |
|  |  |  |  | — | 3200, 1750, 1700 |
| " | Et | " | " | — | 1760, 1690 |
|  |  |  |  | — | 3160, 1750, 1685 |
| " | i-Pr | " | " | — | 3420, 1760, 1690 |
|  |  |  |  | — | 1750, 1690 |
| " | H | 1-Me | " | >260 (nPA) | 3420, 1745, 1680 |
|  |  |  |  | — | 3200, 1750, 1685 |
| " | " | 2-Me | " | >260 (nPA) | 3460, 1745, 1685 |
|  |  |  |  | — | 3200, 1745, 1685 |
| 7-HO— | " | 1-Me | " | >260 (nPA) | 3300, 1750, 1680 |
|  |  |  |  | — | 3200, 1755, 1700 |
| 6-HO— | H | H | —NMe$_2$ | — | 3450, 1760, 1700 |
|  |  |  |  | — | 3300, 1780, 1740 |
| " | " | " | 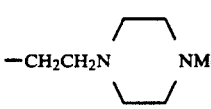 | >260 (nPA) | 3450, 1750, 1695 |
|  |  |  |  | — | 3170, 1760, 1700 |
| " | " | " | 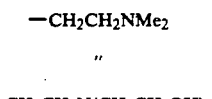 | >260 (nPA) | 1750, 1695 |
|  |  |  |  | — | 3310, 1760, 1705 |
| " | " | 1,2-diMe | —CH$_2$CH$_2$NMe$_2$ | >260 (nPA) | 3480, 1740, 1685 |
|  |  |  |  | — | 3230, 1745, 1685 |
| " | " | 1-Cl | " | >260 (nPA) | 3450, 1760, 1700 |
|  |  |  |  | — | 3200, 1760, 1700 |
| 6-HO— | H | H | —CH$_2$CH$_2$N(CH$_2$CH$_2$OH)$_2$ | 221.8–224.6 (nPA) | 3330, 1755, 1695 |
|  |  |  |  | — | 3350, 3180, 1750, 1700 |
| " | " | 2-HO— | —CH$_2$CH$_2$NMe$_2$ | 256–260 (nPA) | 3520, 3280, 1740, 1680, 1630 |
|  |  |  |  | — | 1760, 1690, 1640 |
| H | " | " | " | — | 1740, 1690 |
| " | " | 1-HO— | " | >260 (nPA) | 3390, 1750, 1700, 1660 |
|  |  |  |  | — | 1750, 1700, 1690 |

TABLE 36-continued

[Structure: carbazole with R¹, R², R³ substituents and N-Y-Z dicarboximide group]

| R¹ | R² | R³ | —Y—Z | Melting point (°C.)* | IR (KBr) cm⁻¹:* |
|---|---|---|---|---|---|
| 6-HO— | " | [1-phenyl] | " | 178.9–180.7 (nPA) | 3440, 3230, 1740, 1660 |
|  |  |  |  | — | 3260, 1745, 1690 |
| 6-HO—*¹ | " | 1-MeO— | " | >260 (nPA) | 3450, 1750, 1690 |
|  |  |  |  | — | 1750, 1700 |

Note:
*The upper section shows physical properties of a free form.
The lower section shows physical properties of a hydrochloride.
*¹A boron trifluoride-diethyl ether complex was used in place of the aluminum chloride.

TABLE 37

[Structure: carbazole-3,4-dicarboximide with NCH₂CH₂NMe₂ and R¹ substituent]

| R¹ | Melting point (°C.)* | IR (KBr) cm⁻¹:* |
|---|---|---|
| 6-HO— | >260 (nPA) | 3260, 1755, 1685 |
|  | — | 3300, 1750, 1685 |
| 7-HO— | >260 (nPA) | 3300, 1755, 1685 |
|  | — | 3300, 1755, 1685 |

Note:
*The upper section shows physical properties of a free form.
The lower section shows physical properties of a hydrochloride.

EXAMPLE 5

N-(2-dimethylaminoethyl)-6-carboxycarbazole-3,4-dicarboximide hydrochloride

To 15 ml of toluene were added 110 mg of bis(9-acetylcarbazole-3,4,6-tricarboxylic anhydride) anhydride and 130 mg of N,N-dimethylethylenediamine. The mixture was azeotropically refluxed for 2 hours and then cooled to room temperature. The resulting insoluble material was collected by filtration and dried to obtain 0.15 g of yellow crystals. To the crystals were added 3.0 ml of 3N hydrochloric acid and 3.0 ml of dioxane. The mixture was refluxed for 2 hours and then cooled to room temperature. The resulting precipitate was collected by filtration, washed with 3 ml of water, and dried to obtain 90 mg of N-(2-dimethylaminoethyl)-6-carboxycarbazole-3,4-dicarboximide hydrochloride as yellow crystals.

Melting point: >260° C.
IR (KBr) cm⁻¹: 3400, 3120, 1750, 1700.

The following compound was obtained in the same manner:

N-(2-dimethylaminoethyl)-6-carboxycarbazole-2,3-dicarboximide hydrochloride
Melting point: >260° C.
IR (KBr) cm⁻¹: 3320, 1760, 1705.

EXAMPLE 6

(1)

N-(2-dimethylaminoethyl)-6-chloro-9-methylcarbazole-3,4-dicarboximide 400 mg of N-(2-dimethylaminoethyl)-6-chlorocarbazole-3,4-dicarboximide, 50 mg of 60% sodium hydride and 150 mg of dimethyl sulfate were subjected to the same reaction as in Example 3 (1) to obtain 250 mg (yield: 60%) of N-(2-dimethylaminoethyl)-6-chloro-9-methylcarbazole-3,4-dicarboximide as yellow crystals.

Melting point: 215.0°–215.8° C. (nPA).
IR (KBr) cm⁻¹: 1750, 1685.

(2)

The following compound was obtained in the same manner as in Example 1 (2):

N-(2-dimethylaminoethyl)-6-chloro-9-methylcarbazole-3,4-dicarboximide hydrochloride
IR (KBr) cm⁻¹: 1760, 1700.

EXAMPLE 7

(1)

N-(2-dimethylaminoethyl)-6,7-dihydroxycarbazole-3,4-dicarboximide

A mixture of 210 mg of N-(2-dimethylaminoethyl)-6,7-dimethoxycarbazole-3,4-dicarboximide and 1.66 g of pyridine hydrochloride was sealed in a tube and stirred at 200°–210° C. for 2 hours. Then, 150 ml of water and 100 ml of ethyl acetate were added to the reaction mixture to dissolve the mixture. The solution was adjusted to pH 8.5 with potassium carbonate. The organic layer was separated, washed with an aqueous saturated sodium chloride solution, and dried over anhydrous potassium carbonate. The solvent was removed by distillation under reduced pressure. The residue was mixed with 20 ml of diethyl ether, and the mixture was stirred for 10 minutes. The resulting insoluble material was collected by filtration and recrystallized from n-propanol to obtain 58 mg (yield: 31%) of N-(2-dimethylaminoethyl)-6,7-dihydroxycarbazole-3,4-dicarboximide as yellow crystals.

Melting point: >260° C.
IR (KBr) cm⁻¹: 3100, 1740, 1675.

(2)

The following compound was obtained in the same manner as in Example 1 (2):
N-(2-dimethylaminoethyl)-6,7-dihydroxycarbazole-3,4-dicarboximide hydrochloride
IR (KBr) cm$^{-1}$: 3180, 1750, 1700.

EXAMPLE 8

N-(2-trimethylammonioethyl)-6-chlorocarbazole-3,4-dicarboximide iodide

In 10 ml of N,N-dimethylformamide was dissolved 200 mg of N-(2-dimethylaminoethyl)-6-chlorocarbazole-3,4-dicarboximide. Thereto was added 830 mg of methyl iodide. The mixture was stirred at room temperature for 2 hours. The resulting crystals were collected by filtration, washed with ethyl acetate, and dried to obtain 220 mg (yield: 78%) of N-(2-tri methylammonioethyl)-6-chlorocarbazole-3,4-dicarboximide iodide as yellow crystals.
Melting point: >260° C.
IR (KBr) cm$^{-1}$: 3150, 1760, 1705.

EXAMPLE 9

(1)

N-(2-dimethylaminoethyl)-6-aminocarbazole-3,4-dicarboximide

In 30 ml of methanol was dissolved 60 mg of N-(2-dimethylaminoethyl)-6-nitrocarbazole-3,4-dicarboximide. Thereto was added 30 mg of 5% palladium-carbon. The mixture was subjected to catalytic reduction in a hydrogen atmosphere at room temperature at atmospheric pressure for 5 hours. Thereto was added Celite, and the resulting mixture was filtered. The filtrate was concentrated under reduced pressure. The residue was mixed with diethyl ether, and the mixture was stirred for 10 minutes. The resulting crystals were collected by filtration and dried to obtain 30 mg (yield: 55%) of N-(2-dimethylaminoethyl)-6-aminocarbazole-3,4-dicarboximide as orange crystals.
Melting point: 216.7°-217.9° C.
IR (KBr) cm$^{-1}$: 3460, 3360, 1745, 1680.

(2)

The following compounds were obtained in the same manner as in Example 1 (2), or (1) above and Example 1 (2):
N-(2-dimethylaminoethyl)-6-aminocarbazole-3,4-dicarboximide hydrochloride
IR (KBr) cm$^{-1}$: 3170, 1750, 1700.
N-(2-dimethylaminoethyl)-6-aminocarbazole-2,3-dicarboximide hydrochloride
IR (KBr) cm$^{-1}$: 1760, 1690.

EXAMPLE 10

(1)

N-(2-bromoethyl)-6-methoxycarbazole-3,4-dicarboximide

In 4.5 ml of N,N-dimethylformamide was dissolved 450 mg of N-(2-hydroxyethyl)-6-methoxycarbazole-3,4-dicarboximide. Thereto were added 1.06 g of carbon tetrabromide and 840 mg of triphenylphosphine. The mixture was stirred at room temperature for 2 hours. The solvent was removed by distillation under reduced pressure. The residue was mixed with 50 ml of water and 50 ml of ethyl acetate. The mixture was stirred at room temperature for 10 minutes. The resulting insoluble material was removed by filtration. The organic layer was separated from the filtrate, washed with an aqueous saturated sodium chloride solution, and dried over anhydrous magnesium sulfate. The solvent was removed by distillation under reduced pressure. The residue was recrystallized from n-propanol to obtain 230 mg (yield: 42%) of N-(2-bromoethyl)-6-methoxycarbazole-3,4-dicarboximide as yellow crystals.
Melting point: 221.3°-223.7° C.
IR (KBr) cm$^{-1}$: 3360, 1750, 1685.

(2)

N-(2-pyridinioethyl)-6-methoxycarbazole-3,4-dicarboximide bromide

In 1.5 ml of pyridine was dissolved 30 mg of N-(2-bromoethyl)-6-methoxycarbazole-3,4-dicarboximide. The solution was refluxed for 1 hour and then cooled to room temperature. The resulting crystals were collected by filtration, washed with diethyl ether, and dried to obtain 30 mg (yield: 82%) of N-(2-pyridinioethyl)-6-methoxycarbazole-3,4-dicarboximide as yellow crystals.
Melting point: >260° C.
IR (KBr) cm$^{-1}$: 1750, 1700.

EXAMPLE 11

(1)

N-(2-dimethylaminoethyl)-5,6,7,8-tetrahydrocarbazole-3,4-dicarboximide and
N-(2-dimethylaminoethyl)-5,6,7,8-tetrahydrocarbazole-2,3-dicarboximide 11.3 ml of concentrated hydrochloric acid and 12 ml of water were added to 7.90 g of N-(2-dimethylaminoethyl)-4-aminophthalimide. The mixture was cooled to 0° C. Thereto was dropwise added a solution of 2.34 g of sodium nitrite dissolved in 5 ml of water, in 15 minutes with stirring. The mixture was added to a mixture of 21.3 g of sodium sulfite, 50 ml of water and 20 g of ice, in one portion. The resulting mixture was heated to 60° C., stirred at the same temperature for 15 minutes, cooled to room temperature, and adjusted to pH 1.5 with 6N hydrochloric acid. The solvent was removed by distillation under reduced pressure. The residue was mixed with 50 ml of acetic acid, and the mixture was concentrated to dryness under reduced pressure. This procedure was conducted two more times to remove water. To the residue were added 130 ml of acetic acid and 6.64 g of cyclohexanone, and the mixture was refluxed for 2 hours. While the mixture was hot, the resulting insoluble material was removed by filtration. The filtrate was concentrated to dryness under reduced pressure. The residue was mixed with 200 ml of ethyl acetate and 200 ml of water. The mixture was adjusted to pH 7.5 with an aqueous saturated sodium hydrogencarbonate solution. The organic layer was separated, washed with an aqueous saturated sodium chloride solution, and dried over anhydrous magnesium sulfate. The solvent was removed by distillation under reduced pressure. The residue was purified by column chromatography (eluant: chloroform/methanol=1/0 to 10/1) to obtain two fractions. The first obtained fraction was concentrated to dryness under reduced pressure. The residue was recrystallized from toluene to obtain 180 mg (yield: 1.7%) of N-(2-dimethylaminoethyl)-5,6,7,8-tetrahydrocarbazole-3,4-dicarboximide as yellow needles. The later obtained fraction was concentrated to dryness under reduced pressure. The residue was recrystallized from toluene to obtain 1.60 g (yield: 15%) of N-(2-dimethylaminoethyl)-5,6,7,8-tetrahydrocarbazole-2,3-dicarboximide as light yellow needles.

N-(2-dimethylaminoethyl)-5,6,7,8-tetrahydrocarbazole-3,4-dicarboximide
IR (KBr) cm$^{-1}$: 1750, 1695.

N-(2-dimethylaminoethyl)-5,6,7,8-tetrahydrocarbazole-2,3-dicarboximide
IR (KBr) cm$^{-1}$: 1750, 1685.

(2)

N-(2-dimethylaminoethyl)-carbazole-3,4-dicarboximide 3.6 g of diphenyl ether and 70 mg of 10% palladium-carbon were added to 180 mg of N-(2-dimethylaminoethyl)-5,6,7,8-tetrahydrocarbazole-3,4dicarboximide. The mixture was refluxed in a nitrogen stream for 15 minutes, and then cooled to room temperature. Thereto was added 40 ml of chloroform. The resulting insoluble material was removed by filtration. The filtrate was mixed with 25 ml of water. The mixture was adjusted to pH 1.0 with 6N hydrochloric acid. The aqueous layer was separated, washed with 10 ml of chloroform, and mixed with 20 ml of chloroform. The mixture was adjusted to pH 7.5 with an aqueous saturated sodium hydrogencarbonate solution. The organic layer was separated, washed with an aqueous saturated sodium chloride solution, and dried over anhydrous magnesium sulfate. The solvent was removed by distillation under reduced pressure. The residue was recrystallized from ethanol to obtain 100 mg (yield: 56%) of N-(2-dimethylaminoethyl)-carbazole-3,4-dicarboximide as yellow needles.

The physical properties of this compound were identical with the physical properties (melting point, IR) of the compound obtained in Example 1 (1).

The following compound was obtained in the same manner:

N-(2-dimethylaminoethyl)-carbazole-2,3-dicarboximide

The physical properties of this compound were identical with the physical properties (melting point, IR) of the compound obtained in Example 1 (3).

EXAMPLE 12

(1)

N-(2-dimethylaminoethyl)-6-methoxy-1-propylcarbazole-3,4-dicarboximide 1.0 ml of N,N-dimethylethylenediamine was added to 300 mg of N-(4-methylphenyl)-6-methoxy-9-methoxymethyl-1-propylcarbazole-3,4-dicarboximide. The mixture was refluxed for 30 minutes and then concentrated to dryness under reduced pressure. To the residue were added 15 ml of methanol and 1.5 ml of concentrated hydrochloric acid. The mixture was refluxed for 30 minutes. The solvent was removed y distillation under reduced pressure. The residue was mixed with 50 ml of ethyl acetate and 20 ml of an aqueous saturated sodium hydrogencarbonate solution to dissolve the residue. The organic layer was separated, washed with an aqueous saturated sodium chloride solution, and dried over anhydrous magnesium sulfate. The solvent was removed by distillation under reduced pressure. The residue was recrystallized from n-propanol to obtain 180 mg (yield: 67%) of N-(2-dimethylaminoethyl)-6-methoxy-1-propylcarbazole-3,4-dicarboximide as yellow needles.

Melting point: 207.0°–208.3° C.
IR (KBr) cm$^{-1}$: 1750, 1700.

(2)

The following compound was obtained in the as in Example 1 (2):

N-(2-dimethylaminoethyl)-6-methoxy-1-propylcarbazole-3,4-dicarboximide hydrochloride
IR (KBr) cm$^{-1}$: 3180, 1750, 1700.

(3)

The compounds shown in Table 38 were obtained in the same manner as in (1) and (2) above.

In Table 38, $R^1$, $R^3$, Y and Z refer to the respective substituents in the compound represented by the following formula.

TABLE 38

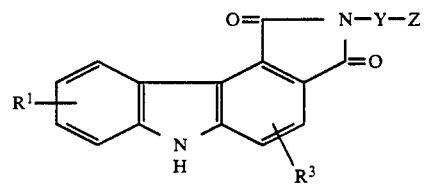

| $R^1$ | $R^3$ | —Y—Z | Melting point*3 (°C.) | IR (KBr) cm$^{-1}$:*3 |
|---|---|---|---|---|
| 6-MeO— | 1-Et | —CH$_2$CH$_2$NEt$_2$ | — | 1750, 1700 |
|  |  |  | — | 3170, 1750, 1705 |
| " | " | —CH$_2$CH$_2$NMe$_2$ | — | 1755, 1700 |
|  |  |  | — | 3180, 1750, 1700 |
| " | 1-Me | —CH$_2$CH$_2$NEt$_2$ | 221.8–223.0 (nPA) | 3270, 1745, 1680 |
| " | " | —CH$_2$CH$_2$NPr$_2$ | — | — |
|  |  |  | >260 | 1750, 1700 |
| 6-MeO— | 1-Me | —CH$_2$CH$_2$N(i-Pr)$_2$ | — | — |
|  |  |  | — | 1750, 1700 |
| " | " | —CH$_2$CH$_2$NHMe | >260 (nPA) | 1745, 1695 |
|  |  |  | — | 3210, 1745, 1690 |
| " | " | —CH$_2$CH$_2$NHEt | — | — |
|  |  |  | >260 | 3180, 1740, 1680 |
| " | " | —CH$_2$CH$_2$NHAc | >260 (AcOEt) | 3270, 1750, 1690, 1650 |
|  |  |  | — | — |
| " | " | —CH$_2$CH$_2$NH(i-Pr) | 192.6–195.6 (MeOH) | 1750, 1685 |

TABLE 38-continued
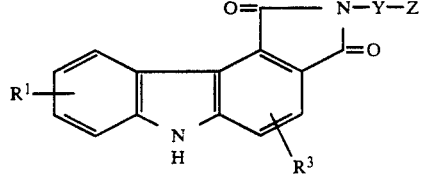
| R[1] | R[3] | —Y—Z | Melting point[*3] (°C.) | IR (KBr) cm[-1];[*3] |
|---|---|---|---|---|
| | | | — | 3200, 1740, 1680 |
| " | 1- i-Pr | —CH₂CH₂NMe₂ | 222.8–224.3 (nPA) | 1750, 1700 |
| | | | — | 3160, 1755, 1700 |
| " | " | —CH₂CH₂NEt₂ | 139.2–140.5 (MeOH) | 1750, 1700 |
| | | | — | 3150, 1755, 1700 |
| 6- MeO— | 1- Bu | —CH₂CH₂NMe₂ | — | 1750, 1690 |
| | | | — | 3140, 1750, 1695 |
| " | " | —CH₂CH₂NEt₂ | 168.9–169.5 (nPA) | 3250, 1750, 1675 |
| | | | — | 3150, 1755, 1705 |
| " | 1-  | —CH₂CH₂NMe₂ | 229.0–230.8 (nPA) | 1750, 1695 |
| | | | — | 3150, 1750, 1700 |
| " | " | —CH₂CH₂NEt₂ | 146.8–147.9 (nPA) | 1755, 1700 |
| | | | — | 3160, 1760, 1705 |
| " | 1-  | —CH₂CH₂NMe₂ | 216.7–218.3 (nPA) | 1750, 1700 |
| | | | — | 3170, 1750, 1700 |
| " | " | —CH₂CH₂NEt₂ | — | 1750, 1695 |
| | | | — | 3200, 1755, 1705 |
| " | 1- 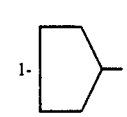 | —CH₂CH₂NMe₂ | 205.6–206.9 (nPA) | 1750, 1700 |
| | | | — | 3150, 1750, 1700 |
| 6- MeO— | 1- 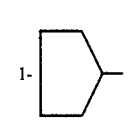 | —CH₂CH₂NEt₂ | — | 1750, 1700 |
| | | | — | 3170, 1760, 1710 |
| " | 1- 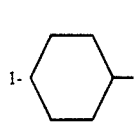 | —CH₂CH₂NMe₂ | 206.5–207.4 (nPA) | 1750, 1700 |
| | | | — | 3200, 1755, 1700 |
| " | " | —CH₂CH₂NEt₂ | 204.0–205.1 (nPA) | 1750, 1700 |
| | | | — | 3180, 1755, 1705 |
| " | 1-  | —CH₂CH₂NMe₂ | 186.9–187.3 (nPA) | 1760, 1710 |
| | | | — | — |
| " | " | —CH₂CH₂NEt₂ | 117.3–119.0 ([*1]) | 1750, 1700 |
| | | | — | 3250, 1755, 1705 |
| " | 1- 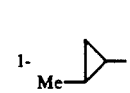 | —CH₂CH₂NMe₂ | 177.0–178.4 (nPA) | 1750, 1700 |
| | | | — | 3150, 1750, 1695 |
| " | " | —CH₂CH₂NHEt | — | 1750, 1690 |
| | | | — | 1750, 1685 |
| 6- MeO— | 1- t-Bu | —CH₂CH₂NMe₂ | — | 3400, 1750, 1700 |
| | | | — | — |
| " | 1- MeOH₂— | " | 197.3–198.3 (nPA) | 1750, 1700 |
| | | | — | 3170, 1750, 1700 |
| " | 1- F₃C— | " | 233.0–235.7 (nPA) | 1755, 1700 |
| | | | — | 3150, 1760, 1710 |

TABLE 38-continued

[Structure: carbazole with O=/N-Y-Z and =O groups, R¹ on left ring, R³ on right ring, NH bridge]

| R¹ | R³ | —Y—Z | Melting point*³ (°C.) | IR (KBr) cm⁻¹:*³ |
|---|---|---|---|---|
| " | 1-F-[phenyl]-F | " | 193.4–196.0 (*²) — | 1755, 1685 1760, 1700 |
| " | 1- Me | —CH₂CH₂NHCH₂CH₂OH | 234.5–237.2 (nPA) — | 3290, 1740, 1670 1740, 1680 |
| 6- MeO— 8- Me | H | —CH₂CH₂NMe₂ | 200.0–202.0 (nPA) — | 1745, 1695 1750, 1695 |

Note:
*¹Recrystallization solvent = Et₂O-n-hexane
*²Recrystallization solvent = AcOEt-n-hexane
*³The upper section shows physical properties of a free form.
The lower section shows physical properties of a hydrochloride.

EXAMPLE 13

(1)

N-(2-ethylmethylaminoethyl)-6-methoxy-1-methylcarbazole-3,4-dicarboximide 0.3 ml of 37% formalin and 3 ml of formic acid were added to 140 mg of N-(2-ethylaminoethyl)-6-methoxy-1-methylcarbazole-3,4-dicarboximide. The mixture was refluxed for 1 hour. The solvent was removed by distillation under reduced pressure. To the residue were added 20 ml of ethyl acetate and 10 ml of an aqueous saturated sodium hydrogencarbonate solution. The organic layer was separated and dried over anhydrous magnesium sulfate. The solvent was removed by distillation under reduced pressure. The residue was purified by column chromatography (eluant: chloroform/methanol =50/1 to 10/1) to obtain 50 mg (yield: 34%) of N-(2-ethylmethylaminoethyl)-6-methoxy-1-methylcarbazole-3,4-dicarboximide as yellow crystals.

IR (KBr) cm⁻¹: 1750, 1690.

(2)

The following compound was obtained in the same manner as in Example 1 (2).

N-(2-ethylmethylaminoethyl)-6-methoxy-1-methylcarbazole-3,4-dicarboximide hydrochloride

EXAMPLE 14

N-(2-aminoethyl)-6-methoxy-1-methylcarbazole-3,4-dicarboximide hydrochloride 20 ml of ethanol and 10 ml of concentrated hydrochloric acid were added to 150 mg of N-(2-acetylaminoethyl)-6-methoxy-1-methylcarbazole-3,4-dicarboximide. The mixture was refluxed for 15 hours and then cooled to room temperature. The resulting crystals were collected by filtration, washed with ethanol, and dried to obtain 100 mg (yield: 68%) of N-(2-aminoethyl)-6-methoxy-1-methylcarbazole-3,4-dicarboximide hydrochloride as yellow crystals.

Melting point: >260° C.
IR (KBr) cm⁻¹: 3200, 1745, 1680.

EXAMPLE 15

The compounds shown in Table 39 and Table 40 were obtained in the same manner as in Example 1 (1) and 1 (2).

R¹, R³, Y and Z in Table 39 and R¹ and R³ in Table 40 refer to the respective substituents in the compounds represented by the following formulas.

TABLE 39

[Structure: carbazole with O=/N-Y-Z and =O groups, R¹ on left ring, R³ on right ring, NH bridge]

| R¹ | R³ | —Y—Z | Melting point* (°C.) | IR (KBr) cm⁻¹:* |
|---|---|---|---|---|
| 6- MeO— | 1- MeO— | —CH₂CH₂NMe₂ | >260 (EtOH) — | 1750, 1695 3450, 3220, 1755, 1700 |
| 6- PhCH₂O— | " | —CH₂CH₂NEt₂ | 187.0–188.8 (EtOH) — | 1745, 1685 |
| " | 1- MeS— | —CH₂CH₂NMe₂ | 239.7–244.2 (EtOH) | 3300, 1750, 1690 |

TABLE 39-continued

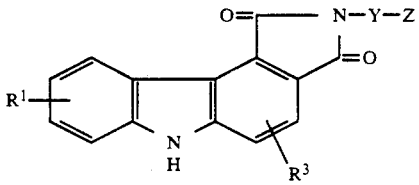

| R¹ | R³ | —Y—Z | Melting point* (°C.) | IR (KBr) cm⁻¹:* |
|---|---|---|---|---|
| 6- MeO— | 1- PhO— | " | >260 (EtOH) | 1750, 1695 |
|  |  |  | — | 3450, 3200, 1755, 1700 |
| 6- PhCH₂O— | 1- EtO— | —CH₂CH₂NMe₂ | 211.0–212.2 (EtOH) | 1755, 1705 |
|  |  |  | — | — |

Note:
*The upper section shows physical properties of a free form.
The lower section shows physical properties of a hydrochloride.

TABLE 40

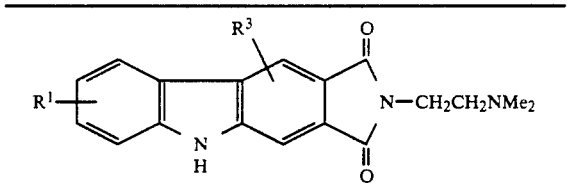

| R¹ | R³ | Melting point* (°C.) | IR (KBr) cm⁻¹:* |
|---|---|---|---|
| H | 1- Me | 229.1–231.0 (nPA) | 1750, 1700 |
|  |  | — | 3180, 1750, 1690 |
| " | 1,4- diMe | >260 (EtOH) | 3320, 1740, 1670 |
|  |  | — | 3130, 1740, 1685 |
| 6- MeO— | " | >260 (EtOH) | 3350, 1735, 1670 |
|  |  | — | 3150, 1740, 1685 |

Note:
*The upper section shows physical properties of a free form.
The lower section shows physical properties of a hydrochloride.

EXAMPLE 16

(1)

The compounds shown in Table 41 were obtained in the same manner as in Example 4 (1) and (2).

In Table 41, R¹, R³, Y and Z refer to the respective substituents in the compound represented by the following formula.

TABLE 41

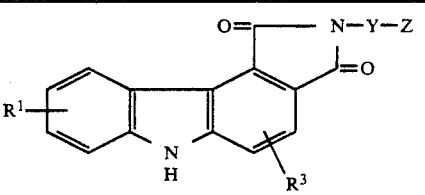

| R¹ | R³ | —Y—Z | Melting point* (°C.) | IR (KBr) cm⁻¹:* |
|---|---|---|---|---|
| 6- HO— | 1- Et | —CH₂CH₂NMe₂ | >260 (nPA) | 3330, 1745, 1685 |
|  |  |  | — | 3160, 1750, 1695 |
| " | 1- Me | —CH₂CH₂NEt₂ | — | 3310, 1750, 1685 |
|  |  |  | — | 3250, 1750, 1705 |
| " | 1- i-Pr | —CH₂CH₂NMe₂ | 219.0–220.4 (nPA) | 3270, 1750, 1700 |
|  |  |  | — | 3250, 1755, 1700 |
| " | " | —CH₂CH₂NEt₂ | 211.7–215.0 (nPA) | 1750, 1685 |
|  |  |  | — | 3280, 1750, 1700 |
| 6- HO— | 1-  | —CH₂CH₂NMe₂ | 259.9–261.2 (nPA) | 3270, 1750, 1700 |
|  |  |  | — | 3250, 1755, 1700 |
| " | " | —CH₂CH₂NEt₂ | 229.0–231.0 (nPA) | 3220, 1750, 1700 |
|  |  |  | — | 3240, 1750, 1700 |
| " | 1-  | —CH₂CH₂NMe₂ | 244.7–247.2 (nPA) | 3300, 1755, 1695 |
|  |  |  | — | 3250, 1755, 1705 |

TABLE 41-continued

Structure: Carbazole with R¹ on benzene ring, NH, R³ on pyrrole side, and dicarboximide group (O=C-N-Y-Z / C=O)

| R¹ | R³ | —Y—Z | Melting point* (°C.) | IR (KBr) cm⁻¹:* |
|---|---|---|---|---|
| " | " | —CH₂CH₂NEt₂ | — | 3390, 1745, 1690 |
|  |  |  | — | 3270, 1750, 1700 |
| " | 1-cyclopentyl | —CH₂CH₂NMe₂ | 258.0–260.0 (nPA) | 1750, 1705 |
|  |  |  | — | 3250, 1750, 1705 |
| " | " | —CH₂CH₂NEt₂ | 213.5–215.2 (nPA) | 3240, 1750, 1680 |
|  |  |  | — | 3220, 1755, 1700 |
| " | 1-(2-Me-cyclopropyl) | —CH₂CH₂NMe₂ | >260 (nPA) | 3260, 1750, 1705 |
|  |  |  | — | — |
| 6-HO— | 1-(2-Me-cyclopropyl) | —CH₂CH₂NEt₂ | 198.8–200.2 (Et₂O) | 3300, 1755, 1705 |
|  |  |  | — | 3250, 1750, 1700 |
| " | 1-(2-Me-cyclopropyl, Me on other position) | —CH₂CH₂NMe₂ | 253.0–256.0 (nPA) | 3200, 1750, 1705 |
|  |  |  | — | 3250, 1750, 1700 |
| " | " | —CH₂CH₂NHEt | 223.0–225.0 (nPA) | 3250, 1750, 1680 |
|  |  |  | — | 3200, 1750, 1680 |
| " | 1-F₃C— | —CH₂CH₂NMe₂ | — | — |
|  |  |  | — | 1760, 1705 |
| " | 1-HO— | " | >260 | 3430, 3370, 1740, 1675 |
|  |  |  | — | 3240, 1750, 1695 |
| " | 1-MeS— | " | >260 (EtOH) | 1750, 1685 |
|  |  |  | — | 3230, 1750, 1695 |
| " | 1-PhO— | " | >260 (EtOH) | 3470, 1755, 1700 |
|  |  |  | — | 3260, 1755, 1700 |
| 6-HO— | 1-(2,4-difluorophenyl) | —CH₂CH₂NMe₂ | >260 (nPA) | 3450, 3250, 1750, 1685 |
|  |  |  | — | 1750, 1695 |
| " | 1-Me | —CH₂CH₂N(Me)(Et) | 227.8–231.0 (nPA) | 1750, 1690 |
|  |  |  | — | 1750, 1700 |
| " | " | —CH₂CH₂NHCH₂CH₂OH | — | 3270, 1750, 1680 |
|  |  |  | — | 1750, 1680 |

Note:
*The upper section shows physical properties of a free form.
The lower section shows physical properties of a hydrochloride.

(2)

The following compounds were obtained in the same manner as in Example 4 (1) and (2).
N-(2-dimethylaminoethyl)-6-hydroxy-1,4-dimethylcarbazole-2,3-dicarboximide
Melting point: >260° C. (nPA).
IR (KBr) cm⁻¹: 3360, 1730, 1670.
N-(2-dimethylaminoethyl)-6-hydroxy-1,4-dimethylcarbazole-2,3-dicarboximide hydrochloride
IR (KBr) cm⁻¹: 3200, 1740, 1685.

EXAMPLE 17

(1)
N-(2-diethylaminoethyl)-6-hydroxy-1-methoxycarbazole-3,4-dicarboximide 1.8 ml of ethanethiol and 0.47 ml of boron trifluoride-diethyl ether complex were added to 180 mg of N-(2-diethylaminoethyl)-6-benzyloxy-1-methoxycarbazole-3,4-dicarboximide. The mixture was stirred at room temperature overnight. Thereto were added 100 ml of ethyl acetate and 50 ml of an aqueous saturated sodium hydrogencarbonate solution. The mixture was stirred at room temperature for 10 minutes. The organic layer was separated and dried over anhydrous magnesium sulfate. The solvent was removed by distillation under reduced pressure. The residue was purified by column chromatography (eluant: chloroform/methanol=40/1 to 10/1), followed by recrystallization from ethanol to obtain 26 mg (yield: 18%) of N-(2-diethylaminoethyl)-6-hydroxy-1-methoxycarbazole-3,4-dicarboximide as yellow crystals.

Melting point: 226.1°–227.5° C.
IR (KBr) cm$^{-1}$: 3360, 1740, 1680.

(2)

The following compound was obtained in the same manner as in Example 1 (2).

N-(2-diethylaminoethyl)-6-hydroxy-1-methoxycarbazole-3,4-dicarboximide hydrochloride
IR (KBr) cm$^{-1}$: 3150, 1750, 1700.

EXAMPLE 18

(1)

N-(2-dimethylaminoethyl)-1-ethoxy-6-hydroxycarbazole-3,4-dicarboximide

In 10 ml of acetic acid was dissolved 31 mg of N-(2-dimethylaminoethyl)-6-benzyloxy-1-ethoxycarbazole-3,4-dicarboximide. Thereto was added 30 mg of 5% palladium-carbon. The mixture was subjected to catalytic reduction in a hydrogen atmosphere at room temperature at atmospheric pressure. The resulting insoluble material was removed by filtration. The filtrate was subjected to distillation under reduced pressure to remove the solvent. The residue was mixed with 50 ml of ethyl acetate and 50 ml of an aqueous saturated sodium hydrogencarbonate solution. The organic layer was separated, washed with an aqueous saturated sodium chloride solution, and dried over anhydrous potassium carbonate. The solvent was removed by distillation under reduced pressure. The residue was recrystallized from ethanol to obtain 20 mg (yield: 80%) of N-(2-dimethylaminoethyl)-1-ethoxy-6-hydroxycarbazole-3,4-dicarboximide as orange crystals.

Melting point: 259.8°–261.3° C.
IR (KBr) cm$^{-1}$: 3450, 1745, 1680.

(2)

The following compound was obtained in the same manner as in Example 1 (2).

N-(2-dimethylaminoethyl)-1-ethoxy-6-hydroxycarbazole-3,4-dicarboximide hydrochloride
IR (KBr) cm$^{-1}$: 3450, 3220, 1750, 1695.

EXAMPLE 19

(1)

N-(2-dimethylaminoethyl)-6-hydroxy-1-methoxymethylcarbazole-3,4-dicarboximide 520 mg of 60% sodium hydride was suspended in 10 ml of N,N-dimethylformamide. Thereto was dropwise added a solution of 0.87 ml of ethanethiol dissolved in 5 ml of N,N-dimethylformamide, in 5 minutes with stirring at room temperature. Then, thereto was added 90 mg of N-(2-dimethylaminoethyl)-6-methoxy-1-methoxymethylcarbazole-3,4-dicarboximide. The mixture was stirred at room temperature overnight. The solvent was removed by distillation under reduced pressure. The residue was mixed with 50 ml of ethyl acetate and 20 ml of water. The organic layer was separated, washed with an aqueous saturated sodium chloride solution, and dried over anhydrous magnesium sulfate. The solvent was removed by distillation under reduced pressure. The residue was purified by column chromatography (eluant: chloroform/methanol=40/1 to 20/1), followed by recrystallization from n-propanol to obtain 30 mg (yield: 35%) of N-(2-dimethylaminoethyl)-6-hydroxy-1-methoxymethylcarbazole-3,4-dicarboximide as yellow crystals.

Melting point: 234.7°–236.7° C.
IR (KBr) cm$^{-1}$: 1755, 1700.

(2)

The following compound was obtained in the same manner as in Example 1 (2).

N-(2-dimethylaminoethyl)-6-hydroxy-1-methoxymethylcarbazole-3,4-dicarboximide hydrochloride
IR (KBr) cm$^{-1}$: 3130, 1750, 1700.

EXAMPLE 20

(1)

N-(2-diethylaminoethyl)-1-ethyl-6-hydroxycarbazole-3,4-dicarboximide 4.0 ml of an aqueous 47% hydrobromide solution was added to 80 mg of N-(2-diethylaminoethyl)-1-ethyl-6-methoxycarbazole-3,4-dicarboximide. The mixture was refluxed for 40 minutes. Thereto was added 30 ml of water. The resulting mixture was adjusted to pH 9 with potassium carbonate, and extracted with 50 ml of ethyl acetate. The extract was washed with an aqueous saturated sodium chloride solution, and dried over anhydrous magnesium sulfate. The solvent was removed by distillation under reduced pressure. The residue was recrystallized from isopropyl alcohol to obtain 35 mg (yield: 45%) of N-(2-diethylaminoethyl)-1-ethyl-6-hydroxycarbazole-3,4-dicarboximide as yellow crystals.

Melting point: 187.5°–189.0° C.
IR (KBr) cm$^{-1}$: 3310, 1750, 1685.

(2)

The following compound was obtained in the same manner as in Example 1 (2).

N-(2-diethylaminoethyl)-1-ethyl-6-hydroxycarbazole-3,4-dicarboximide hydrochloride
IR (KBr) cm$^{-1}$: 3250, 1750, 1700.

(3)

The compounds shown in Table 42 were obtained in the same manner as in (1) and (2) above.

In Table 42, $R^1$, $R^3$, Y and Z refer to the respective substituents in the compound represented by the following formula.

TABLE 42

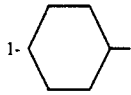

| R$^1$ | R$^3$ | —Y—Z | Melting point* (°C.) | IR (KBr) cm$^{-1}$:* |
|---|---|---|---|---|
| 6- HO— | 1- Me | —CH$_2$CH$_2$NPr$_2$ | — | 3330, 1745, 1685 |
| | | | — | 3250, 1750, 1700 |
| " | " | —CH$_2$CH$_2$N(i-Pr)$_2$ | — | 3330, 1750, 1690 |
| | | | — | 3230, 1755, 1705 |
| " | " | —CH$_2$CH$_2$NHMe | >260 (nPA) | 3450, 1750, 1690 |
| | | | — | 3200, 1745, 1685 |
| " | " | —CH$_2$CH$_2$NHEt | >260 (nPA) | 3280, 1745, 1680 |
| | | | — | 3150, 1750, 1680 |
| 6- HO— | 1- Me | —CH$_2$CH$_2$NH$_2$ | >260 (IPA) | 3330, 1745, 1680 |
| | | | — | 3220, 1750, 1680 |
| " | 1- Pr | —CH$_2$CH$_2$NMe$_2$ | >260 (nPA) | 3200, 1745, 1690 |
| | | | — | 3180, 1750, 1695 |
| " | 1- Bu | " | 250.4–252.3 (nPA) | 3400, 1750, 1685 |
| | | | — | 3180, 1750, 1700 |
| " | " | —CH$_2$CH$_2$NEt$_2$ | 220.9–222.3 (nPA) | 3230, 1750, 1700 |
| | | | — | 3200, 1750, 1700 |
| " | 1-cyclohexyl | —CH$_2$CH$_2$NMe$_2$ | 244.0–246.5 (nPA) | 3200, 1755, 1705 |
| | | | — | 3300, 1755, 1700 |
| " | " | —CH$_2$CH$_2$NEt$_2$ | 205.8–207.7 (CHCl$_3$—Et$_2$O) | 3290, 1755, 1705 |
| | | | — | 3220, 1755, 1705 |
| " | 1- t-Bu | —CH$_2$CH$_2$NMe$_2$ | — | 3380, 1745, 1690 |
| | | | — | 3300, 1755, 1705 |
| 6- HO— 8- Me | H | —CH$_2$CH$_2$NMe$_2$ | >260 | 3450, 1750, 1695 |
| | | | — | 3220, 1750, 1690 |
| 6- HO— | 1- Me | —CH$_2$CH$_2$NH(i-Pr) | >260 (MeOH) | 1750, 1680 |
| | | | — | 3200, 1745, 1680 |

Note:
*The upper section shows physical properties of a free form.
The lower section shows physical properties of a hydrochloride.

EXAMPLE 21

N-(2-dimethylaminoethyl)-6-(1-piperidylcarbonyloxy)-carbazole-3,4-dicarboximide hydrochloride In 8 ml of pyridine was dissolved 200 mg of N-(2-dimethylaminoethyl)-6-hydroxycarbazole-3,4-dicarboximide. There was added 460 mg of 1-piperidylcarbonyl chloride. The mixture was stirred at room temperature overnight. The solvent was removed by distillation under reduced pressure. The residue was mixed with 10 ml of isopropyl alcohol. The mixture was stirred at room temperature for 10 minutes. The resulting crystals were collected by filtration and dried to obtain 180 mg (yield: 62%) of N-(2-dimethylaminoethyl-6-(1-piperidyl-carbonyloxy)carbazole-3,4-dicarboximide hydrochloride as yellow crystals.

IR (KBr) cm$^{-1}$: 1750, 1700.

The compounds shown in Table 43 were obtained in the same manner.

In Table 43, R$^1$ and R$^3$ refer to the respective substituents in the compound represented by the following formula.

TABLE 43

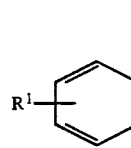

| R$^1$ | R$^3$ | IR (KBr) cm$^{-1}$: |
|---|---|---|
| 6-(piperidyl-N—COO—) | 1- Me | 1745, 1700 |
| 6-(morpholino-N—COO—) | H | 1755, 1700 |
| 6- AcO— | 1- Me | 1750, 1705, 1695 |
| " | H | 1760, 1745, 1705 |
| " | 1- Me | 1745, 1690 |

TABLE 43-continued

[Structure: carbazole core with R¹ substituent, N—CH₂CH₂NMe₂ group, =O groups, and R³ substituent; hydrochloride]

| R¹ | R³ | IR (KBr) cm⁻¹: |
|---|---|---|
| [6-piperidinyl-piperidine-N-COO—] | " | 1760, 1705 |
| " | 1,2-diMe | 1745, 1685 |
| [6-N-phenyl-COO—] | 1-Me | 1745, 1690 |

EXAMPLE 22

(1)

2-(2-Dimethylaminoethyl)-5-methyl-1H-benzofuro[3,2-e]isoindole-1,3(2H)-dione

To 50 ml of toluene were added 140 mg of 4-methyl-dibenzofuran-1,2-dicarboxylic anhydride and 270 mg of N,N-dimethylethylenediamine. The mixture was azeotropicallyl refluxed for 2 hours. The solvent was removed by distillation under reduced pressure. The residue was recrystallized from ethanol to obtain 160 mg (yield: 89%) of 2-(2-dimethylaminoethyl)-5-methyl-1H-benzofuro[3,2-e]isoindole-1,3(2H)-dione as light yellow needles.

Melting point: 134.4°-135.3° C.
IR (KBr) cm⁻¹: 1760, 1700.

(2)

2-(2-Dimethylaminoethyl)-5-methyl-1H-benzofuro[3,2-e]isoindole-1,3(2H)-dione hydrochloride In 10 ml of chloroform was dissolved 150 mg of 2-(2-dimethylaminoethyl)-5-methyl-1H-benzofuro[3,2-e]-isoindole-1,3(2H)-dione. Into the solution was introduced hydrogen chloride gas with ice cooling, until the solution was saturated with the gas. The resulting solution was stirred for 10 minutes with ice cooling. The resulting crystals were collected by filtration and dried to obtain 140 mg (yield: 84%) of 2-(2-dimethylaminoethyl)-5-methyl-1H-benzofuro[3,2-e]isoindole-1,3(2H)-dione hydrochloride as light yellow crystals.

IR (KBr) cm⁻¹: 1755, 1695.

The compounds shown in Table 44 were obtained in the same manner as in (1) and (2) above.

In Table 44, R¹, R³, G, Y and Z refer to the respective substituents in the compound represented by the following formula.

TABLE 44

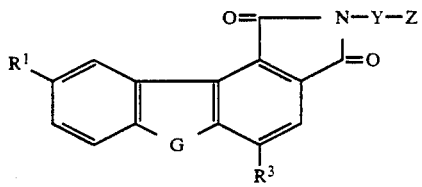

| R¹ | R³ | G | —Y—Z | Melting point* (°C.) | IR (KBr) cm⁻¹:* |
|---|---|---|---|---|---|
| H | H | —O— | —CH₂CH₂NMe₂ | — | 1750, 1695 |
|  |  |  |  | — | 1760, 1700 |
| " | " | —S— | " | 152.5–154.7 (nPA) | 1755, 1695 |
|  |  |  |  | — | 1760, 1700 |
| " | Me | " | " | 151.8–157.5 (nPA) | 1755, 1700 |
|  |  |  |  | — | 1760, 1700 |
| MeO— | " | " | " | 187.7–189.3 (IPA) | 1750, 1690 |
|  |  |  |  | — | 1750, 1690 |
| MeO— | Me | —S— | —CH₂CH₂NEt₂ | 144.1–148.1 (IPA) | 1750, 1690 |
|  |  |  |  | — | 1755, 1700 |
| H | " | —SO₂— | —CH₂CH₂NMe₂ | 214.5–218.2 (nPA) | 1760, 1700 |
|  |  |  |  | — | 1770, 1700 |

Note:
*The upper section shows physical properties of a free form.
The lower section shows physical properties of a hydrochloride.

EXAMPLE 23

(1)

2-(2-Dimethylaminoethyl)-9-hydroxy-5-methyl-1H-[1]benzothieno[3,2-e]isoindole-1,3(2H)-dione 690 mg of anhydrous aluminum chloride was suspended in 100 ml of methylene chloride. To the suspension was added 1.1 ml of ethanethiol at room temperature, and the mixture was stirred at the same temperature for 30 minutes. Thereto was dropwise added, in 1 minute, a solution of 380 mg of 2-(2-dimethylaminoethyl)-9-methoxy-5-methyl-1H-[1]benzothieno[3,2-e]isoindole-1,3(2H)-dione dissolved in 100 ml of methylene chloride. The mixture was stirred at room temperature overnight. The solvent was removed by distillation under reduced pressure. The residue was mixed with 100 ml of ethyl acetate and 50 ml of an aqueous saturated sodium hydrogencarbonate solution. The mixture was stirred for 30 minutes. The resulting insoluble material was removed by filtration. The separated insoluble material was washed with 50 ml of ethyl acetate. The filtrate and the washings were combined. The organic layer was separated, washed with an aqueous saturated sodium chloride solution, and dried over anhydrous magnesium sulfate. The solvent was removed by distillation under reduced pressure. The residue was recrystallized from n-propanol to obtain 340 mg (yield: 93%) of 2-(2-dimethylaminoethyl)-9-hydroxy-5-methyl-1H-[1]benzothieno[3,2-e]isoindole-1,3(2H)-dione as yellow crystals.

Melting point: 249.0°-254.2° C.
IR (KBr) cm$^{-1}$: 1760, 1690.

The following compound was obtained in the same manner.

2-(2-Diethylaminoethyl)-9-hydroxy-5-methyl-1H-[1]benzothieno[3,2-e]isoindole-1,3(2H)-dione
Melting point: 209.5°-211.4° C. (nPA).
IR (KBr) cm$^{-1}$: 1760, 1700.

(2)

The following compounds were obtained in the same manner as in Example 22 (2).

2-(2-Dimethylaminoethyl)-9-hydroxy-5-methyl-1H-[1]benzothieno[3,2-e]isoindole-1,3(2H)-dione hydrochloride
IR (KBr) cm$^{-1}$: 1760, 1700.

2-(2-Diethylaminoethyl)-9-hydroxy-5-methyl-1H-[1]benzothieno[3,2-e]isoindole-1,3(2H)-dione hydrochloride
IR (KBr) cm$^{-1}$: 1760, 1705.

EXAMPLE 24

(1) N-(2-dimethylaminoethyl)-1-methyl-6-methylaminocarbonyloxy-9-methylaminocarbonylcarbazole-3,4-dicarboximide To 4 ml of pyridine were added 180 mg of N-(2-dimethylaminoethyl)-6-hydroxy-1-methylcarbazole-3,4-dicarboximide, 150 mg of methyl isocyanate and 100 mg of dibutyltin diacetate. The mixture was stirred at room temperature overnight. The solvent was removed by distillation under reduced pressure. The residue was mixed with 5 ml of diethyl ether. The mixture was stirred at room temperature for 10 minutes. The resulting insoluble material was collected by filtration and purified by column chromatography (eluant: chloroform/methanol=40/1 to 30/1) to obtain 80 mg (yield: 33%) of N-(2-di(methylaminoethyl)-1-methyl-6-methylaminocarbonyloxy-9-methylaminocarbonylcarbazole-3,4-dicarboximide as light yellow crystals.

IR (KBr) cm$^{-1}$: 3330, 1750, 1700.

(2)

The following compound was obtained in the same manner as in Example 1 (2).

N-(2-dimethylaminoethyl)-1-methyl-6-methylaminocarbonyloxy-9-methylaminocarbonylcarbazole-3,4-dicarboximide hydrochloride

EXAMPLE 25

The compounds shown in Table 45 were obtained in the same manner as in Example 12 (1) and (2).

In Table 45, $R^1$, $R^3$, Y and Z refer to the respective substituents in the compound represented by the following formula.

TABLE 45

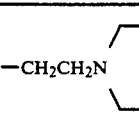

| $R^1$ | $R^3$ | —Y—Z | Melting point* (°C.) | IR (KBr) cm$^{-1}$:* |
|---|---|---|---|---|
| 6-MeO— | 1-Me— | —CH$_2$CH$_2$N(morpholino) | >260 / — | 1745, 1685 / 1750, 1695 |
| " | " | —CH$_2$CH$_2$OH | >260 | 3430, 3170, 1750, 1690 |
| " | 1-H$_2$C=CH—(CH$_2$)$_8$ | —CH$_2$CH$_2$NMe$_2$ | 151.0–152.5 / — | 1755, 1700 / 1755, 1700 |
| " | 2-N(phenyl)— | " | >260 / — | 1750, 1695 / 1755, 1700 |
| 6-MeO— | 1-(furyl)— | —CH$_2$CH$_2$NMe$_2$ | — / — | 1750, 1700 / 1755, 1700 |
| 6-MeO— 7-Br | 1-Me$_2$NCH$_2$— | " | 203.5–205.5 / — | 1750, 1700 / 1760, 1700 |
| 6-MeO— | 1-CH$_2$=CH— | " | 233.4–236.9 / — | 1750, 1695 / 1750, 1700 |

TABLE 45-continued

[Structure: carbazole with R¹, R³ substituents, and a dicarboximide group with N—Y—Z]

| R¹ | R³ | —Y—Z | Melting point* (°C.) | IR (KBr) cm⁻¹:* |
|---|---|---|---|---|
| " | 1- HC=O | " | 242.0-243.8 | 3380, 1740, 1700, 1670 |
| | | | — | 1760, 1705, 1675 |

Note:
*The upper section shows physical properties of a free form.
The lower section shows physical properties of a hydrochloride.

EXAMPLE 26

The following compounds were obtained in the same manner as in Example 1 (1) and (2):

N-[2-(diethylamino)ethyl]-6-methoxy-1-phenoxycarbazole-3,4-dicarboximide
IR (KBr) cm⁻¹: 1755, 1695.

N-[2-(dimethylamino)ethyl]-6-benzyloxy-1-(4-methoxyphenyloxy)carbazole-3,4-dicarboximide Melting point: 216.2°-217.9° C.
IR (KBr) cm⁻¹: 1755, 1700.

EXAMPLE 27

The compounds shown in Table 46 were obtained in the same manner as in Example 4 (1) and (2).

In Table 46, R¹, R³, Y and Z refer to the respective substituents in the compound represented by the following formula.

TABLE 46

[Structure: carbazole with R¹, R³ substituents, and a dicarboximide group with N—Y—Z]

| R¹ | R³ | —Y—Z | Melting point* (°C.) | IR (KBr) cm⁻¹:* |
|---|---|---|---|---|
| 6- HO— | 1- Me | —CH₂CH₂N(morpholine, O) | >260 | 3400, 3250, 1740, 1680 |
| | | | — | 1755, 1700 |
| " | " | —CH₂CH₂N(piperazine, NMe) | >260 | 3360, 1750, 1690 |
| | | | — | 1750, 1690 |
| " | " | —CH₂CH₂N(CH₂CH₂OH)₂ | 201.0-202.7 | 3380, 3200, 1750, 1690 |
| | | | — | 1750, 1680 |
| " | 1- HO—C₆H₄—O— | —CH₂CH₂NMe₂ | >260 | 3380, 1750, 1700 |
| | | | — | 1755, 1705 |
| 6- HO— | 1- C₆H₅—O— | —CH₂CH₂NEt₂ | 216.2-217.9 | 1750, 1690 |
| | | | — | 1760, 1705 |
| " | 2- N-pyridyl— | —CH₂CH₂NMe₂ | >260 | 1745, 1690 |
| | | | — | 1755, 1700 |

TABLE 46-continued

| R¹ | R³ | —Y—Z | Melting point* (°C.) | IR (KBr) cm⁻¹:* |
|---|---|---|---|---|
| " | " | " | — | 1745, 1700 |
| | 1-[cyclic structure with O] | | — | 1750, 1700 |

Note:
*The upper section shows physical properties of a free form.
The lower section shows physical properties of a hydrochloride.

EXAMPLE 28

The following compounds were obtained in the same manner as in Example 18 (1) and (2):
N-[2-(dimethylamino)ethyl]-6-hydroxy-1-(4-methoxyphenyloxy)carbazole-3,4-dicarboximide
Melting point: >260° C.
IR (KBr) cm⁻¹: 3430, 1750, 1685.
N-[2-(dimethylamino)ethyl]-6-hydroxy-1-(4-methoxyphenyloxy)carbazole-3,4-dicarboximide hydrochloride
IR (KBr) cm⁻¹: 1755, 1700.

EXAMPLE 29

The following compound was obtained in the same manner as in Example 8:
N-[2-(trimethylammonio)ethyl]-6-hydroxy-1-methylcarbazole-3,4-dicarboximide iodide
Melting point: >260° C.
IR (KBr) cm⁻¹: 3460, 3230, 1750, 1695.

EXAMPLE 30

(1)

The following compound was obtained in the same manner as in Example 10 (1):
N-(2-bromoethyl)-6-methoxy-1-methylcarbazole-3,4-dicarboximide
Melting point: 246.9°–249.3° C.
IR (KBr) cm⁻¹: 3350, 1750, 1680.

(2)

The following compounds were obtained in the same manner as in Example 10 (2):
N-(2-pyridinioethyl)-6-methoxy-1-methylcarbazole-3,4-dicarboximide bromide
Melting point: >260° C.
IR (KBr) cm⁻¹: 1750, 1700.
N-[2-bis(2-hydroxyethyl)aminoethyl]-6-methoxy-1-methylcarbazole-3,4-dicarboximide
Melting point: 196.0°–199.0° C.
IR (KBr) cm⁻¹: 1740, 1685.
N-[2-(4-methylpiperazinyl)ethyl]-6-methoxy-1-methylcarbazole-3,4-dicarboximide
Melting point: >260° C.
IR (KBr) cm⁻¹: 1745, 1685.

PREPARATION EXAMPLE 1

1 g of N-(2-dimethylaminoethyl)-6-hydroxycarbazole-3,4-dicarboximide hydrochloride (Compound No. 23) was dissolved in 500 ml of an aqueous 5% mannitol solution. The resulting solution was subjected to sterile filtration using a 0.22-μm filter. The filtrate was filled into a vial. The vial was subjected to lyophilization according to a conventional method to obtain an injection vial.

The injection vials for the following compounds were obtained in the same manner as above:
N-(2-dimethylaminoethyl)-6-hydroxy-1-methylcarbazole-3,4-dicarboximide hydrochloride
Compound No. 24
N-(2-diethylaminoethyl)-6-hydroxy-1-methylcarbazole-3,4-dicarboximide hydrochloride (Compound No. 42)
N-(2-dimethylaminoethyl)-1-cyclopropyl-6-hydroxycarbazole-3,4-dicarboximide hydrochloride
Compound No. 49
N-(2-dimethylaminoethyl)-1-cyclobutyl-6-hydroxy-carbazole-3,4-dicarboximide hydrochloride
Compound No. 59
N-(2-diethylaminoethyl)-6-hydroxy-1-methoxycarbazole-3,4-dicarboximide hydrochloride
Compound No. 70

PREPARATION EXAMPLE 2

There were mixed 5 g of N-(2-dimethylaminoethyl)-6-hydroxycarbazole-3,4-dicarboximide hydrochloride (Compound No. 23), 57.4 g of lactose, 25 g of corn starch and 20 g of crystalline cellulose. Thereto was added a solution of 2 g of hydroxypropyl cellulose dissolved in 18 ml of water. The mixture was kneaded.

The kneaded product was subjected to granulation process to obtain powder, dried, mixed with 0.6 g of magnesium stearate, and formulated into tablets (110 mg/tablet).

The following compounds were formulated into respective tablets in the same manner as above:
N-(2-dimethylaminoethyl)-6-hydroxy-1-methylcarbazole-3,4-dicarboximide hydrochloride
Compound No. 24
N-(2-diethylaminoethyl)-6-hydroxy-1-methylcarbazole-3,4-dicarboximide hydrochloride (Compound No. 42)
N-(2-dimethylaminoethyl)-1-cyclopropyl-6-hydroxycarbazole-3,4-dicarboximide hydrochloride
Compound No. 49
N-(2-dimethylaminoethyl)-1-cyclobutyl-6-hydroxycarbazole-3,4-dicarboximide hydrochloride
Compound No. 59

N-(2-diethylaminoethyl)-6-hydroxy-1-methoxycarbazole-3,4-dicarboximide hydrochloride
Compound No. 70

What is claimed is:

1. An isoindole of the following formula or a salt thereof:

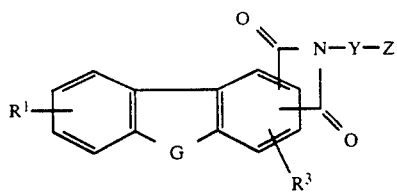

wherein

R¹ and R³ may be the same or different, and each of them is at least one atom or group selected from the group consisting of hydrogen and halogen atoms, nitro and methylenedioxy groups, unprotected or protected amino, hydroxyl and carboxyl groups and unsubstituted or substituted lower alkyl, alkenyl, lower alkylthio, cycloalkyl, aryl, aryloxy, carbamoyloxy, acyl, heterocyclic carbonyloxy and heterocyclic groups, said heterocyclic groups and the heterocyclic group for said heterocyclic carbonyloxy group being selected from the group consisting of pyrrolidinyl, piperidinyl, piperazinyl, morpholinyl, thienyl, furyl, pyrrolyl, pyrazolyl, pyridyl, pyridazinyl and pyrazinyl group, G is an oxygen atom or a group of the formula $>S(=O)_n$ in which n is 0, 1 or 2, Y is a bond or a lower alkylene group, Z is a halogen atom, an unprotected or protected hydroxyl group, a group of the formula

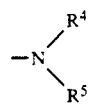

(in which R⁴ and R⁵, which may be the same or different, are hydrogen atoms or unsubstituted or substituted lower alkyl, cycloalkyl, aralkyl, acyl or aryl groups, or may form, with the nitrogen atom to which they are bonded, an unsubstituted or substituted nitrogen-containing 5- or 6-membered heterocyclic group selected from the group consisting of pyrrolidinyl, piperidinyl, piperazinyl, morpholinyl, triazolyl and tetrazolyl groups) or a trialkylammonio or cyclic ammonio group, and the group of the formula:

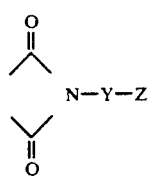

where Y and Z have the same means as defined above, is bonded to the 1- and 2- positions or 2- and 3- positions of the benzofuran or dibenzothiophene skeleton.

2. An isoindole of the following formula or a salt thereof:

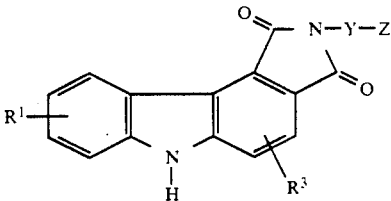

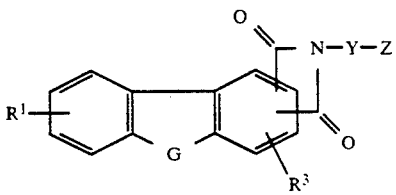

wherein

R¹ is a hydroxyl or protected hydroxyl group;

R³ is at least one member selected from the group consisting of halogen atoms, nitro, methylenedioxy, unprotected or protected amino, hydroxyl and carboxyl groups and unsubstituted or substituted lower alkyl, aryl and aryloxy groups;

Y is a lower alkylene group and

Z is a group of the formula NR⁴R⁵, wherein R⁴ and R⁵ are lower alkyl groups.

3. An isoindole derivative according to claim 1, wherein the group represented by the formula

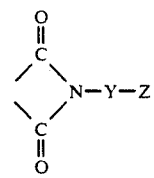

in which Y and Z have the same meanings as defined in claim 1, is bonded to 2- and 3-positions of a dibenzofuran or dibenzothiophene skeleton.

4. An isoindole derivative according to claim 3, wherein R¹ and R³ may be the same or different, and each of them is at least one atom or group selected from the group consisting of hdyrogen and halogen atoms, nitro and methylenedioxy groups, unprotected or protected amino, hydroxyl and carboxyl groups and unsubstituted or substituted lower alkyl, aryl and aryloxy groups.

5. An isoindole derivative according to claim 4, wherein R¹ and R³ may be the same or different, and each of them is at least one atom or group selected from the group consisting of hydrogen atom, unprotected or protected hydroxyl groups and unsubstituted or substituted lower alkyl groups.

6. An isoindole derivative according to any one of claims 3 to 5, wherein Y is a lower alkylene group.

7. An isoindole derivative according to any one of claims 3 to 6, wherein Z is a group represented by by the formula $$-N\begin{matrix}R^4\\R^5\end{matrix}$$

in which R⁴ and R⁵, which may be the same or different, represent hydrogen atoms or an unsubstituted or substituted lower alkyl, cycloalkyl, aralkyl, or aryl groups, or may form, with the nitrogen atom to which they are bonded, an unsubstituted or substituted nitrogen-containing 5- or 6-membered heterocyclic group selected from the group consisting of pyrrolidinyl, piperidinyl, piperazinyl, morpholinyl, triazolyl and tetrazolyl groups.

8. An isoindole derivative according to claim 7, wherein each of R⁴ and R⁵ is an unsubstituted or substituted lower alkyl group.

9. N-(2-ethylaminoethyl)-6-hydroxy-1-methylcarbazole-3,4-dicarboximide or a pharmaceutically acceptable salt thereof.

10. N-[2-(methylamino)ethyl]-6-hydroxy-1-methylcarbazole-3,4-dicarboximide or a pharmaceutically acceptable salt thereof.

11. N-(2-dimethylaminoethyl)-6-hydroxy-1-methylcarbazole-3,4-dicarboximide or a pharmaceutically acceptable salt thereof.

12. N-(2-diethylaminoethyl)-6-hydroxy-1-methylcarbazole-3,4-dicarboximide or a pharmaceutically acceptable salt thereof.

13. N-(2-dimethylaminoethyl)-1-cyclopropyl-6-hydroxycarbazole-3,4-dicarboximide or a pharmaceutically acceptable salt thereof.

14. N-(2-dimethylaminoethyl)-1-cyclobutyl-6-hydroxycarbazole-3,4-dicarboximide or a pharmaceutically acceptable salt thereof.

15. N-(2-dimethylaminoethyl)-1-chloro-6-hydroxycarbazole-3,4-dicarboximide or a pharmaceutically acceptable salt thereof.

16. N-(2-dimethylaminoethyl)-6-hydroxy-1-phenoxycarbazole-3,4-dicarboximide or a pharmaecutically acceptable salt thereof.

17. N-(2-dimethylaminoethyl)-6-hydroxy-1-methoxycarbazole-3,4-dicarboximide or a pharmaceutically acceptable salt thereof.

18. N-(2-dimethylaminoethyl)-6-hydroxy-1-(2-methylcyclopropyl)carbazole-3,4-dicarboxyimide or a pharmaceutically acceptable salt thereof.

19. N-(2-dimethylaminoethyl)-6-hydroxy-1-phenylcarbazole-3,4-dicarboximide or a pharmaceutically acceptable salt thereof.

20. An antitumor agent comprising an isoindole having the formula shown below or a salt thereof:

wherein
R¹ and R³ may be the same or different, and each of them is at least one atom or group selected from the group consisting of hydrogen and halogen atoms, nitro and methylenedioxy groups, unprotected or protected amino, hydroxyl and carboxyl groups and unsubstituted or substituted lower alkyl, alkenyl, lower alkythio, cycloalkyl, aryl, aryloxy, carbamoyloxy, acyl, heterocyclic carbonyloxy and heterocyclic groups, said heterocyclic group and the heterocyclic group for said heterocyclic carbonyloxy group being selected from the group consisting of pyrrolidinyl, piperidinyl, piperazinyl, morpholinyl, thienyl, furyl, pyrrolyl, pyrazolyl, pyridyl, pyridazinyl and pyrazinyl group, G is an oxygen atom or a group represented by the formula $$>S(=O)_n$$

in which n is 0, 1 or 2,

Y is a linkage or a lower alkylene group,

Z is a halogen atom, an unprotected or protected hydroxyl group, a group represented by the formula, $$-N\begin{matrix}R^4\\R^5\end{matrix}$$

(in which R⁴ and R⁵, which may be the same or different are hydrogen atoms or unsubstituted or substituted lower alkyl, cycloalkyl, aralkyl, or aryl groups, or may form, with the nitrogen atom to which they are bonded, an unsubstituted or substituted nitrogen-containing 5- or 6-membered heterocyclic group selected from the group consisting of pyrrolidinyl, piperidinyl, piperazinyl, morpholinyl, triazolyl and tetrazolyl groups), or a trialkylammonio or cyclic ammonio group, and the group of the formula:

wherein Y and Z have the same meanings as defined above, is bonded to the 1- and 2- positions or 2- and 3- positions of the dibenzofuran or dibenzothiophene skeleton and a suitable carrier, excipient or diluent.

21. An antitumor composition, comprising the isoindole of claim 2 and a suitable carrier, excipient or diluent.

* * * * *